(12) United States Patent
Wiles et al.

(10) Patent No.: US 9,732,103 B2
(45) Date of Patent: Aug. 15, 2017

(54) CARBAMATE, ESTER, AND KETONE COMPOUNDS FOR TREATMENT OF COMPLEMENT MEDIATED DISORDERS

(71) Applicant: Achillion Pharmaceuticals, Inc., New Haven, CT (US)

(72) Inventors: Jason Allan Wiles, Madison, CT (US); Venkat Rao Gadhachanda, Hamden, CT (US); Godwin Pais, Hamden, CT (US); Akihiro Hashimoto, Branford, CT (US); Qiuping Wang, Bethany, CT (US); Dawei Chen, Guilford, CT (US); Xiangzhu Wang, Branford, CT (US); Atul Agarwal, Hamden, CT (US); Milind Deshpande, Madison, CT (US); Avinash S. Phadke, Branford, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 14/631,440

(22) Filed: Feb. 25, 2015

(65) Prior Publication Data
US 2015/0239919 A1 Aug. 27, 2015

Related U.S. Application Data

(60) Provisional application No. 61/944,189, filed on Feb. 25, 2014, provisional application No. 62/022,916, filed on Jul. 10, 2014, provisional application No. 62/046,783, filed on Sep. 5, 2014.

(51) Int. Cl.
| | |
|---|---|
| *C07D 209/42* | (2006.01) |
| *C07D 403/12* | (2006.01) |
| *C07F 9/572* | (2006.01) |
| *C07D 403/14* | (2006.01) |
| *C07D 401/14* | (2006.01) |
| *C07D 471/04* | (2006.01) |
| *C07D 417/06* | (2006.01) |
| *C07D 403/06* | (2006.01) |
| *C07D 417/14* | (2006.01) |

(Continued)

(52) U.S. Cl.
CPC .......... *C07F 9/5728* (2013.01); *A61K 31/404* (2013.01); *A61K 31/407* (2013.01); *A61K 31/4162* (2013.01); *A61K 31/4178* (2013.01); *A61K 31/4184* (2013.01); *A61K 31/4188* (2013.01); *A61K 31/4192* (2013.01); *A61K 31/437* (2013.01); *A61K 31/4439* (2013.01); *A61K 31/4709* (2013.01); *A61K 31/496* (2013.01); *A61K 31/506* (2013.01); *A61K 31/549* (2013.01); *A61K 31/55* (2013.01); *A61K 31/675* (2013.01); *A61K 31/683* (2013.01); *C07B 59/002* (2013.01); *C07D 209/14* (2013.01); *C07D 209/40* (2013.01); *C07D 209/42* (2013.01); *C07D 401/14* (2013.01); *C07D 403/06* (2013.01); *C07D 403/08* (2013.01); *C07D 403/12* (2013.01); *C07D 403/14* (2013.01); *C07D 405/12* (2013.01); *C07D 405/14* (2013.01); *C07D 413/06* (2013.01); *C07D 413/14* (2013.01); *C07D 417/06* (2013.01); *C07D 417/12* (2013.01); *C07D 417/14* (2013.01); *C07D 471/04* (2013.01); *C07D 487/04* (2013.01); *C07D 487/14* (2013.01); *C07D 491/113* (2013.01); *C07D 495/04* (2013.01); *C07D 513/04* (2013.01); *C07F 5/025* (2013.01); *C07F 5/027* (2013.01); *C07F 7/0812* (2013.01); *C07F 9/6561* (2013.01); *C07F 9/65583* (2013.01); *C07F 9/65616* (2013.01); *C07B 2200/05* (2013.01)

(58) Field of Classification Search
CPC ........................... C07D 209/42; C07D 403/12
See application file for complete search history.

(56) References Cited

U.S. PATENT DOCUMENTS

| | | |
|---|---|---|
| 6,653,340 B1 | 11/2003 | Babu et al. |
| 2010/0041628 A1 | 2/2010 | Enomoto et al. |

(Continued)

FOREIGN PATENT DOCUMENTS

| | | |
|---|---|---|
| WO | WO 93/20099 A2 | 10/1993 |
| WO | WO 95/29697 A1 | 11/1995 |

(Continued)

OTHER PUBLICATIONS

Airey et al. "A Convenient Preparation of Thieno[3,2-c]pyrazole" Synthesis, 2014; 46: 96-100.
Barraclough et al. "Synthesis of (2S,3R)- and (@S,3S)-[3-2H1]-proline via highly selective hydrolysis of a silyl enol ether" Tetrahedron Letters, 2005; 46: 4653-4655.
Barraclough et al. "Two separate and distinct syntheses of stereospecifically deuteriated samples of (2S)-proline" Organic & Biomolecular Chemistry, 2006; 4: 1483-1491.
Cole et al. "Structure of 3,4-Dichloroisocoumarin-Inhibited Factor D" Acta Crystallographica, 1998; D54: 711-717.

(Continued)

*Primary Examiner* — Shawquia Jackson
(74) *Attorney, Agent, or Firm* — Knowles Intellectual Property Strategies, LLC

(57) ABSTRACT

Compounds, methods of use, and processes for making inhibitors of complement factor D comprising Formula I, or a pharmaceutically acceptable salt or composition thereof, wherein $R^{12}$ or $R^{13}$ on the A group is a carbamate, ester, or ketone substituent ($R^{32}$) are provided. The inhibitors described herein target factor D and inhibit or regulate the complement cascade at an early and essential point in the alternative complement pathway, and reduce factor D's ability to modulate the classical and lectin complement pathways. The inhibitors of factor D described herein are capable of reducing the excessive activation of complement, which has been linked to certain autoimmune, inflammatory, and neurodegenerative diseases, as well as ischemia-reperfusion injury and cancer.

29 Claims, No Drawings

Related U.S. Application Data

(51) Int. Cl.

| | |
|---|---|
| C07F 7/08 | (2006.01) |
| C07D 413/14 | (2006.01) |
| C07D 487/04 | (2006.01) |
| C07D 405/14 | (2006.01) |
| C07D 403/08 | (2006.01) |
| C07D 413/06 | (2006.01) |
| C07F 5/02 | (2006.01) |
| C07F 9/6561 | (2006.01) |
| C07F 9/6558 | (2006.01) |
| A61K 31/404 | (2006.01) |
| A61K 31/407 | (2006.01) |
| A61K 31/4162 | (2006.01) |
| A61K 31/4178 | (2006.01) |
| A61K 31/4184 | (2006.01) |
| A61K 31/4188 | (2006.01) |
| A61K 31/4192 | (2006.01) |
| A61K 31/437 | (2006.01) |
| A61K 31/4439 | (2006.01) |
| A61K 31/4709 | (2006.01) |
| A61K 31/496 | (2006.01) |
| A61K 31/506 | (2006.01) |
| A61K 31/549 | (2006.01) |
| A61K 31/55 | (2006.01) |
| A61K 31/675 | (2006.01) |
| A61K 31/683 | (2006.01) |
| C07B 59/00 | (2006.01) |
| C07D 209/14 | (2006.01) |
| C07D 209/40 | (2006.01) |
| C07D 405/12 | (2006.01) |
| C07D 417/12 | (2006.01) |
| C07D 487/14 | (2006.01) |
| C07D 491/113 | (2006.01) |
| C07D 495/04 | (2006.01) |
| C07D 513/04 | (2006.01) |

(56) References Cited

U.S. PATENT DOCUMENTS

| | | |
|---|---|---|
| 2011/0280808 A1 | 11/2011 | Kroth et al. |
| 2012/0295884 A1 | 11/2012 | Altmann et al. |
| 2013/0296377 A1 | 11/2013 | Adams et al. |
| 2015/0239837 A1 | 8/2015 | Wiles et al. |
| 2015/0239838 A1 | 8/2015 | Phadke et al. |
| 2015/0239868 A1 | 8/2015 | Pais et al. |
| 2015/0239893 A1 | 8/2015 | Wang et al. |
| 2015/0239894 A1 | 8/2015 | Gadhachanda et al. |
| 2015/0239895 A1 | 8/2015 | Gadhachanda et al. |
| 2015/0239920 A1 | 8/2015 | Gadhachanda et al. |
| 2015/0239921 A1 | 8/2015 | Wiles et al. |

FOREIGN PATENT DOCUMENTS

| | | |
|---|---|---|
| WO | WO 99/48492 A1 | 9/1999 |
| WO | WO 2004/007501 A1 | 1/2004 |
| WO | WO 2004/045518 A2 | 6/2004 |
| WO | WO 2004/111041 A1 | 12/2004 |
| WO | WO 2008/047831 A1 | 4/2008 |
| WO | WO 2012/093101 A1 | 7/2012 |
| WO | WO 2012/177782 A1 | 12/2012 |
| WO | WO 2013/166436 A1 | 11/2013 |
| WO | WO 2014/002051 A2 | 1/2014 |
| WO | WO 2014/002052 A1 | 1/2014 |
| WO | WO 2014/002053 A1 | 1/2014 |
| WO | WO 2014/002054 A1 | 1/2014 |
| WO | WO 2014/002057 A1 | 1/2014 |
| WO | WO 2014/002058 A2 | 1/2014 |
| WO | WO 2014/002059 A1 | 1/2014 |
| WO | WO 2014/005150 A1 | 1/2014 |
| WO | WO 2014/009833 A2 | 1/2014 |
| WO | WO 2014/037480 A1 | 3/2014 |
| WO | WO 2015/130784 A1 | 9/2015 |
| WO | WO 2015/130795 A1 | 9/2015 |
| WO | WO 2015/130806 A1 | 9/2015 |
| WO | WO 2015/130838 A1 | 9/2015 |
| WO | WO 2015/130842 A2 | 9/2015 |
| WO | WO 2015/130845 A1 | 9/2015 |
| WO | WO 2015/130854 A1 | 9/2015 |

OTHER PUBLICATIONS

De Luca et al. "HIV-1 integrase strand-transfer inhibitors: Design, synthesis and molecular modeling investigation" European Journal of Medicinal Chemistry, 2011; 46: 756-764.

Donthiri et al. "Copper-Catalyzed C—H Functionalization of Pyridines and Isoquinolines with Vinyl Azides: Synthesis of Imidazo Heterocycles" Journal of Organic Chemistry, 2014; 79: 11277-11284.

Dormoy et al. "Synthesis of N-t-Butoxycarbonyl-4,4-dideuterio-L-proline" Synthesis, 1986; 1: 81-82.

Hecker et al. "Liver-Targeted Prodrugs of 2'-C-Methyladenosine for Therapy of Hepatitis C Virus Infection" Journal of Medicinal Chemistry, 2007; 50(16): 3891-3896.

Hruby et al. "Carbon-13 NMR studies of the Peptide hormones oxytocin, arginine vasopressin, isotocin, mesotocin, glumitocin, aspartocin, related analogs, and diastereoisomers. Use of specifically deuterated hormone derivatives for assignments and effects of structural changes on carbon-13 NMR chemical shifts in peptides" Journal of the American Chemical Society, 1979; 101(1): 202-212.

Kobayashi et al. "Carboxylation of alkynylsilanes with carbon dioxide mediated by cesium fluoride in DMSO" Organic & Biomolecular Chemistry, 2013; 11: 3773-3775.

Kuang et al. "Synthesis of (Z)-1-bromo- 1 -alkenes and terminal alkynes from anti-2,3-dibromoalkanoic acids by microwave-induced reaction" Tetrahedron, 2006; 61(16): 4043-4052.

Mackay et al. "Rapid Synthesis of the N-Methylwelwitindolinone Skeleton" Organic Letters, 2005; 7: 3421-3424.

Okutani et al. "Conversion of Bromoalkenes into Alkynes by Wet Tetra-n-butylammonium Fluoride" Journal of Organic Chemistry, 2009; 74: 442-444.

Quesada et al. "One-pot conversion of activated alcohols into terminal alkynes using manganese dioxide in combination with the Bestmann-Ohira reagent" Tetrahedron Letters, 2005; 46: 6473-6476.

Roth et al. "Further Improvements of the Synthesis of Alkynes from Aldehydes" Synthesis, 2004; 1: 59-62.

Ruiz-Gomez et al. "Structure-Activity Relationships for Substrate-Based Inhibitors of Human Complement Factor B" Journal of Medicinal Chemistry, 2009; 52: 6042-6052.

Tandon et al. "Substrate specificity of human prolyl-4-hydroxylase" Bioorganic and Medicinal Chemistry Letters, 1998; 8(10): 1139-1144.

Tang et al. "Palladium-Catalyzed Carbonylative Sonogashira Coupling of Aryl Bromides via tert-Butyl Isocyanide Insertion" Journal of Organic Chemistry, 2013; 78(7): 3170-3175.

International Search Report and Written Opinion for PCT/US2015/017523 mailed May 14, 2015.

International Search Report and Written Opinion for PCT/US2015/017538 mailed May 14, 2015.

International Search Report and Written Opinion for PCT/US2015/017554 mailed May 14, 2015.

International Search Report and Written Opinion for PCT/US2015/017583 mailed May 27, 2015.

International Search Report and Written Opinion for PCT/US2015/017593 mailed Jun. 16, 2015.

International Search Report and Written Opinion for PCT/US2015/017597 mailed Jan. 29, 2016.

International Search Report and Written Opinion for PCT/US2015/17600 mailed May 27, 2015.

International Search Report and Written Opinion for PCT/US2015/017609 mailed May 29, 2015.

CARBAMATE, ESTER, AND KETONE COMPOUNDS FOR TREATMENT OF COMPLEMENT MEDIATED DISORDERS

CROSS-REFERENCE TO RELATED APPLICATIONS

This application claims the benefit of provisional U.S. Application No. 61/944,189 filed Feb. 25, 2014, provisional U.S. Application No. 62/022,916 filed Jul. 10, 2014, and provisional U.S. Application 62/046,783 filed Sep. 5, 2014. The entirety of each of these applications is hereby incorporated by reference for all purposes.

BACKGROUND

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phaogytosis of antigens), chemotaxis (attracting macrophages and neutrophils), cell lysis (rupturing membranes of foreign cells) and agglutination (clustering and binding of pathogens together).

The complement system has three pathways: classical, alternative and lectin. Complement factor D plays an early and central role in activation of the alternative pathway of the complement cascade. Activation of the alternative complement pathway is initiated by spontaneous hydrolysis of a thioester bond within C3 to produce C3(H2O), which associates with factor B to form the C3(H2O)B complex. Complement factor D acts to cleave factor B within the C3(H2O)B complex to form Ba and Bb. The Bb fragment remains associated with C3(H2O) to form the alternative pathway C3 convertase C3(H2O)Bb. Additionally, C3b generated by any of the C3 convertases also associates with factor B to form C3bB, which factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement factor H have a fivefold increased risk of macular degeneration and individuals with mutations in other complement factor genes also have an increased risk of AMD. Individuals with mutant factor H also have increased levels of C-reactive protein, a marker of inflammation. Without adequate functioning factor H, the alternative pathway of the complement cascade is overly activated leading to cellular damage. Inhibition of the alternative pathway is thus desired.

Paroxysmal nocturnal hemoglobinuria (PNH) is a non-malignant, hematological disorder characterized by the expansion of hematopoietic stem cells and progeny mature blood cells which are deficient in some surface proteins. PNH erythrocytes are not capable of modulating their surface complement activation, which leads to the typical hallmark of PNH—the chronic activation of complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections. Thus, there is an unmet need to develop novel inhibitors of the complement pathway.

Factor D is an attractive target for inhibition or regulation of the complement cascade due to its early and essential role in the alternative complement pathway, and its potential role in signal amplification within the classical and lectin complement pathways. Inhibition of factor D effectively interrupts the pathway and attenuates the formation of the membrane attack complex.

While initial attempts have been made to develop inhibitors of factor D, there are currently no small molecule factor D inhibitors in clinical trials. Examples of factor D inhibitors or prolyl compounds are described in the following disclosures.

Biocryst Pharmaceuticals U.S. Pat. No. 6,653,340 titled "Compounds useful in the complement, coagulat and kallikrein pathways and method for their preparation" describes fused bicyclic ring compounds that are potent inhibitors of factor D. Development of the factor D inhibitor BCX1470 was discontinued due to lack of specificity and short half-life of the compound.

Novartis PCT patent publication WO2012/093101 titled "Indole compounds or analogues thereof useful for the treatment of age-related macular degeneration" describes certain factor D inhibitors.

Novartis PCT patent publications WO2014/002057 titled "Pyrrolidine derivatives and their use as complement pathway modulators" and WO2014/009833 titled "Complement pathway modulators and uses thereof" describe additional factor D inhibitors with heterocyclic substituents. Additional factor D inhibitors are described in Novartis PCT patent publications WO2014/002051, WO2014/002052, WO2014/002053, WO2014/002054, WO2014/002058, WO2014/002059, and WO2014/005150.

Bristol-Myers Squibb PCT patent publication WO2004/045518 titled "Open chain prolyl urea-related modulators of androgen receptor function" describes open chain prolyl urea and thiourea related compounds for the treatment of androgen receptor-associated conditions, such as age-related diseases, for example, sarcopenia.

Japan Tobacco Inc. PCT patent publication WO1999/048492 titled "Amide derivatives and nociceptin antagonists" describes compounds with a proline-like core and aromatic substituents connected to the proline core through amide linkages useful for the treatment of pain.

Ferring B. V. and Yamanouchi Pharmaceutical Co. 1TD. PCT patent publication WO1993/020099 titled "CCK and/or gastrin receptor ligands" describes compounds with a proline-like core and heterocyclic substituents connected to the proline core through amide linkages for the treatment of, for example, gastric disorders or pain.

Alexion Pharmaceuticals PCT patent publication WO1995/029697 titled "Methods and compositions for the treatment of glomerulonephritis and other inflammatory diseases" discloses antibodies directed to C5 of the complement pathway for the treatment of glomerulonephritis and inflammatory conditions involving pathologic activation of the complement system. Alexion Pharmaceutical's anti-C5 antibody eculizumab (Soliris®) is currently the only complement-specific antibody on the market, and is the first and only approved treatment for paroxysmal nocturnal hemoglobinuria (PNH).

Compounds which mediate the complement pathway, and for example, act as factor D inhibitors are needed for treatment of disorders in a host, including a human, associated with misregulation of the complement cascade.

SUMMARY

It has been discovered that a compound of Formula I, or a pharmaceutically acceptable salt or composition thereof, wherein $R^{12}$ or $R^{13}$ on the A group is a carbamate, ester, or ketone substituent, is a superior inhibitor of complement factor D.

In one embodiment, a method for the treatment of a disorder associated with a dysfunction, including increased activity, of the complement pathway is provided that includes the administration of an effective amount of a compound of Formula I, or a pharmaceutically acceptable salt thereof, optionally in a pharmaceutically acceptable carrier, as described in more detail below.

In one embodiment, the disorder is associated with the alternative complement cascade pathway. In yet another embodiment, the disorder is associated with the complement classical pathway. In a further embodiment, the disorder is associated with the complement lectin pathway. The factor D inhibitors provided herein can thus dampen or inhibit detrimental complement activity in a host, by administration of an effective amount in a suitable manner to a host in need thereof.

Specific embodiments of this invention are directed to certain disease indications. In one embodiment, a method for the treatment of paroxysmal nocturnal hemoglobinuria (PNH) is provided that includes the administration of an effective amount of a compound of Formula I, or a pharmaceutically acceptable salt thereof, optionally in a pharmaceutically acceptable carrier. In another embodiment, a method for the treatment of age-related macular degeneration (AMD) is provided that includes the administration of an effective amount of a compound of Formula I, or a pharmaceutically acceptable salt thereof, optionally in a pharmaceutically acceptable carrier. In another embodiment, a method for the treatment of rheumatoid arthritis is provided that includes the administration of an effective amount of a compound of Formula I, or a pharmaceutically acceptable salt thereof, optionally in a pharmaceutically acceptable carrier. In another embodiment, a method for the treatment of multiple sclerosis is provided that includes the administration of an effective amount of a compound of Formula I, or a pharmaceutically acceptable salt thereof, optionally in a pharmaceutically acceptable carrier.

In other embodiments of the invention, an active compound provided herein can be used to treat or prevent a disorder in a host mediated by complement factor D, or by an excessive or detrimental amount of the C3 amplification loop of the complement pathway. As examples, the invention includes methods to treat or prevent complement associated disorders that are induced by antibody-antigen interactions, a component of an immune or autoimmune disorder or by ischemic injury. The invention also provides methods to decrease inflammation or an immune response, including an autoimmune response, where mediated or affected by factor D.

The disclosure provides compounds of Formula I

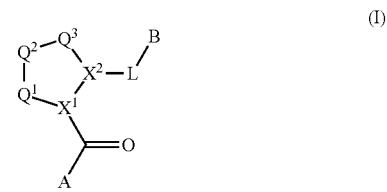

and the pharmaceutically acceptable salts and compositions thereof, wherein:

$Q^1$ is $N(R^1)$ or $C(R^1R^{1'})$;

$Q^2$ is $C(R^2R^{2'})$, $C(R^2R^{2'})$—$C(R^2R^{2'})$, S, O, $N(R^1)$ or $C(R^2R^{2'})O$;

$Q^3$ is $N(R^3)$, S, or $C(R^3R^{3'})$;

$X^1$ and $X^2$ are independently N, CH, or CZ, or $X^1$ and $X^2$ together are C=C; and wherein $Q^1$, $Q^2$, $Q^3$, $X^1$, and $X^2$ are selected such that a stable compound results.

Non-limiting examples of the

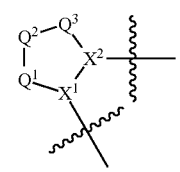

ring are illustrated below (any of which can be otherwise substituted with $R^1$, $R^{1'}$, $R^2$, $R2'$, $R^3$ and $R^{3'}$) as described in more detail below.

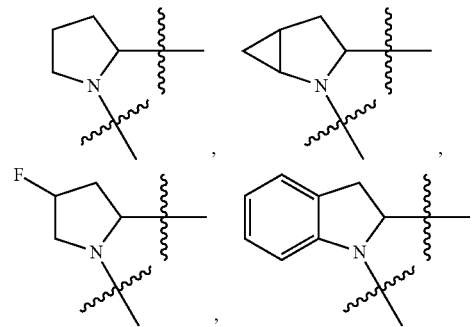

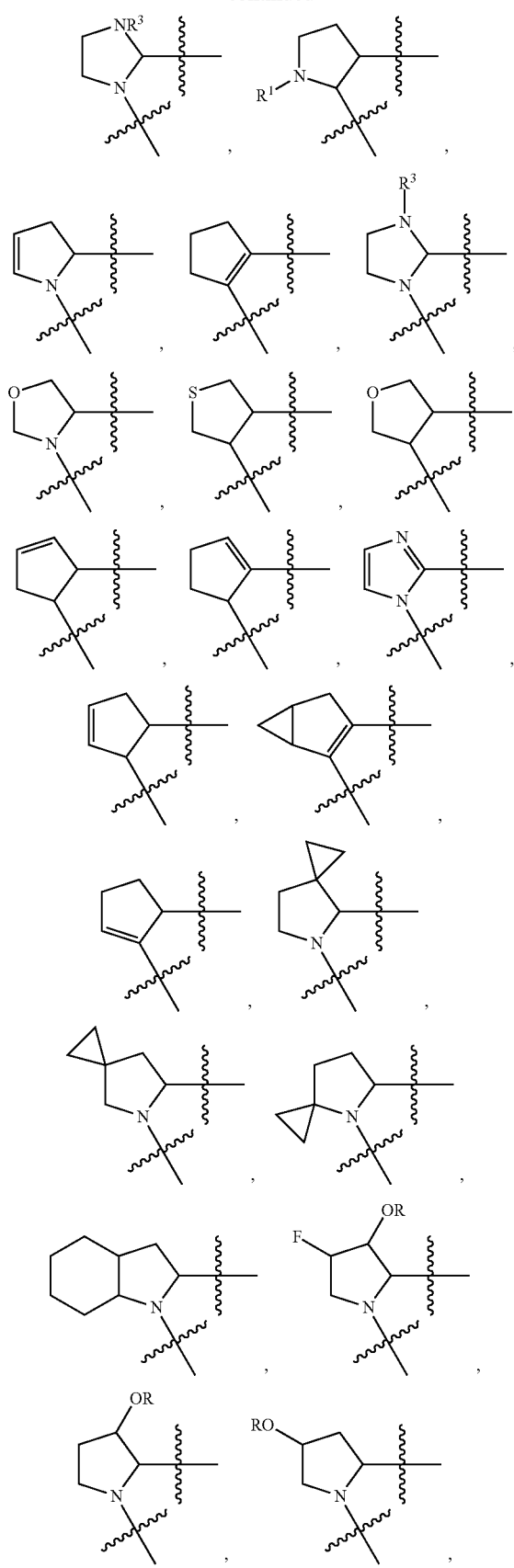
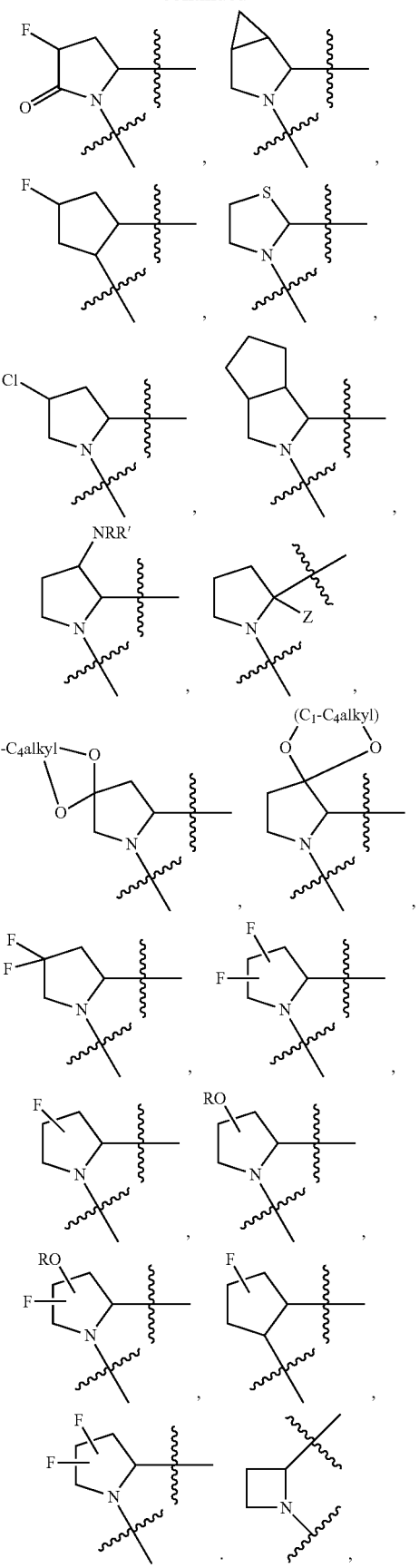

-continued

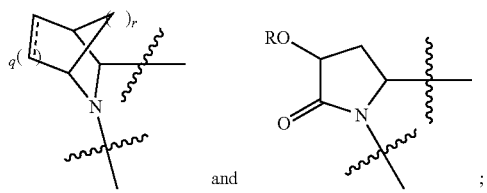

wherein q is 0, 1, 2 or 3 and r is 1, 2 or 3.

R and $R^1$ are independently chosen from H, alkyl, cycloalkyl, cycloalkylalkyl, heterocycle, heterocycloalkyl, aryl, arylalkyl, heteroaryl, heteroarylalkyl wherein each group can be optionally substituted or any other substituent group herein that provides the desired properties. In some embodiments, the ring includes one or more chiral carbon atoms. The invention includes embodiments in which the chiral carbon can be provided as an enantiomer, or mixtures of enantiomers, including a racemic mixture. Where the ring includes more than one stereocenter, all of the enantiomers and diastereomers are included in the invention as individual species.

Z is F, Cl, $NH_2$, $CH_3$, $CH_2D$, $CHD_2$, or $CD_3$.

$R^1$, $R^{1'}$, $R^2$, $R^{2'}$, $R^3$, and $R^{3'}$ are independently chosen at each occurrence, as appropriate, and only where a stable compound results, from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C2$-$C_6$alkanoyl, $C_1$-$C_6$thioalkyl, hydroxy$C_1$-$C_6$alkyl, amino$C_1$-$C_6$alkyl, —$C_0$-$C_4$alkylNR$^9$R$^{10}$, —C(O)OR$^9$, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, $C_1$-$C_2$haloalkyl, and $C_1$-$C_2$haloalkoxy, where $R^9$ and $R^{10}$ are independently chosen at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl).

In alternative embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently chosen from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which spiro ring each of which ring may be unsubstituted or substituted with 1 or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^2$ may be taken together to form a 3-membered carbocyclic ring; $R^1$ and $R^2$ may be taken together to form a 4- to 6-membered carbocyclic or aryl ring or a 4- to 6-membered heterocyclic or heteroaryl ring containing 1 or 2 heteroatoms independently chosen from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring; each of which ring may be unsubstituted or substituted with 1 or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di—$C_1$-$C_4$alkylamino)$C_0$-$C_4$alkyl, —$C_0$-$C_4$alkyl(C3-C7cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^{1'}$, $R^2$ and $R^{2'}$, or $R^3$ and $R^{3'}$ can be taken together to form a carbonyl group. In alternative embodiments, $R^1$ and $R^2$ or $R^2$ and $R^3$ can be taken together to form a carbon-carbon double bond.

A is a group chosen from:

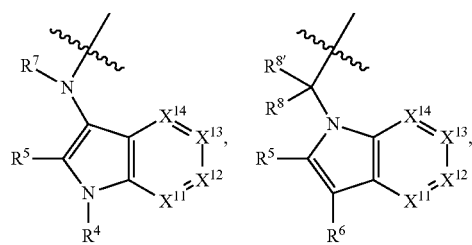

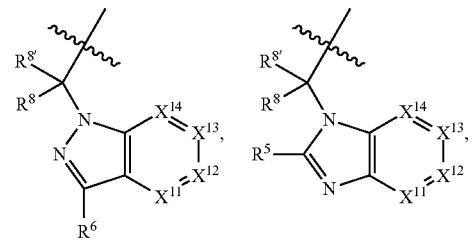

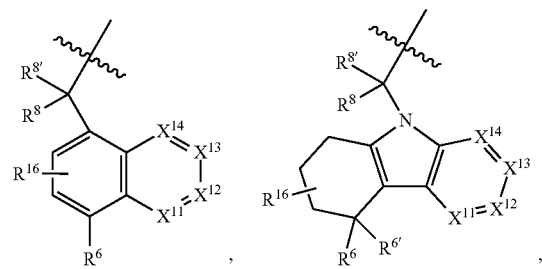

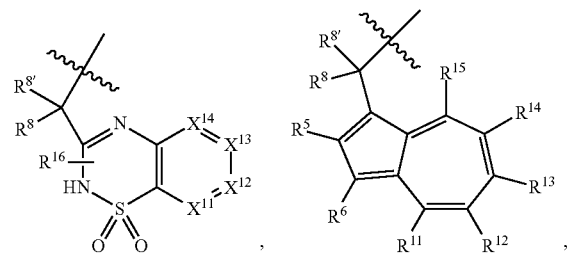

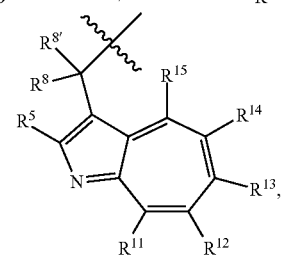

-continued

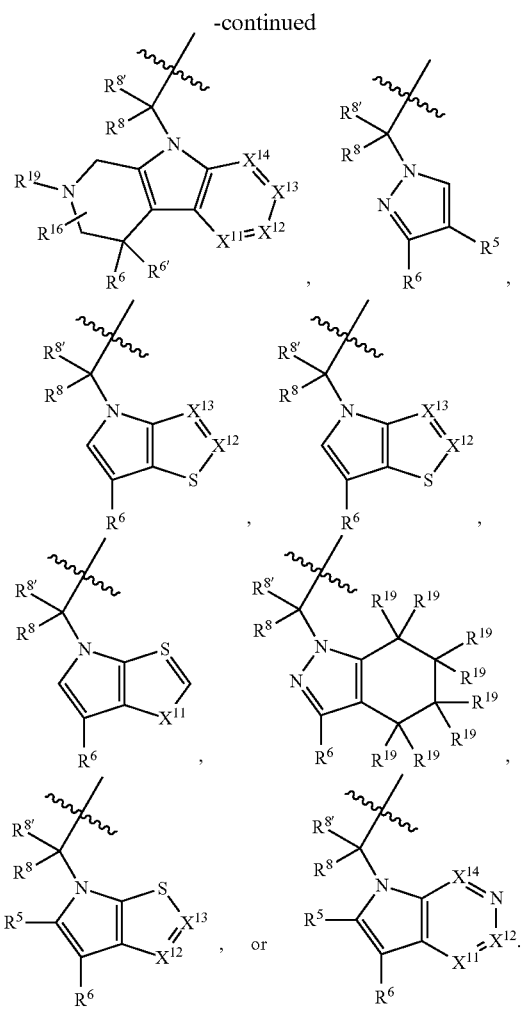

$R^4$ is chosen from —CHO, —CONH$_2$, C$_2$-C$_6$alkanoyl, hydrogen, —SO$_2$NH$_2$, —C(CH$_2$)$_2$F, —CH(CF$_3$)NH$_2$, C$_1$-C$_6$alkyl, —C$_0$-C$_4$alkyl(C$_3$-C$_7$cycloalkyl), —C(O)C$_0$-C$_2$alkyl(C$_3$-C7cycloalkyl),

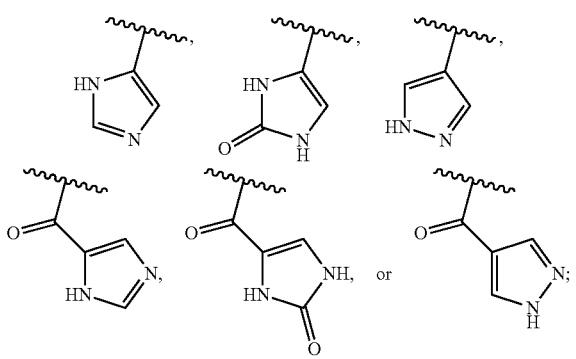

each of which $R^4$ other than hydrogen, —CHO, and —CONH$_2$, is unsubstituted or substituted with one or more of amino, imino, halogen, hydroxyl, cyano, cyanoimino, C$_1$-C$_2$alkyl, C$_1$-C$_2$alkoxy, —C$_0$-C$_2$alkyl(mono- and di—C$_1$-C$_4$alkylamino), C$_1$-C$_2$haloalkyl, and C$_1$-C$_2$haloalkoxy.

$R^5$ and $R^6$ are independently chosen from —CHO, —C(O)NH$_2$, —C(O)NH(CH$_3$), C$_2$-C$_6$alkanoyl, hydrogen, hydroxyl, halogen, cyano, nitro, —COOH, —SO$_2$NH$_2$, vinyl, C$_1$-C$_6$alkyl (including methyl), C$_2$-C$_6$alkenyl, C$_1$-C$_6$alkoxy, —C$_0$-C$_4$alkyl(C$_3$-C$_7$cycloalkyl), —C(O)C$_0$-C$_4$alkyl(C$_3$-C$_7$cycloalkyl), —P(O)(OR$^9$)$_2$, —OC(O)R$^9$, —C(O)OR$^9$, —C(O)N(CH$_2$CH$_2$R$^9$)(R$^{10}$), —NR$^9$C(O)R$^{10}$, phenyl, or 5- to 6-membered heteroaryl.

Each $R^5$ and $R^6$ other than hydrogen, hydroxyl, cyano, and —COOH is unsubstituted or optionally substituted. For example, $R^5$ and $R^6$ other than hydrogen, hydroxyl, cyano, and —COOH may be substituted with one or more substituents independently chosen from halogen, hydroxyl, amino, imino, cyano, cyanoimino, C$_1$-C$_2$alkyl, C$_1$-C$_4$alkoxy, —C$_0$-C$_2$alkyl(mono- and di-C$_1$-C$_4$alkylamino), C$_1$-C$_2$haloalkyl, and C$_1$-C$_2$haloalkoxy.

$R^{6'}$ is hydrogen, halogen, hydroxyl, C$_1$-C$_4$alkyl, —C$_0$-C$_4$alkyl(C$_3$-C$_7$cycloalkyl), or C$_1$-C$_4$alkoxy; or $R^6$ and $R^{6'}$ may be taken together to form an oxo, vinyl, or imino group.

$R^7$ is hydrogen, C$_1$-C$_6$alkyl, or —C$_0$-C$_4$alkyl(C$_3$-C$_7$cycloalkyl).

$R^8$ and $R^{8'}$ are independently chosen from hydrogen, halogen, hydroxyl, C$_1$-C$_6$alkyl, —C$_0$-C$_4$alkyl(C$_3$-C$_7$cycloalkyl), C$_1$-C$_6$alkoxy, and (C$_1$-C$_4$alkylamino)C$_0$-C$_2$alkyl; or $R^8$ and $R^{8'}$ are taken together to form an oxo group; or $R^8$ and $R^{8'}$ can be taken together with the carbon that they are bonded to form a 3-membered carbocyclic ring.

$R^{16}$ is absent or may include one or more substituents independently chosen from halogen, hydroxyl, nitro, cyano, C$_1$-C$_6$alkyl, C$_2$-C$_6$alkenyl, C$_2$-C$_6$alkanoyl, C$_1$-C$_6$alkoxy, —C$_0$-C$_4$alkyl(mono- and di-C$_1$-C$_6$alkylamino), —C$_0$-C$_4$alkyl(C$_3$-C$_7$cycloalkyl), C$_1$-C$_2$haloalkyl, and C$_1$-C$_2$haloalkoxy.

$R^{19}$ is hydrogen, C$_1$-C$_6$alkyl, C$_2$-C$_6$alkenyl, C$_2$-C$_6$alkanoyl, —SO$_2$C$_1$-C$_6$alkyl, (mono- and di-C$_1$-C$_6$alkylamino)C$_1$-C$_4$alkyl, —C$_0$-C$_4$alkyl(C$_3$-C$_7$cycloalkyl), —C$_0$-C$_4$alkyl(C3-C7heterocycloalkyl), —C$_0$-C$_4$alkyl(aryl), C$_0$-C$_4$alkyl(heteroaryl), and wherein $R^{19}$ other than hydrogen is unsubstituted or substituted with one or more substituents independently chosen from halogen, hydroxyl, amino, —COOH, and —C(O)OC$_1$-C$_4$alkyl.

$X^{11}$ is N or CR$^{11}$.
$X^{12}$ is N or CR$^{12}$.
$X^{13}$ is N or CR$^{13}$.
$X^{14}$ is N or CR$^{14}$.
No more than 2 of $X^{11}$, $X^{12}$, $X_{13}$, and $X^{14}$ are N.

One of $R^{12}$ and $R^{13}$ is chosen from $R^{31}$ and the other of $R^{12}$ and $R^{13}$ is chosen from $R^{32}$. In an alternative embodiment, $R^{12}$ and $R^{13}$ are each independently selected from an $R^{32}$ moiety.

$R^{31}$ is chosen from hydrogen, halogen, hydroxyl, nitro, cyano, amino, —COOH, C$_1$-C$_2$haloalkyl, C$_1$-C$_2$haloalkoxy, C$_1$-C$_6$alkyl, —C$_0$-C$_4$alkyl(C$_3$-C$_7$cycloalkyl), C$_2$-C$_6$alkenyl, C$_2$-C$_6$alkanoyl, C$_1$-C$_6$alkoxy, C$_2$-C$_6$alkenyloxy, —C(O)OR$^9$, C$_1$-C$_6$thioalkyl, —C$_0$-C$_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which R$^{31}$ other than hydrogen, halogen, hydroxyl, nitro, cyano, C$_1$-C$_2$haloalkyl, and C$_1$-C$_2$haloalkoxy is unsubstituted or substituted with one or more substituents independently selected from halogen, hydroxyl, nitro, cyano, amino, —COOH, —CONH$_2$ C$_1$-C$_2$haloalkyl, and C$_1$-C$_2$haloalkoxy, and each of which $R^{31}$ is also optionally substituted with one substituent chosen from phenyl and 4- to 7-membered heterocycle containing 1, 2, 3 or 4 heteroatoms independently chosen from N, O, and S; which phenyl or 4- to 7-membered heterocycle is unsubstituted or substituted with one or more substituents independently chosen from halogen, hydroxyl, nitro, cyano, C$_1$-C$_6$alkyl, C$_2$-C$_6$alkenyl, C$_2$-C$_6$alkanoyl, C$_1$-C$_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

$R^{32}$ is chosen from —OC(O)(CH$_2$)$_{1-4}$R$^{21}$, —OC(O)NR$^{21}$R$^{22}$, —OC(O)NR$^{24}$R$^{25}$, —OC(O)($C_{1-6}$alkyl or $C_{3-6}$cycloalkyl)(aryl), —OC(O)($C_{1-6}$alkyl or $C_{3-6}$cycloalkyl)(heteroaryl), —OC(O)($C_{1-6}$alkyl or $C_{3-6}$cycloalkyl)(heterocycle), —OC(O)(heteroaryl), —OC(O)(aryl), —OC(O)($C_1$-6alkyl or $C_{3-6}$cycloalkyl), —OC(O)NR$^9$(CH$_2$)$_{1-4}$P(O)(OR$^{21}$)(OR$^{22}$), —C(O)($C_{1-6}$alkyl or C3-6cycloalkyl)(aryl), —C(O)($C_{1-6}$alkyl or $C_{3-6}$cycloalkyl)(heteroaryl), —C(O)($C_{1-6}$alkyl or C3-6cycloalkyl)(heterocycle), —C(O)(heteroaryl), —C(O)(heterocycle), —C(O)(aryl), —C(O)($C_{1-6}$alkyl or $C_{3-6}$cycloalkyl) and —C(O)(CH$_2$)S(O)R$^{21}$, each of which is optionally substituted in any selected position on the alkyl, aryl, heteroaryl or heterocyclic moiety as described herein.

$R^{11}$, $R^{14}$, and $R^{15}$ are independently chosen at each occurrence from hydrogen, halogen, hydroxyl, nitro, cyano, —O(PO)(OR$^9$)$_2$, —(PO)(OR$^9$)$_2$, $C_1$-$C_6$alkyl, $C_2$-$C_6$alkenyl, $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy(C3-C7cycloalkyl), $C_1$-$C_2$haloalkyl, and $C_1$-$C_2$haloalkoxy.

$R^{21}$ and $R^{22}$ are independently chosen at each occurrence from hydrogen, hydroxyl, amino, $C_1$-$C_6$alkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)C$_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently chosen from N, O, and S, and (unsaturated or aromatic heterocycle)$C_0$-$C_4$alkyl having 1, 2, 3, or 4 heteroatoms independently chosen from N, O, and S each of which is optionally substituted.

$R^{23}$ is independently chosen at each occurrence from ($C_3$-$C_7$cycloalkyl)$C_0$-$C_4$alkyl, (aryl)$C_0$-$C_4$alkyl, (4- to 7-membered heterocycloalkyl)$C_0$-$C_4$alkyl having 1, 2, or 3 heteroatoms independently chosen from N, O, and S, and (5- or 6- membered unsaturated or aromatic heterocycle)$C_0$-$C_4$alkyl having 1, 2, or 3 heteroatoms independently chosen from N, O, and S each of which is optionally substituted.

$R^{24}$ and $R^{25}$ are taken together with the nitrogen to which they are attached to form a 4- to 7-membered monocyclic heterocycloalkyl group, or a 6- to 10- membered bicyclic heterocyclic group having fused, spiro, or bridged rings each of which is optionally substituted.

L is a bond or is chosen from the formulas

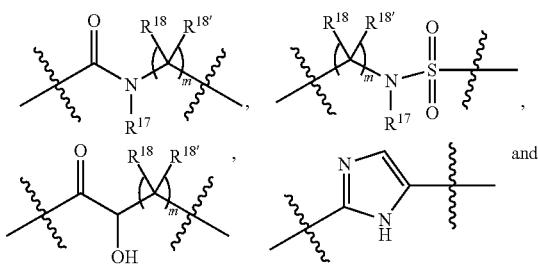

-continued

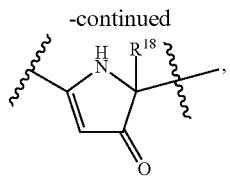

where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently chosen from hydrogen, halogen, hydroxymethyl, and methyl; and m is 0, 1, 2, or 3.

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl).

Each of which B is unsubstituted or substituted with one or more substituents independently chosen from $R^{33}$ and $R^{34}$, and 0 or 1 substituents chosen from $R^{35}$ and $R^{36}$.

$R^{33}$ is independently chosen from halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy.

$R^{34}$ is independently chosen from nitro, $C_2$-$C_6$alkenyl, $C_2$-$C_6$alkynyl, $C_1$-$C_6$thioalkyl, —JC$_3$-$C_7$cycloalkyl, —B(OH)$_2$, —JC(O)NR$^9$R$^{23}$, —JOSO2OR$^{21}$, —C(O)(CH$_2$)$_{1-4}$S(O)R$^{21}$, —O(CH$_2$)$_{1-4}$S(O)NR$^{21}$R$^{22}$, —JOP(O)(OR$^{21}$)(OR$^{22}$), —JP(O)(OR$^{21}$)(OR$^{22}$), —JOP(O)(OR$^{21}$)R$^{22}$, —JNR(O)(OR$^{21}$)R$^{22}$, —JOP(O)R$^{21}_R{}^{22}$, —JP(O)R$^{21}$R$^{22}$, —JSP(O)(OR$^{21}$)(OR$^{22}$), —JSP(O)(OR$^{21}$)(R$^{22}$), —JSP(O)(R$^{21}$)(R$^{22}$), —JNR$^9$P(O)(NHR$^{21}$)(NHR$^{22}$), —JNR$^9$P(O)(OR$^{21}$)(NHR$^{22}$), —JNR$^9$P(O)(OR$^{21}$)(OR$^{22}$), —JC(S)R$^{21}$, —JNR$^{21}$SO$_2$R$^{22}$, —JNR$^9$S(O)NR$^{10}$R$^{22}$, —JNR$^9$SO$_2$NR$^{10}$R$^{22}$, —JSO$_2$NR$^9$COR$^{22}$, —JSO$_2$NR$^9$CONR$^{21}$R$^{22}$, —JNR$^{21}$SO$_2$R$^{22}$, —JC(O)NR$^{21}$SO$_2$R$^{22}$, —JC(NH$_2$)NR$^{22}$, —JC(NH$_2$)NR$^9$S(O)$_2$R$^{22}$, —JOC(O)NR$^{21}$R$^{22}$, —JNR$^{21}$C(O)OR$^{22}$, —JNR$^{21}$OC(O)R$^{22}$, (CH$_2$)$_{1-4}$C(O)NR$^{21}$R$^{22}$, —JC(O)R$^{24}$R$^{25}$, —JNR$^9$C(O)R$^{21}$, —JC(O)R$^{21}$, —JNR$^9$C(O)NR$^{10}$R$^{22}$, —CCR$^{21}$, —(CH$^2$)$_{1-4}$OC(O)R$^{21}$, and —JC(O)OR$^{23}$; each of which $R^{34}$ may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

$R^{35}$ is independently chosen from naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7- ring atoms in each ring; each of which $R^{35}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, $C_1$-$C_2$haloalkyl, and $C_1$-$C_2$haloalkoxy.

$R^{36}$ is independently chosen from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which $R^{36}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, —$OSi(CH_3)_2C(CH_3)_3$, —$Si(CH_3)_2C(CH_3)_3$, $C_1$-$C_2$haloalkyl, and $C_1$-$C_2$haloalkoxy.

J is independently chosen at each occurrence from a covalent bond, $C_1$-$C_4$alkylene, —$OC_1$-$C_4$alkylene, $C_2$-$C_4$alkenylene, and $C_2$-$C_4$alkynylene.

Pharmaceutical compositions comprising a compound or salt of Formula I together with a pharmaceutically acceptable carrier are also disclosed.

Methods of treating or preventing disorders mediated by complement cascade factor D, including but not limited to age-related macular degeneration (AMD), retinal degeneration, other ophthalmic diseases (e.g., geographic atrophy), paroxysymal nocturnal hemoglobinuria (PNH), multiple sclerosis (MS), arthritis including rheumatoid arthritis (RA), a respiratory disease or a cardiovascular disease, are provided, comprising administering a therapeutically effective amount of a compound or salt of Formula I to a host, including a human, in need of such treatment are also disclosed.

In another embodiment, an effective amount of an active factor D inhibiting compound is provided to treat an inflammatory or immune disorder, including an autoimmune disorder, that is meadited or affected by factor D. In an alternative embodiment, the compound of Formula I can be used to treat a disorder mediated by the complement pathway, regardless whether it is acting through Factor D.

The present invention includes at least the following features:

(a) a compound of Formula I as described herein, and pharmaceutically acceptable salts and prodrugs thereof (each of which and all subgenuses and species thereof considered individually and specifically described);

(b) Formula I as described herein, and pharmaceutically acceptable salts and prodrugs thereof, for use in treating or preventing disorders mediated by the complement pathway, and for example, cascade factor D, including age-related macular degeneration (AMD), retinal degeneration, paroxysymal nocturnal hemoglobinuria (PNH), multiple sclerosis (MS), and rheumatoid arthritis (RA) and other disorders described further herein;

(c) use of Formula I, and pharmaceutically acceptable salts and prodrugs thereof in the manufacture of a medicament for use in treating or preventing disorders mediated by complement cascade factor D, including age-related macular degeneration (AMD), retinal degeneration, paroxysymal nocturnal hemoglobinuria (PNH), multiple sclerosis (MS), and rheumatoid arthritis (RA) and other disorders described further herein;

(d) a process for manufacturing a medicament intended for the therapeutic use for treating or preventing treating or preventing disorders mediated by complement cascade factor D, including age-related macular degeneration (AMD), retinal degeneration, paroxysymal nocturnal hemoglobinuria (PNH), multiple sclerosis (MS), and rheumatoid arthritis (RA) and other disorders described further herein characterized in that Formula I as described herein is used in the manufacture;

(e) a pharmaceutical formulation comprising an effective host-treating amount of the Formula I or a pharmaceutically acceptable salt or prodrug thereof together with a pharmaceutically acceptable carrier or diluent;

(f) Formula I as described herein in substantially pure form, including substantially isolated from other chemical entities (e.g., at least 90 or 95%);

(g) processes for the manufacture of the compounds of Formula I and salts, compositions, dosage forms thereof; and (h) processes for the preparation of therapeutic products that contain an effective amount of Formula I, as described herein.

DETAILED DESCRIPTION

I. Terminology

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, tautomers, racemates and other isomers, such as rotamers, as if each is specifically described. "Formula I" includes all subgeneric groups of Formula I, such as Formula IA and Formula IB and also includes pharmaceutically acceptable salts of a compound of Formula I, unless clearly contraindicated by the context in which this phrase is used. "Formula I" also includes all subgeneric groups of Formula I, such as Formulas IC-ID, and Formulas II-XXX, and also includes pharmaceutically acceptable salts of all subgeneric groups of Formula I, such as Formulas IA-ID, and Formulas II-XXX, unless contraindicated by the context in which this phrase is used.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula I and the use of compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes isotopically modified compounds of Formula I. In one embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}$H) and tritium ($^{3}$H) may be used anywhere in described structures that achieves the desired result. Alternatively or in addition, isotopes of carbon, e.g., $^{13}$C and $^{14}$C, may be used. In one embodiment, the isotopic substitution is deuterium for hydrogen at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiments deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom occurs within an R group substituent on the L-B moiety region. In one embodiment, the substitution of a hydrogen atom for a deuterium atom occurs within an R group selected from any of $R^{18}$, $R^{18'}$, $R^{33}$, $R^{34}$, $R^{35}$, and/or $R^{36}$. In one embodiment, the substitution of a hydrogen atom for a deuterium atom occurs within an R group substituent within the A-carbonyl moiety region. In one embodiment, the substitution of a hydrogen atom for a deuterium atom occurs at $R^4$, $R^5$, $R^6$, $R^{6'}$, $R^7$, $R^8$, $R^{8'}$, $R^{11}$, $R^{12}$, $R^{13}$, $R^{14}$, $R^{15}$, $R^{16}$, $R^{19}$, $R^{21}$, $R^{22}$, $R^{23}$, $R^{30}$, and/or $R^{30a}$. In other embodiments, certain substituents on the proline ring are selectively deuterated. For example, in one embodiment, the substitution of a hydrogen atom for a deuterium atom occurs at R, R', $R^1$, $R^{1'}$, $R^2$, $R^{2'}$, $R^3$, and/or $R^{3'}$. In one embodiment, for example, when any of the R substituents of the proline ring are methyl or methoxy, the alkyl residue is optionally deuterated, e.g., CD$_3$ or OCD$_3$. In certain other embodiments, when two substituents of the proline ring are combined to form a cyclopropyl ring, the unsubstituted methylene carbon is deuterated.

The substitution of a hydrogen atom for a deuterium atom occurs within an R group when at least one of the variables within the R group is hydrogen (e.g., $^{2}$H or D) or alkyl (e.g., CD$_3$). For example, when any of R groups are, or contain for example through substitution, methyl or ethyl, the alkyl residue is typically deuterated, e.g., CD$_3$, CH$_2$CD$_3$ or CD$_2$CD$_3$.

The compound of the present invention may form a solvate with solvents (including water). Therefore, in one embodiment, the invention includes a solvated form of the active compound. The term "solvate" refers to a molecular complex of a compound of the present invention (including salts thereof) with one or more solvent molecules. Examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. D$_2$O, d$_6$-acetone, d$_6$-DMSO. A solvate can be in a liquid or solid form.

A dash ("—") that is not between two letters or symbols is used to indicate a point of attachment for a substituent. For example, —(C=O)NH$_2$ is attached through carbon of the keto (C=O) group.

The term "substituted", as used herein, means that any one or more hydrogens on the designated atom or group is replaced with a moiety selected from the indicated group, provided that the designated atom's normal valence is not exceeded. For example, when the substituent is oxo (i.e., =O) then two hydrogens on the atom are replaced. When an oxo group replaces two hydrogens in an aromatic moiety, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates.

A stable compound or stable structure refers to a compound leading to a compound that can be isolated and can be formulated into a dosage form with a shelf life of at least one month.

Any suitable group may be present on a "substituted" or "optionally substituted" position that forms a stable molecule and advances the desired purpose of the invention and includes, but is not limited to, e.g., halogen (which can independently be F, Cl, Br or I); cyano; hydroxyl; nitro; azido; alkanoyl (such as a C$_2$-C6 alkanoyl group); carboxamide; alkyl, cycloalkyl, alkenyl, alkynyl, alkoxy, aryloxy such as phenoxy; alkylthio including those having one or more thioether linkages; alkylsulfinyl; alkylsulfonyl groups including those having one or more sulfonyl linkages; aminoalkyl groups including groups having one or more N atoms; aryl (e.g., phenyl, biphenyl, naphthyl, or the like, each ring either substituted or unsubstituted aromatic); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated, unsaturated, or aromatic heterocyclic group having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently chosen from halogen, hydroxyl, amino, cyano, —CHO, —COOH, —CONH$_2$, C$_1$-C$_6$alkyl, C$_2$-C$_6$alkenyl, C$_2$-C$_6$alkynyl, -C$_1$-C$_6$alkoxy, C$_2$-C$_6$alkanoyl, C$_1$-C$_6$alkylester, (mono- and di-C$_1$-C$_6$alkylamino)C$_0$-C$_2$alkyl, C$_1$-C$_2$haloalkyl, hydroxyC$_1$-C$_6$alkyl, ester, carbamate, urea, sulfonamide, —C$_1$-C$_6$alkyl (heterocyclo), C$_1$-C$_6$alkyl(heteroaryl), —C$_1$-C$_6$alkyl(C$_3$-C$_7$cycloalkyl), O-C$_1$-C$_6$alkyl(C$_3$-C$_7$cycloalkyl), B(OH)$_2$, phosphate, phosphonate and C$_1$-C$_2$haloalkoxy.

"Alkyl" is a branched or straight chain saturated aliphatic hydrocarbon group. In one embodiment, the alkyl contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-C2, $C_1$-C3, or $C_1$-$C_6$. The specified ranges as used herein indicate an alkyl group having each member of the range described as an independent species. For example, the term $C_1$-C6 alkyl as used herein indicates a straight or branched alkyl group having from 1, 2, 3, 4, 5, or 6 carbon atoms and is intended to mean that each of these is described as an independent species. For example, the term $C_1$-Coalkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-C4 alkyl, or —$C_0$-$C_4$alkyl($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane and 2,3-dimethylbutane. In one embodiment, the alkyl group is optionally substituted as described above.

"Alkenyl" is a branched or straight chain aliphatic hydrocarbon group having one or more carbon-carbon double bonds that may occur at a stable point along the chain. Nonlimiting examples are $C_2$-$C_8$alkenyl, $C_2$-$C_6$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described above.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a bivalent saturated hydrocarbon. Alkylenes, for example, can be a 1 to 8 carbon moiety, 1 to 6 carbon moiety, or an indicated number of carbon atoms, for example $C_1$-$C_4$alkylene, $C_1$-$C_3$alkylene, or $C_1$-$C_2$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkoxy" is an alkyl group as defined above covalently bound through an oxygen bridge (—O—). Examples of alkoxy include, but are not limited to, methoxy, ethoxy, n-propoxy, i- propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Alkanoyl" is an alkyl group as defined above covalently bound through a carbonyl (C=O) bridge. The carbonyl carbon is included in the number of carbons, that is $C_2$alkanoyl is a $CH_3(C=O)$— group. In one embodiment, the alkanoyl group is optionally substituted as described above.

"Alkylester" is an alkyl group as defined herein covalently bound through an ester linkage. The ester linkage may be in either orientation, e.g., a group of the formula —O(C=O)alkyl or a group of the formula —(C=O)Oalkyl.

"Amide" or "carboxamide" is —C(O)NR$^a$R$^b$ wherein R$^a$ and R$^b$ are each independently selected from hydrogen, alkyl, for example, $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, R$^a$ and R$^b$ can form a $C_3$-$C_7$heterocyclic ring. In one embodiment, the R$^a$ and R$^b$ groups are each independently optionally substituted as described above.

"Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms.

"Carbocyclic-oxy group" is a monocyclic carbocyclic ring or a mono- or bi-cyclic carbocyclic group as defined above attached to the group it substitutes via an oxygen, —O—, linker.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Hydroxyalkyl" is an alkyl group as previously described, substituted with at least one hydroxyl sub situtuent.

"Aminoalkyl" is an alkyl group as previously described, substituted with at least one amino sub situtuent.

"Halo" or "halogen" indicates independently any of fluoro, chloro, bromo, and iodo.

"Aryl" indicates aromatic groups containing only carbon in the aromatic ring or rings. In one embodiment, the aryl groups contain 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above.

The term "heterocycle," or "heterocyclic ring" as used herein refers to a saturated or a partially unsaturated (i.e., having one or more double and/or triple bonds within the ring without aromaticity) carbocyclic radical of 3 to about 12, and more typically 3, 5, 6, 7 to 10 ring atoms in which at least one ring atom is a heteroatom selected from nitrogen, oxygen, phosphorus and sulfur, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, and S) or a bicycle having 6 to 10 ring members (4 to 9 carbon atoms and 1 to 6 heteroatoms selected from N, O, P, and S), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2] octane, 3-oxa-8-azabicyclo[3.2.1]octane, 8-oxa-3-azabicyclo[3.2.1] octane, 6-oxa-3-azabicyclo[3.1.1]heptane, 2-oxa-5-azabicyclo[2.2.1]heptane, 3-azabicyco[3.1.0] hexanyl, 3-azabicyclo[4.1.0]heptanyl, azabicyclo[2.2.2] hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (=O) moieties are pyrimidinonyl and 1,1-dioxo-thiomorpholinyl. The heterocycle groups herein are optionally substituted independently with one or more substituents described herein.

"Heterocyclicoxy group" is a monocyclic heterocyclic ring or a bicyclic heterocyclic group as described previously linked to the group it substitutes via an oxygen, —O—, linker.

"Heteroaryl" indicates a stable monocyclic aromatic ring which contains from 1 to 3, or in some embodiments from 1 to 2, heteroatoms chosen from N, O, and S, with remaining ring atoms being carbon, or a stable bicyclic or tricyclic ring system containing at least one 5- to 7-membered aromatic ring which contains from 1 to 3, or in some embodiments from 1 to 2, heteroatoms chosen from N, O, and S, with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein. "Heteroaryloxy" is a heteroaryl group as described bound to the group it substituted via an oxygen, —O—, linker.

"Heterocycloalkyl" is a saturated ring group. It may have, for example, 1, 2, 3, or 4 heteroatoms independently chosen from N, S, and O, with remaining ring atoms being carbon. In a typical embodiment, nitrogen is the heteroatm. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "mono- and/or di-alkylamino" indicates secondary or tertiary alkylamino groups, wherein the alkyl groups are independently chosen alkyl groups, as defined herein. The point of attachment of the alkylamino group is on the nitrogen. Examples of mono- and di-alkylamino groups include ethylamino, dimethylamino, and methyl-propylamino.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, such as a compound or salt of Formula I, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)n-COOH$ where n is 0-4, and the like. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, and includes, in one embodiment, an excipient that is acceptable for veterinary use as well as human pharmaceutical use. A "pharmaceutically acceptable excipient" as used in the present application includes both one and more than one such excipient.

A "patient" or "host" or "subject" is a human or non-human animal in need of modulation of the complement factor D pathway. Typically the host is a human. A "patient" or "host" or "subject" also refers to for example, mammals, primates (e.g., humans), cows, sheep, goats, horses, dogs, cats, rabbits, rats, mice, fish, birds and the like.

A "prodrug" as used herein, means a compound which when administered to a host in vivo is converted into a parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. In certain embodiments the compound of Formula I and the additional active agent need not be prescribed for a patient by the same medical care worker. In certain embodiments the additional active agent or agents need not require a prescription. Administration of the compound of Formula I or the at least one additional active agent can occur via any appropriate route, for example, oral tablets, oral capsules, oral liquids, inhalation, injection, suppositories or topical contact.

A "therapeutically effective amount" of a pharmaceutical composition/combination of this invention means an amount effective, when administered to a patient, to provide a therapeutic benefit such as an amelioration of symptoms, e.g., an amount effective to decrease the symptoms of a macular degeneration. In one embodiment, a therapeutically effective amount is an amount sufficient to prevent a significant increase or will significantly reduce the detectable level of complement factor D in the patient's blood, serum, or tissues.

II. Detailed Description of the Active Compounds

According to the present invention, a compound of Formula I is provided:

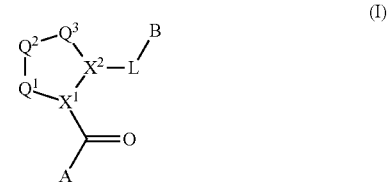

As well as the pharmaceutically acceptable salts and compositions thereof. Formula I can be considered to have a central core, an L-B substituent, and a (C=O)A substituent. It has been discovered that a compound of Formula I, or a pharmaceutically acceptable salt or composition thereof, wherein $R^{12}$ or $R^{13}$ on the A group is a carbamate, ester, or ketone substituent, is a superior inhibitor of complement factor D, and therefore can be used as an effective amount to treat a host in need of complement factor D modulation.

Non-limiting examples of compounds falling within Formula I with variations in the variables e.g., A, B, R¹-R³', and L, are illustrated below. The disclosure includes all combinations of these definitions so long as a stable compound results.

Formulas II-XXX

In one aspect, the disclosure includes compounds and salts of Formula II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX and XXX which are within the scope of Formula I. The variables shown in Formula II-XXX carry the definitions set forth in the SUMMARY section for Formula I or any of the definitions set forth in this disclosure.

Formula II
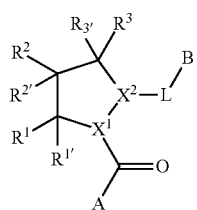

Formula III
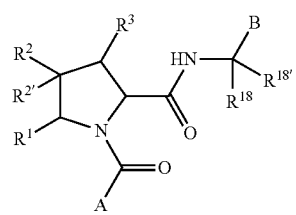

Formula IV
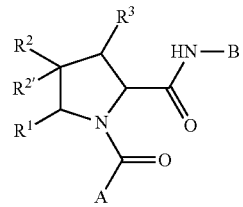

Formula V
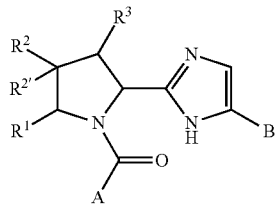

Formula VI
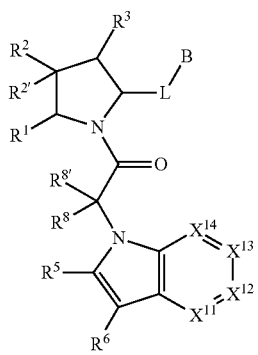

Formula VII
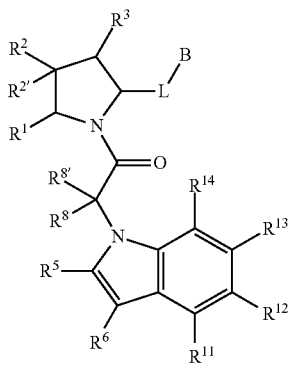

Formula VIII
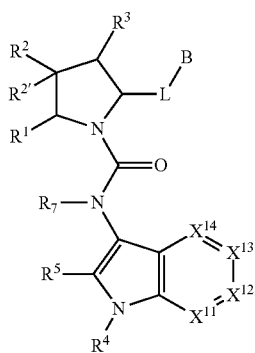

Formula IX
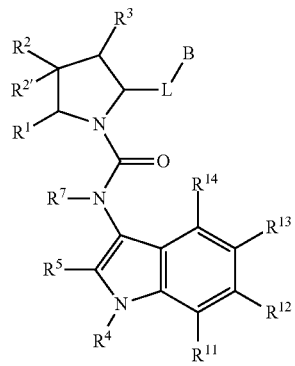

Formula X
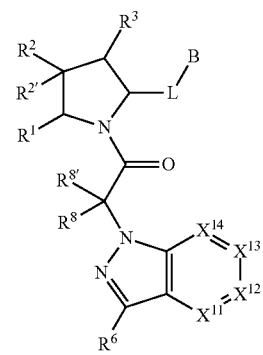

Formula XI, Formula XII, Formula XIII, Formula XIV, Formula XV, Formula XVI, Formula XVII, Formula XVIII, Formula XIX, Formula XX m is 0 or 1.

Formula XXI
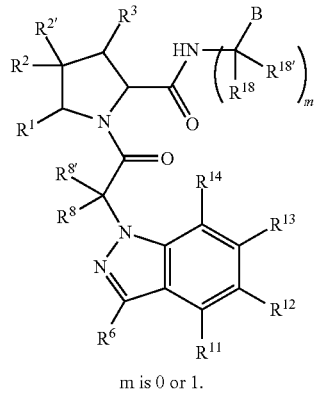
m is 0 or 1.
Formula XXII
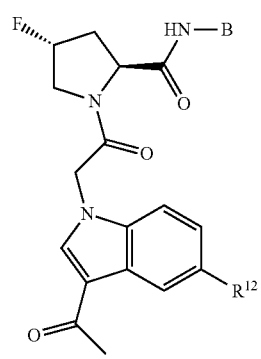
Formula XXIII
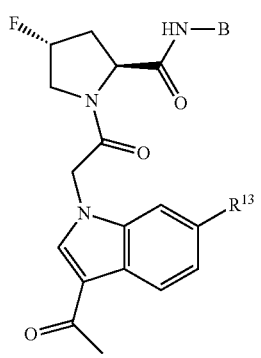
Formula XXIV
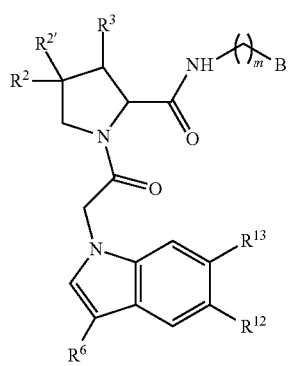
Formula XXV
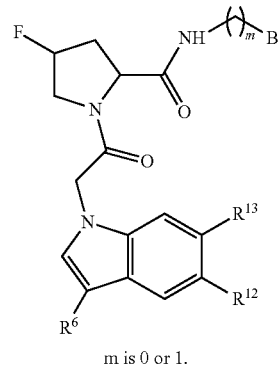
m is 0 or 1.
Formula XXVI
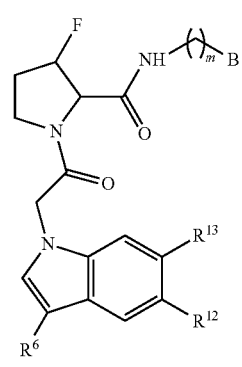
m is 0 or 1.
Formula XXVII
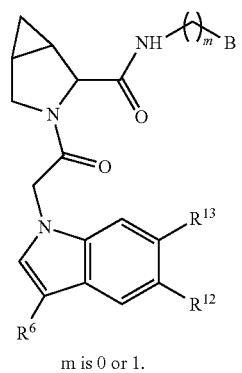
m is 0 or 1.
Formula XXVIII
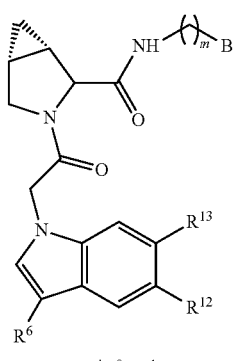
m is 0 or 1.

Formula XXIX

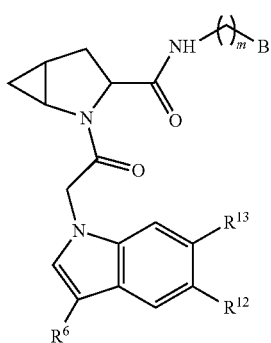

m is 0 or 1.

Formula XXX

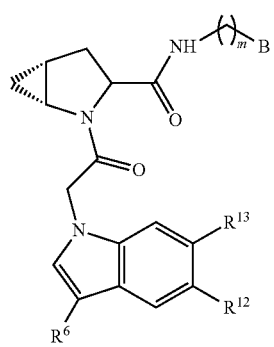

m is 0 or 1.

Additionally, the disclosure includes compounds and salts of Formula I and pharmaceutically acceptable compositions thereof, and any of its subformulae (II-XXX) in which at least one of the following conditions is met in the embodiments described below.

The $R^{12}$ and $R^{13}$ Carbamate, Ester, and Ketone Substituents

It has been discovered that a compound of Formula I, a pharmaceutically acceptable salt or composition thereof, wherein $R^{12}$ or $R^{13}$ on the A group is a carbamate, ester, or ketone substituent, is a superior inhibitor of complement factor D.

One of $R^{12}$ and $R^{13}$ is chosen from $R^{31}$ and the other of $R^{12}$ and $R^{13}$ is chosen from $R^{32}$. In another embodiment, each of $R^{12}$ and $R^{13}$ can be independently selected from $R^{32}$.

$R^{31}$ is chosen from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —CONH$_2$ $C_1$-$C_2$haloalkyl, and $C_1$-$C_2$haloalkoxy, and each of which $R^{31}$ is also optionally substituted with one substituent chosen from phenyl and 4- to 7-membered heterocycle containing 1, 2, 3, or 4 heteroatoms independently chosen from N, O, and S; which phenyl or 4- to 7-membered heterocycle is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), $C_1$-$C_2$haloalkyl, and $C_1$-$C_2$haloalkoxy;

$R^{32}$ is chosen from —OC(O)(CH$_2$)$_{1-4}$R$^{21}$, —OC(O)NR$^{21}$R$^{22}$, —OC(O)NR$^{24}$R$^{25}$, —OC(O)($C_{1-6}$alkyl or $C_{3-6}$cycloalkyl)(aryl), —OC(O)($C_{1-6}$alkyl or $C_{3-6}$cycloalkyl)(heteroaryl), —OC(O)($C_{1-6}$alkyl or $C_{3-6}$cycloalkyl)(heterocycle), —OC(O)(heteroaryl), —OC(O)(aryl), —OC(O)($C_1$-6alkyl or $C_{3-6}$cycloalkyl), —OC(O)NR$^9$(CH$_2$)$_{1-4}$P(O)(OR$^{21}$)(OR$^{22}$), —C(O)($C_{1-6}$alkyl or C3-6cycloalkyl)(aryl), —C(O)($C_{1-6}$alkyl or $C_{3-6}$cycloalkyl)(heteroaryl), —C(O)($C_{1-6}$alkyl or C3-6cycloalkyl)(heterocycle), —C(O)(heteroaryl), —C(O)(heterocycle), —C(O)(aryl), —C(O)($C_{1-6}$alkyl or $C_{3-6}$cycloalkyl) and —C(O)(CH$_2$)S(O)R$^{21}$, each of which is optionally substituted in any selected position on the alkyl, aryl, heteroaryl or heterocyclic moiety as described herein.

$R^{21}$ and $R^{22}$ are independently chosen at each occurrence from hydrogen, hydroxyl, amino, $C_1$-$C_6$alkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)C$_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently chosen from N, O, and S, and (unsaturated or aromatic heterocycle)$C_0$-$C_4$alkyl having 1, 2, 3, or 4 heteroatoms independently chosen from N, O, and S each of which is optionally substituted.

$R^{24}$ and $R^{25}$ are taken together with the nitrogen to which they are attached to form a 4- to 7-membered monocyclic heterocycloalkyl group, or a 6- to 10- membered bicyclic heterocyclic group having fused, spiro, or bridged rings each of which is optionally substituted.

In certain embodiments, $R^{32}$ is selected from:

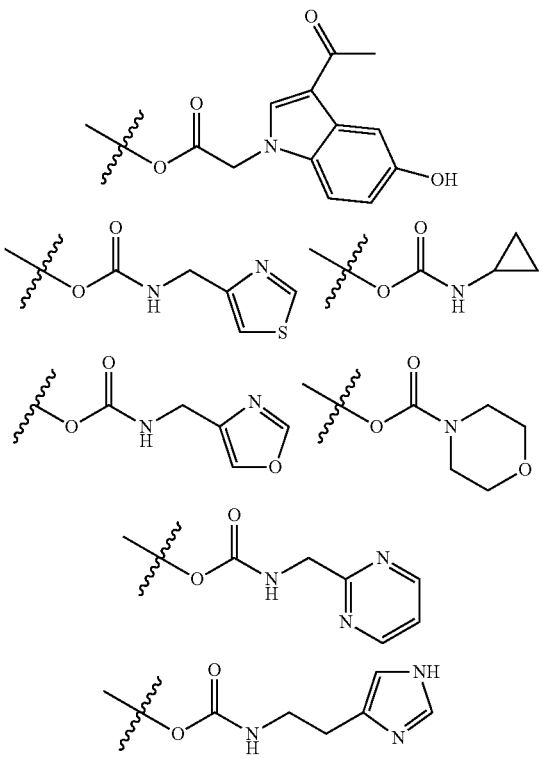

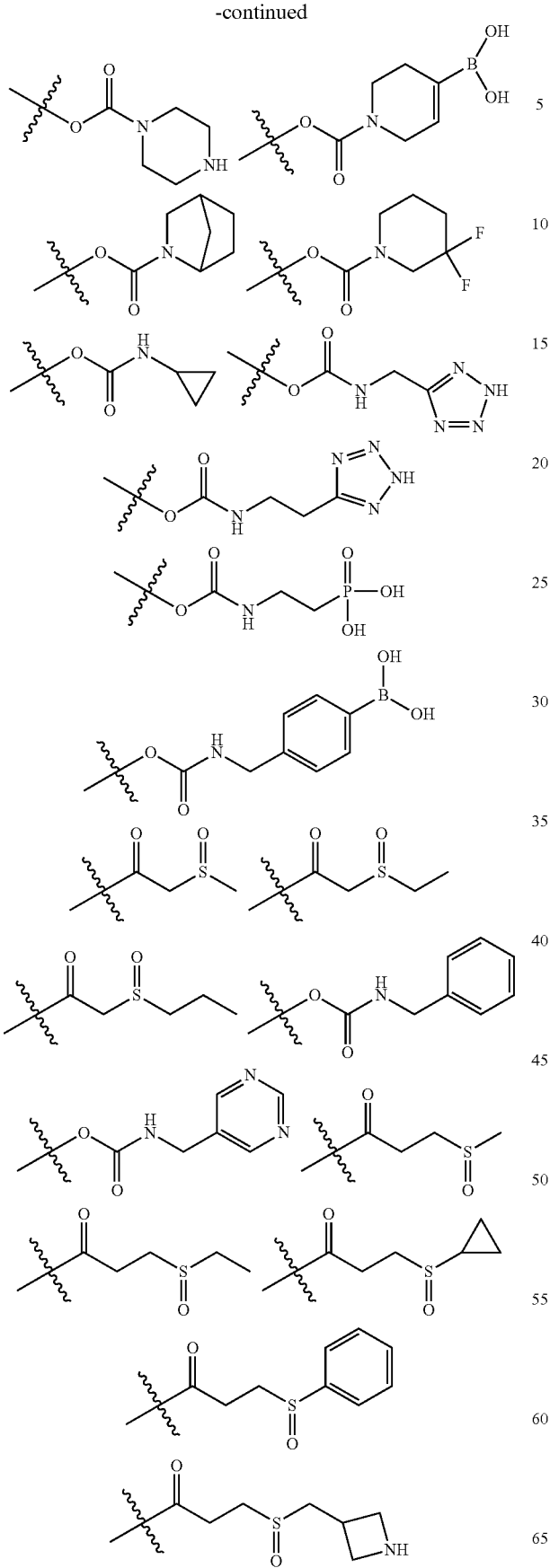
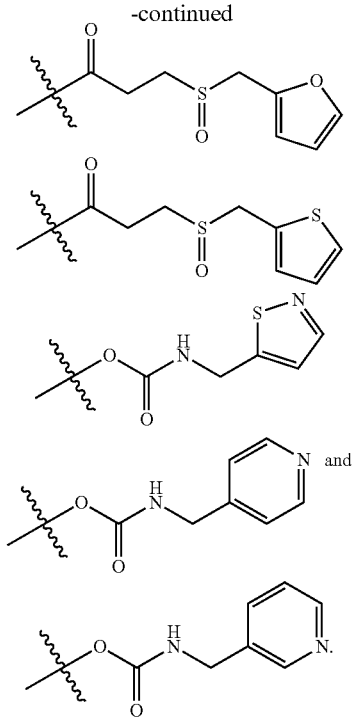

Non-limiting $R^{12}/R^{13}$ Embodiments

In one embodiment, $R^{12}$ is $R^{32}$.

In one embodiment, $R^{13}$ is $R^{32}$.

In one embodiment, $R^{12}$ is $R^{32}$, which is —OC(O)$(CH_2)_{1-4}R^{21}$.

In one embodiment, $R^{12}$ is $R^{32}$, which is —OC(O)$NR^{21}R^{22}$.

In one embodiment, $R^{12}$ is $R^{32}$, which is —OC(O)$NR^{24}R^{25}$.

In one embodiment, $R^{12}$ is $R^{32}$, which is —OC(O)$NR^9(CH_2)_{1-4}P(O)(OR^{21})(OR^{22})$.

In one embodiment, $R^{12}$ is $R^{32}$, which is —C(O)$(CH_2)S(O)R^{21}$.

In one embodiment, $R^{13}$ is $R^{32}$, which is —OC(O)$(CH_2)_{1-4}R^{21}$.

In one embodiment, $R^{13}$ is $R^{32}$, which is —OC(O)$NR^{21}R^{22}$.

In one embodiment, $R^{13}$ is $R^{32}$, which is —OC(O)$NR^{24}R^{25}$.

In one embodiment, $R^{13}$ is $R^{32}$, which is —OC(O)$NR^9(CH_2)_{1-4}P(O)(OR^{21})(OR^{22})$.

In one embodiment, $R^{13}$ is $R^{32}$, which is —C(O)$(CH_2)S(O)R^{21}$.

In one embodiment, $R_{12}$ is —OC(O)($C_{1-6}$alkyl or $C_{3-6}$cycloalkyl)(aryl).

In one embodiment, $R_{12}$ is —OC(O)($C_{1-6}$alkyl or $C_{3-6}$cycloalkyl)(heteroaryl).

In one embodiment, $R_{12}$ is —OC(O)($C_{1-6}$alkyl or $C_{3-6}$cycloalkyl)(heterocycle)

In one embodiment, $R_{12}$ is —OC(O)(heteroaryl).

In one embodiment, $R_{12}$ is —OC(O)(aryl).

In one embodiment, $R_{12}$ is —OC(O)($C_{1-6}$alkyl or $C_{3-6}$cycloalkyl).

In one embodiment, $R_{12}$ is —OC(O)$NR^9(CH_2)_{1-4}P(O)(OR^{21})(OR^{22})$.

In one embodiment, $R_{12}$ is —C(O)($C_{1-6}$alkyl or $C_{3-6}$cycloalkyl)(aryl).

In one embodiment, $R_{12}$ is —C(O)($C_{1-6}$alkyl or $C_{3-6}$cycloalkyl)(heteroaryl).

In one embodiment, $R_{12}$ is —C(O)($C_{1-6}$alkyl or $C_{3-6}$cycloalkyl)(heterocycle).

In one embodiment, $R_{12}$ is —C(O)(heteroaryl).

In one embodiment, $R_{12}$ is —C(O)(heterocycle).

In one embodiment, $R_{12}$ is —C(O)(aryl).

In one embodiment, $R_{12}$ is —C(O)($C_{1-6}$alkyl or $C_{3-6}$cycloalkyl).

In one embodiment, $R_{13}$ is —OC(O)($C_{1-6}$alkyl or $C_{3-6}$cycloalkyl)(aryl).

In one embodiment, $R_{13}$ is —OC(O)($C_{1-6}$alkyl or $C_{3-6}$cycloalkyl)(heteroaryl).

In one embodiment, $R_{13}$ is —OC(O)($C_{1-6}$alkyl or $C_{3-6}$cycloalkyl)(heterocycle)

In one embodiment, $R_{13}$ is —OC(O)(heteroaryl).

In one embodiment, $R_{13}$ is —OC(O)(aryl).

In one embodiment, $R_{13}$ is —OC(O)($C_{1-6}$alkyl or $C_{3-6}$cycloalkyl).

In one embodiment, $R_{13}$ is —OC(O)NR$^9$(CH$_2$)$_{1-4}$P(O)(OR$^{21}$)(OR$^{22}$).

In one embodiment, $R_{13}$ is —C(O)($C_{1-6}$alkyl or $C_{3-6}$cycloalkyl)(aryl).

In one embodiment, $R_{13}$ is —C(O)($C_{1-6}$alkyl or $C_{3-6}$cycloalkyl)(heteroaryl).

In one embodiment, $R_{13}$ is —C(O)($C_{1-6}$alkyl or $C_{3-6}$cycloalkyl)(heterocycle).

In one embodiment, $R_{13}$ is —C(O)(heteroaryl).

In one embodiment, $R_{13}$ is —C(O)(heterocycle).

In one embodiment, $R_{13}$ is —C(O)(aryl).

In one embodiment, $R_{13}$ is —C(O)($C_{1-6}$alkyl or $C_{3-6}$cycloalkyl).

In one embodiment, the disclosure provides compounds of Formula I, wherein; one of $R^{12}$ and $R^{13}$ is H and the other of $R^{12}$ and $R^{13}$ is $R^{32}$, where $R^{32}$ is chosen from —OC(O)(CH$_2$)$_{1-4}$R$^{21}$, —OC(O)NR$^{21}$R$^{22}$, —OC(O)NR$^{24}$R$^{25}$, —OC(O)NR$^9$(CH$_2$)$_{1-4}$P(O)(OR$^{21}$)(OR$^{22}$), and —C(O)(CH$_2$)S(O)R$^{21}$, each of which is optionally substituted;

wherein R$^9$, R$^{21}$, R$^{22}$, R$^{24}$, and R$^{25}$ are as defined in the summary section above.

In another embodiment, the disclosure provides compounds of Formula I, wherein;

$R^1$, $R^{1'}$, $R^2$, and $R^{3'}$ are all hydrogen;

$R^{2'}$ is fluoro and $R^3$ is hydrogen, —C$_0$-C$_4$alkyl(C$_3$-C$_7$cycloalkyl), or —O—C$_0$-C$_4$alkyl(C$_3$-C$_7$cycloalkyl);

$R^5$ is hydrogen, halogen, or C$_1$-C$_2$alkyl;

$R^{11}$, $R^{13}$, and $R^{14}$, and $R^{15}$ if present, are independently chosen at each occurrence from hydrogen, halogen, hydroxyl, amino, C$_1$-C$_4$alkyl, C$_1$-C$_4$alkoxy, —C$_0$-C$_2$alkyl(mono- and di-C$_1$-C$_2$alkylamino), trifluoromethyl, and trifluoromethoxy;

$X^{12}$ is CR$^{12}$; and $R^{12}$ is chosen from —OC(O)(CH$_2$)$_{1-4}$R$^{21}$, —OC(O)NR$^{21}$R$^{22}$, —OC(O)NR$^{24}$R$^{25}$, —OC(O)NR$^9$(CH$_2$)$_{1-4}$P(O)(OR$^{21}$)(OR$^{22}$), and —C(O)(CH$_2$)S(O)R$^{21}$, each of which is optionally substituted;

wherein R$^9$, R$^{21}$, R$^{22}$, R$^{24}$, and R$^{25}$ are as defined in the summary section above.

In one embodiment, the disclosure provides compounds of Formula I, wherein;

m is 0 or 1;

$R^2$ is halogen, $R^{2'}$ is hydrogen or halogen, and $R^3$ is hydrogen, halogen, —C$_0$-C$_4$alkyl(C$_3$-C$_7$cycloalkyl), or —O—C$_0$-C$_4$alkyl(C$_3$-C$_7$cycloalkyl);

$R^6$ is —C(O)C$_1$-C$_4$alkyl, —C(O)NH$_2$, —C(O)CF$_3$, —C(O)(C$_3$-C$_7$cycloalkyl), or -ethyl(cyanoimino);

one of $R^{12}$ and $R^{13}$ is selected from hydrogen, halogen, C$_1$-C$_4$alkyl, C$_1$-C$_4$alkoxy, trifluoromethyl, and trifluoromethoxy; the other of $R^{12}$ and $R^{13}$ is $R^{32}$, where $R^{32}$ is chosen from —OC(O)(CH$_2$)$_{1-4}$R$^{21}$, —OC(O)NR$^{21}$R$^{22}$, —OC(O)NR$^{24}$R$^{25}$, —OC(O)NR$^9$(CH$_2$)$_{1-4}$P(O)(OR$^{21}$)(OR$^{22}$), and —C(O)(CH$_2$)S(O)R$^{21}$, each of which is optionally substituted;

wherein R$^9$, R$^{21}$, R$^{22}$, R$^{24}$, and R$^{25}$ are as defined in the summary section above.

In one embodiment, the disclosure provides compounds of Formula I, wherein;

one of $R^{12}$ and $R^{13}$ is hydrogen, hydroxyl, halogen, methyl, or methoxy; and the other of $R^{12}$ and $R^{13}$ is $R^{32}$, where $R^{32}$ is chosen from —OC(O)(CH$_2$)$_{1-4}$R$^{21}$, —OC(O)NR$^{21}$R$^{22}$, —OC(O)NR$^{24}$R$^{25}$, —OC(O)NR$^9$(CH$_2$)$_{1-4}$P(O)(OR$^{21}$)(OR$^{22}$), and —C(O)(CH$_2$)S(O)R$^{21}$, each of which is optionally substituted;

wherein R$^9$, R$^{21}$, R$^{22}$, R$^{24}$, and R$^{25}$ are as defined in the summary section above.

In one embodiment, $R^{32}$ may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, C$_1$-C$_6$alkyl, C$_1$-C$_6$alkoxy, —C$_0$-C$_2$alkyl(mono- and di-C$_1$-C$_4$alkylamino), C$_1$-C$_6$alkylester, C$_1$-C$_4$alkylamino, C$_1$-C$_4$hydroxylalkyl, C$_1$-C$_2$haloalkyl, and C$_1$-C$_2$haloalkoxy.

Central Core Moiety

The central core moiety in Formula I is illustrated below:

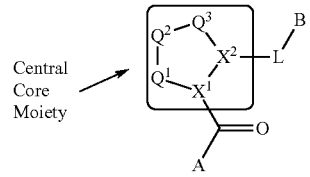

wherein:

$Q^1$ is N(R$^1$) or C(R$^1$R$^{1'}$);

$Q^2$ is C(R$^2$R$^{2'}$), C(R$^2$R$^{2'}$)—C(R$^2$R$^{2'}$), S, O, N(R$^1$) or C(R$^2$R$^{2'}$)O;Q3 is N(R3), S, or C(R3R3');

$X^1$ and $X^2$ are independently N, CH, or CZ, or $X^1$ and $X^2$ together are C=C; and wherein $Q^1$, $Q^2$, $Q^3$, $X^1$, and $X^2$ are selected such that a stable compound results.

Non-limiting examples of the

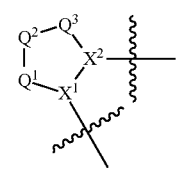

ring are illustrated below (any of which can be otherwise substituted with R$^1$, R$^{1'}$, R$^2$, R$^{2'}$, R$^3$ and R$^{3'}$) as described in more detail below.

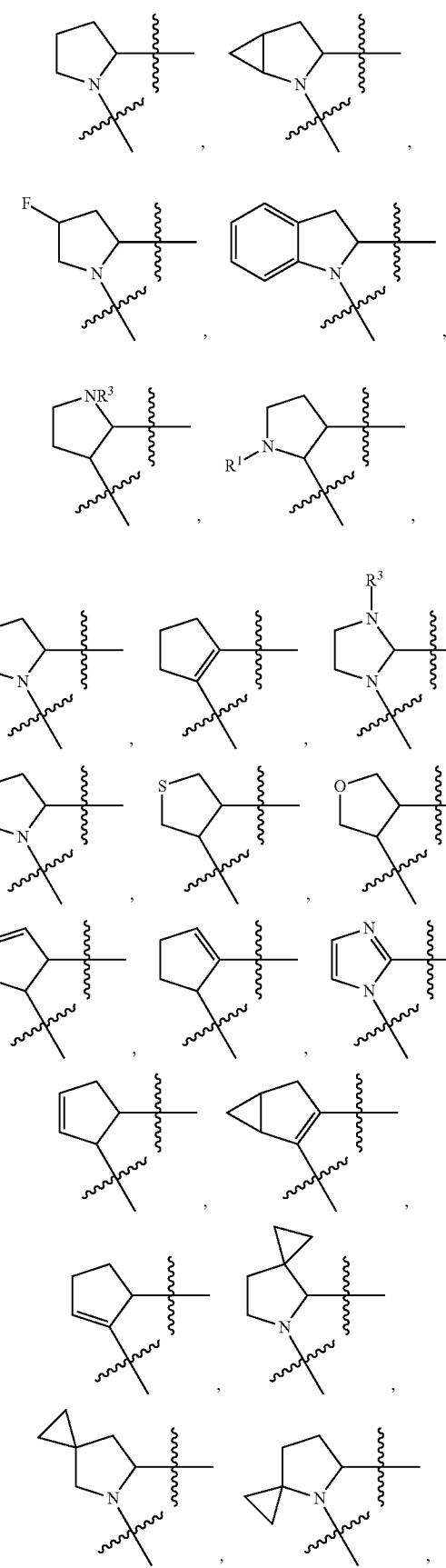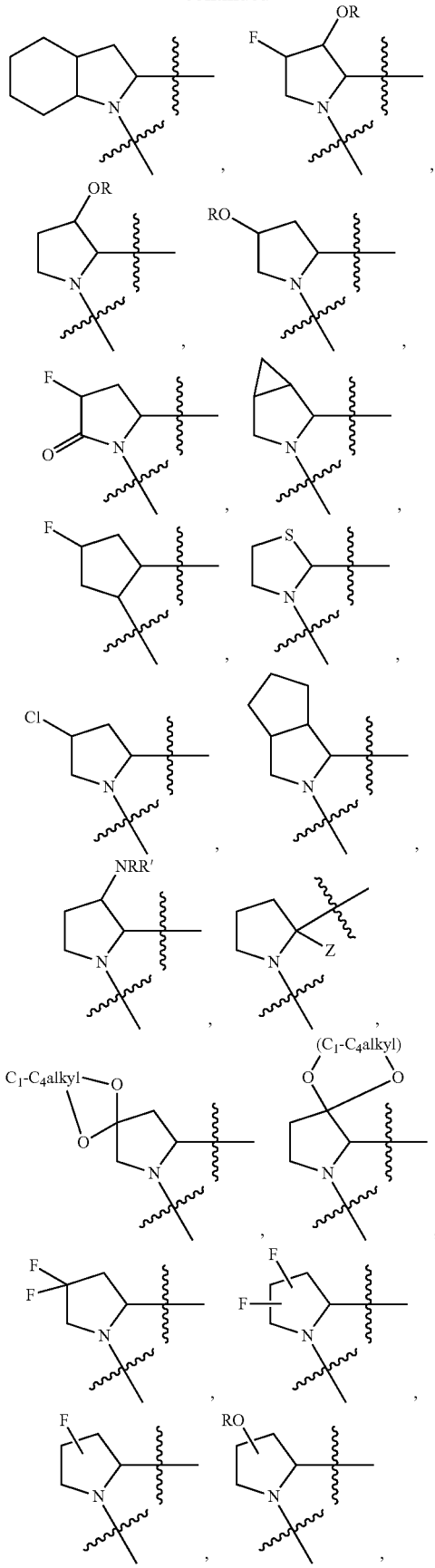

-continued

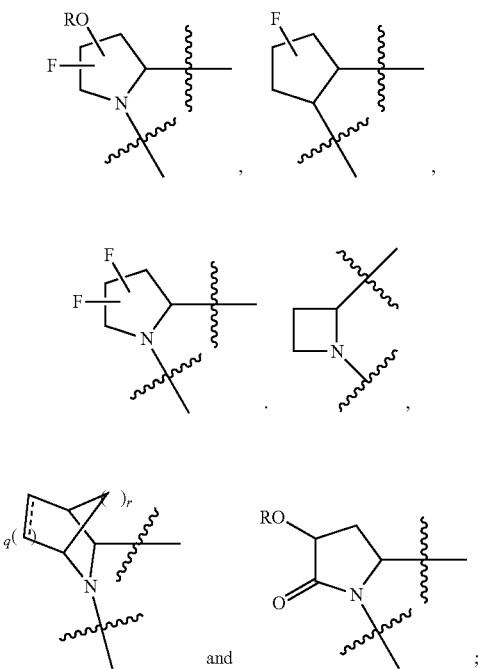

wherein q is 0, 1, 2 or 3 and r is 1, 2 or 3.

R and R' are independently chosen from H, alkyl, cycloalkyl, cycloalkylalkyl, heterocycle, heterocycloalkyl, aryl, aralkyl, heteroaryl, heteroarylalkyl wherein each group can be optionally substituted or any other substituent group herein that provides the desired properties. In some embodiments, the ring includes one or more chiral carbon atoms. The invention includes embodiments in which the chiral carbon can be provided as an enantiomer, or mixtrues of enantiomers, including a racemic mixture. Where the ring includes more than one stereocenter, all of the enantiomers and diastereomers are included in the invention as individual species.

Z is F, Cl, $NH_2$, $CH_3$, $CH_2D$, $CHD_2$, or $CD_3$.

$R^1$, $R^{1'}$, $R^2$, $R^{2'}$, $R^3$, and $R^{3'}$ are independently chosen at each occurrence, as appropriate, and only where a stable compound results, from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkyl$NR^9R^{10}$, —C(O)$OR^9$, —OC(O)$R^9$, —$NR^9$C(O)$R^{10}$, —C(O)$NR^9R^{10}$, —OC(O)$NR^9R^{10}$, —$NR^9$C(O)$OR^{10}$, $C_1$-$C_2$haloalkyl, and $C_1$-$C_2$haloalkoxy, where $R^9$ and $R^{10}$ are independently chosen at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl).

Non-limiting Central Core Embodiments

In alternative embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently chosen from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which ring may be unsubstituted or substituted with 1 or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di—$C_1$-$C_4$alkylamino)$C_0$-$C_4$alkyl, —$C_0$-$C_4$alkyl($C_3$-$C_7$cycloalkyl), - O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^2$ may be taken together to form a 3-membered carbocyclic ring; $R^1$ and $R^2$ may be taken together to form a 4- to 6-membered carbocyclic or aryl ring or a 4- to 6-membered heterocyclic or heteroaryl ring containing 1 or 2 heteroatoms independently chosen from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring; each of which ring may be unsubstituted or substituted with 1 or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di—$C_1$-$C_4$alkylamino)$C_0$-$C_4$alkyl, —$C_0$-$C_4$alkyl($C_3$-C7cycloalkyl), —O—$C_0$-$C_4$alkyl($C_3$-$C_7$cycloalkyl), $C_1$-$C_2$haloalkyl, and $C_1$-$C_2$haloalkoxy.

In one embodiment, the central core moiety is proline.

In one embodiment, the central core moiety is 4-fluoro-proline.

In one embodiment, $R^1$, $R^{1'}$, $R^{2'}$, $R^3$ and $R^{3'}$, if present, are all hydrogen; and $R^2$ is fluoro.

In one embodiment, $R^1$, $R^{1'}$, $R^{2'}$, and $R^{3'}$, if present, are all hydrogen; and $R^2$ is fluoro and $R^3$ is —$C_0$-$C_4$alkyl($C_3$-$C_7$cycloalkyl) or —O—$C_0$-$C_4$alkyl($C_3$-$C_7$cycloalkyl).

In one embodiment, $R^1$ and $R^2$ are taken together to form a 3- to 6-membered cycloalkyl group, and $R^{1'}$, $R^{2'}$, $R^3$, and $R^{3'}$, where present, are all hydrogen.

In one embodiment, $R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

In one embodiment, $R^1$ is hydrogen and $R^2$ is fluoro.

In one embodiment, $R^1$ and $R^2$ are joined to form a 3 membered ring.

The disclosure includes compounds of Formula I in which the central pyrrolidine is vinyl substituted, for example:

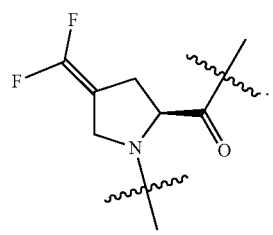 [SMILES: *C(=O)[C@@H]1CC(=C(F)F)CN1*]

In one embodiment, the compound of Formula I has the structure:

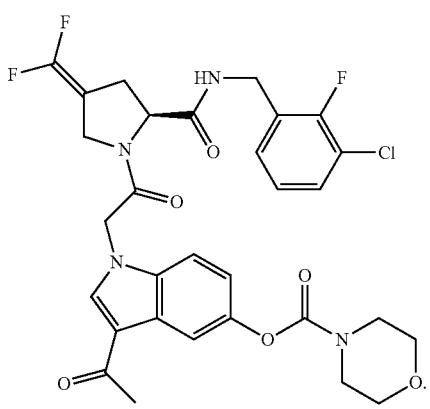 [SMILES: CC(=O)c1cn(CC(=O)N2CC(=C(F)F)C[C@H]2C(=O)NCc2cccc(Cl)c2F)c2ccc(OC(=O)N3CCOCC3)cc12]

In one embodiment, the central pyrrolidine is modified by addition of a second heteroatom to a pyrrolidine ring, such as N, O, S, or Si, for example:

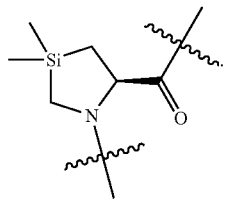 [SMILES: *C(=O)[C@@H]1C[Si](C)(C)CN1*]

Another modification within the scope of the disclosure is joining a substituent on the central pyrrolidine ring to $R^7$ or $R^8$ to form a 5- to 6- membered heterocyclic ring, for example:

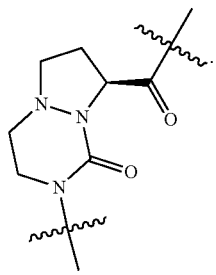 [SMILES: *C(=O)[C@@H]1CCN2CCN(*)C(=O)N12]

Example compounds having the modifications disclosed above include:

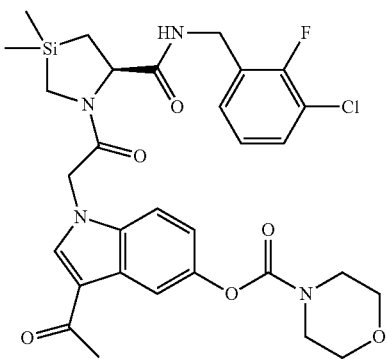

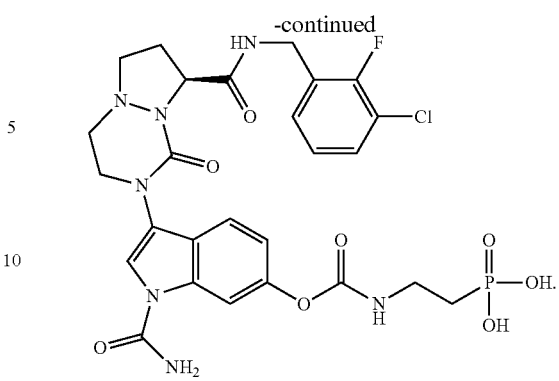

Central Core L-B Substituents

The central core L-B substituents in Formula I are illustrated below:

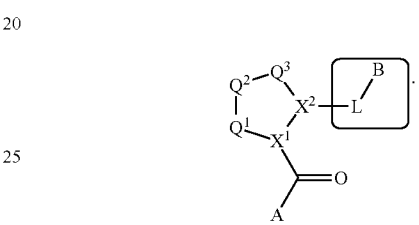

L is a bond or is chosen from the formulas:

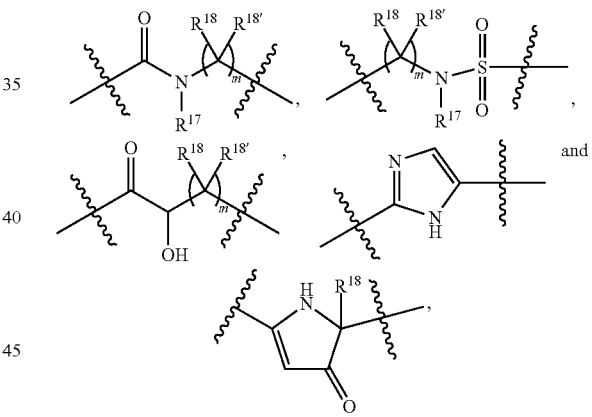

where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently chosen from hydrogen, halogen, hydroxymethyl, and methyl; and m is 0, 1, 2, or 3.

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl).

Each of which B is unsubstituted or substituted with one or more substituents independently chosen from $R^{33}$ and $R^{34}$, and 0 or 1 substituents chosen from $R^{35}$ and $R^{36}$:

$R^{33}$ is independently chosen from halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy;

R³⁴ is independently chosen from nitro, $C_2$-$C_6$alkenyl, $C_2$-$C_6$alkynyl, $C_1$-$C_6$thioalkyl, —J$C_3$-$C_7$cycloalkyl, —B(OH)₂, —JC(O)NR⁹R²³, —JOSO₂OR²¹, —C(O)(CH₂)₁₋₄S(O)R²¹, —O(CH₂)₁₋₄S(O)NR²¹R²², —JOP(O)(OR²¹)(OR²²), —JP(O)(OR²¹)(OR²²), —JOP(O)(OR²¹)R²², —JP(O)(OR²¹)R²², —JOP(O)R²¹R²², —JP(O)R²¹R²², —JSP(O)(OR²¹)(OR²²), —JSP(O)(OR²¹)(R²²), —JSP(O)(R²¹)(R²²), —JNR⁹P(O)(NHR²¹)(NHR²²), —JNR⁹P(O)(OR²¹)(NHR²²), —JNR⁹P(O)(OR²¹)(OR²²), —JC(S)R²¹, —JNR²¹SO₂R²², —JNR⁹S(O)NR¹⁰R²², —JNR⁹SO₂NR¹⁰R²², —JSO₂NR⁹COR²², —JSO₂NR⁹CONR²¹R²², —JNR²¹SO₂R²², —JC(O)NR²¹SO₂R²², —JC(NH₂)NR²², —JC(NH₂)NR⁹S(O)₂R²², —JOC(O)NR²¹R²², —JNR²¹C(O)OR²², —JNR²¹OC(O)R²², —(CH₂)₁₋₄C(O)NR²¹R²², —JC(O)R²⁴R²⁵, —JNR⁹C(O)R²¹, —JC(O)R²¹, —JNR⁹C(O)NR¹⁰R²², —CCR²¹, —(CH₂)₁₋₄OC(O)R²¹, and —JC(O)OR²³; each of which R³⁴ may be unsubstituted or substituted with one or more substituents independently chosen from halogen, hydroxyl, nitro, cyano, amino, oxo, —B(OH)₂, —Si(CH₃)₃, —COOH, —CONH₂, —P(O)(OH)₂, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di—$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy;

R³⁵ is independently chosen from naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7-ring atoms in each ring; each of which R³⁵ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO₂R⁹, $C_1$-$C_2$haloalkyl, and $C_1$-$C_2$haloalkoxy; and R³⁶ is independently chosen from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which R³⁶ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO₂R⁹, —OSi(CH₃)₂C(CH₃)₃, —Si(CH₃)₂C(CH₃)₃, $C_1$-$C_2$haloalkyl, and $C_1$-$C_2$haloalkoxy.

J is independently chosen at each occurrence from a covalent bond, $C_1$-$C_4$alkylene, —O$C_1$-$C_4$alkylene, $C_2$-$C_4$alkenylene, and $C_2$-$C_4$alkynylene.

In one embodiment, —L-B— is

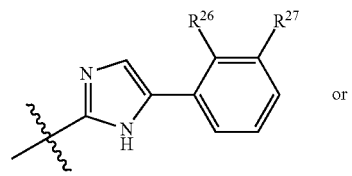

or

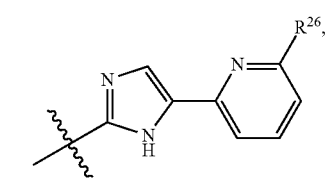

where

R²⁶ and R²⁷ are independently chosen from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl (mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, $C_1$-$C_2$haloalkoxy, and $C_1$-$C_2$haloalkylthio.

Non-Limiting L-B Embodiments

In another embodiment, —L-B— is

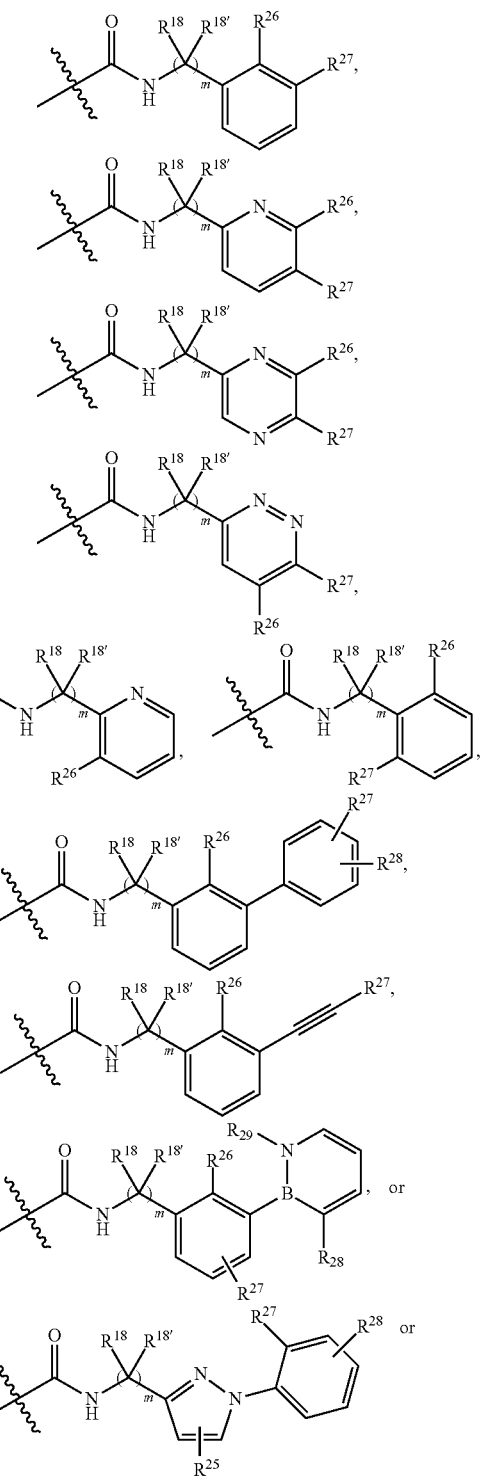

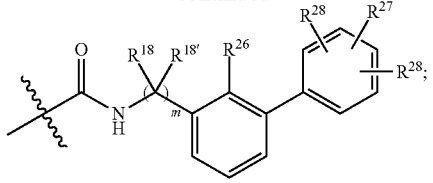

wherein
R$^{18}$ and R$^{18'}$ are independently chosen from hydrogen, halogen, hydroxymethyl, and methyl; and m is 0 or 1; and R$^{26}$, R$^{27}$, and R$^{28}$ are independently chosen from hydrogen, halogen, hydroxyl, nitro, cyano, C$_1$-C$_6$alkyl, C$_2$-C$_6$alkenyl, C$_2$-C$_6$alkanoyl, C$_1$-C$_6$alkoxy, C$_1$-C$_6$thioalkyl, (mono- and di-C$_1$-C$_6$alkylamino)C$_0$-C$_4$alkyl, (C$_3$-C$_7$cycloalkyl)C$_0$-C$_4$alkyl, (aryl)C$_0$-C$_4$alkyl-, (heteroaryl)C$_0$-C$_4$alkyl-, and —C$_0$-C$_4$alkoxy(C$_3$-C$_7$cycloalkyl); each of which R$^{26}$, R$^{27}$, and R$^{28}$ other than hydrogen, halogen, hydroxyl, nitro, cyano, is unsubstituted or substituted with one or more substituents independently chosen from halogen, hydroxyl, amino, C$_1$-C$_2$alkoxy, C$_1$-C$_2$haloalkyl, (C$_3$-C7cycloalkyl)C$_0$-C$_4$alkyl-, and C$_1$-C$_2$haloalkoxy; and R$^{29}$ is hydrogen, C$_1$-C$_2$alkyl, C$_1$C$_2$haloalkyl or —Si(CH$_3$)$_2$C(CH$_3$)$_3$.

In one embodiment, m is 0.

In one embodiment, the disclosure further includes compounds and salts of Formula I in which B is 2-fluoro-3-chlorophenyl. In another embodiment, another carbocyclic, aryl, heterocyclic, or heteroaryl group such as 2-bromo-pyridin-6-yl, 1-(2,2,2-trifluoroethyl)-1H-pyrazol-3-yl, 2,2-dichlorocyclopropylmethyl, or 2-fluoro-3-trimethylsilylphenyl is used.

In another embodiment, B is phenyl, pyridyl, or indanyl each of which is unsubstituted or substituted with one or more substituents independently chosen from hydrogen, halogen, hydroxyl, nitro, cyano, C$_1$-C$_6$alkyl, C$_2$-C$_6$alkenyl, C$_2$-C$_6$alkanoyl, C$_1$-C$_6$alkoxy, C$_1$-C$_6$thioalkyl, (mono- and di-C$_1$-C$_6$alkylamino)C$_0$-C$_4$alkyl, (C$_3$-C$_7$cycloalkyl)C$_0$-C$_4$alkyl, —C$_0$-C$_4$alkoxy(C$_3$-C$_7$cycloalkyl), (phenyl)C$_0$-C$_2$alkyl, (pyridyl)C$_0$-C$_2$alkyl; each of which substituents other than hydrogen, halogen, hydroxyl, nitro, cyano, is unsubstituted or substituted with one or more substituents independently chosen from halogen, hydroxyl, amino, C$_1$-C$_2$alkyl, C$_1$-C$_2$alkoxy, —OSi(CH$_3$)$_2$C(CH$_3$)$_3$, —Si(CH$_3$)$_2$C(CH$_3$)$_3$, C$_1$-C$_2$haloalkyl, and C$_1$-C$_2$haloalkoxy.

In another embodiment, B is phenyl or pyridyl substituted with 1, 2, or 3 substituents chosen from chloro, bromo, hydroxyl, —SCF$_3$, C$_1$-C$_2$alkyl, C$_1$-C$_2$alkoxy, trifluoromethyl, phenyl and trifluoromethoxy each of which substituents other than chloro, bromo, hydroxyl, —SCF$_3$, can be optionally substitued.

In certain embodiments, B is a 2-fluoro-3-chlorophenyl or a 2-fluoro-3-trifluoromethoxyphenyl group.

In one embodiment, B is pyridyl, optionally substituted with halogen, C$_1$-C$_2$alkoxy, and trifluoromethyl.

In one embodiment, B is phenyl, substituted with 1, 2, or 3 substituents independently selected from halogen, C$_1$-C$_2$alkyl, C$_1$-C$_2$alkoxy, trifluoromethyl, and optionally substituted phenyl.

In one embodiment, R$^{23}$ is independently chosen at each occurrence from (C$_3$-C7cycloalkyl)C$_0$-C$_4$alkyl, (phenyl)C$_0$-C$_4$alkyl, (4- to 7-membered heterocycloalkyl)C$_0$-C$_4$alkyl having 1, 2, or 3 heteroatoms independently chosen from N, O, and S, and (5- or 6-membered unsaturated or aromatic heterocycle)C$_0$-C$_4$alkyl having 1, 2, or 3 heteroatoms independently chosen from N, O, and S.

In one embodiment, B is selected from

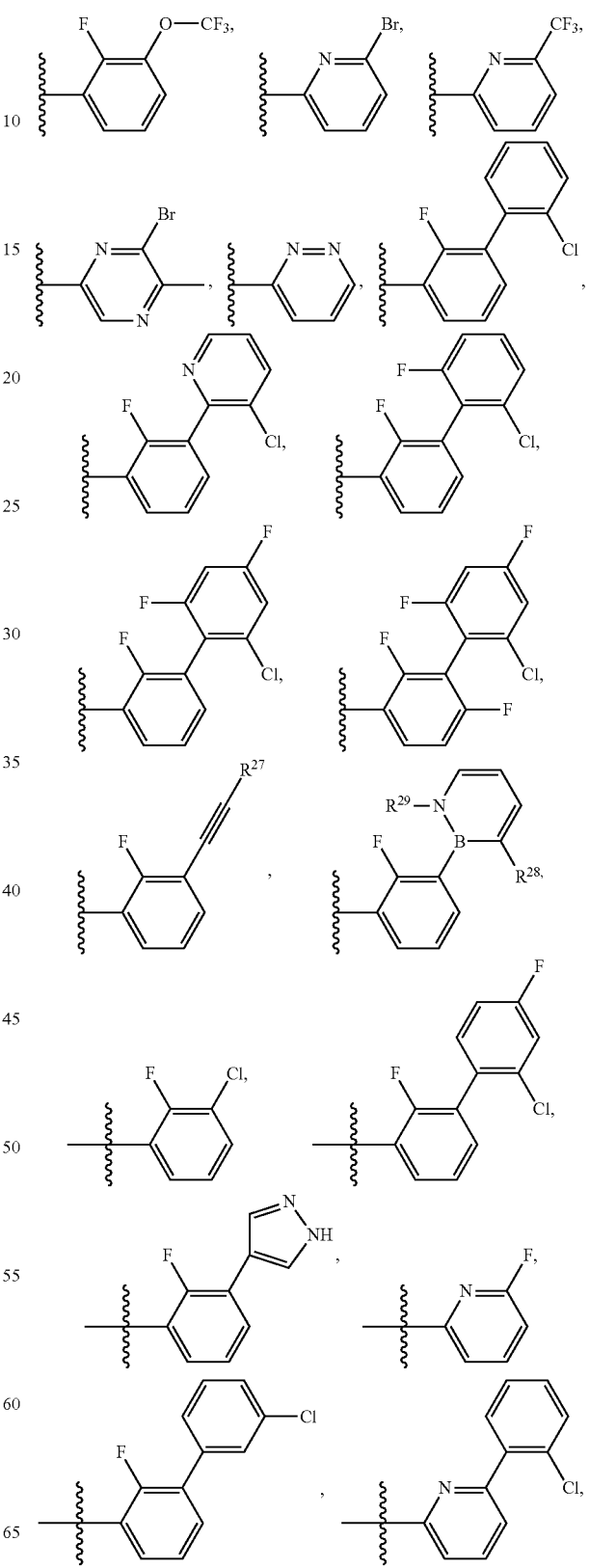

-continued
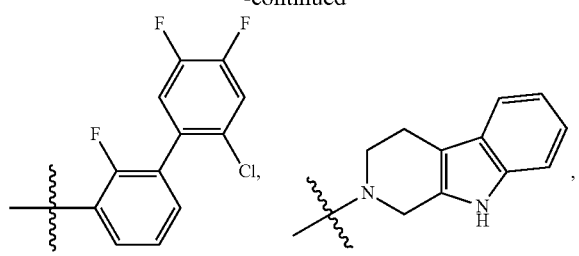
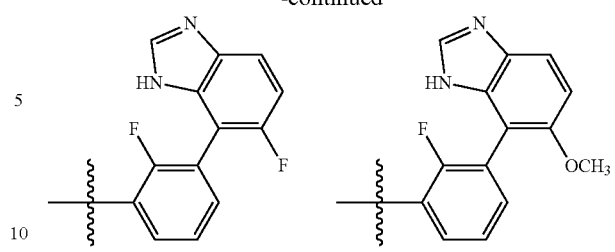
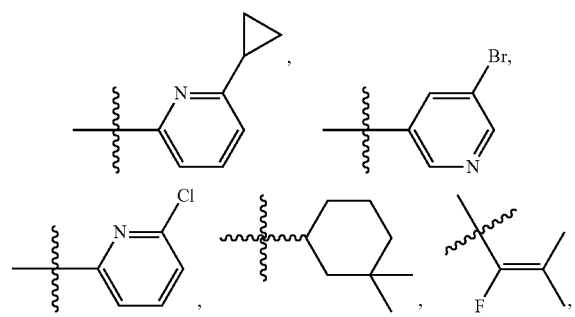
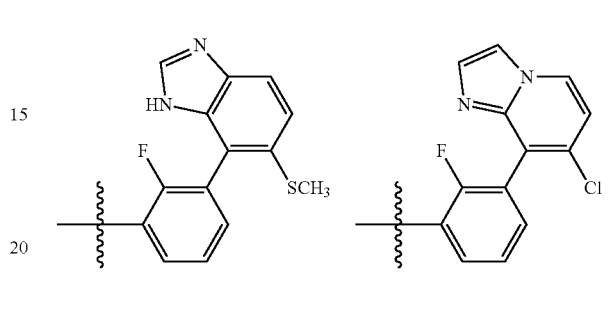
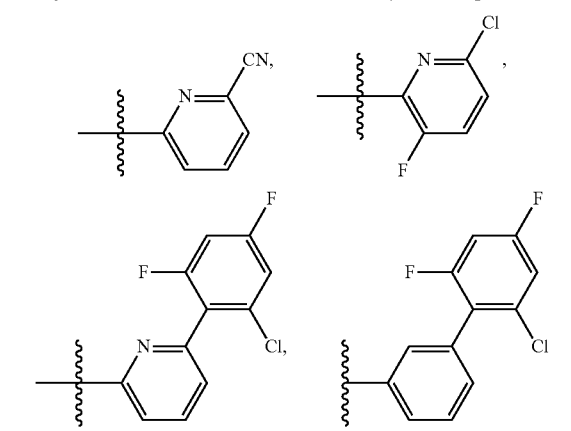
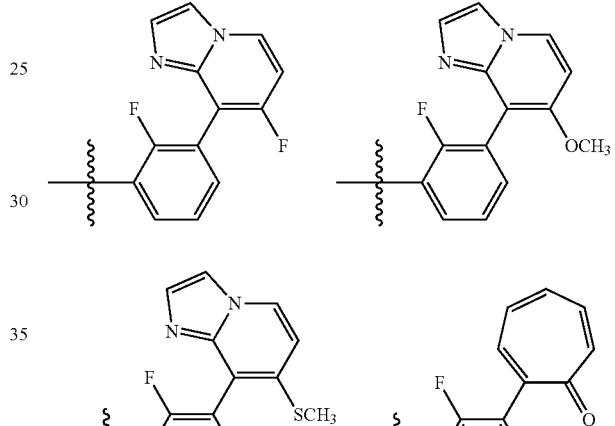
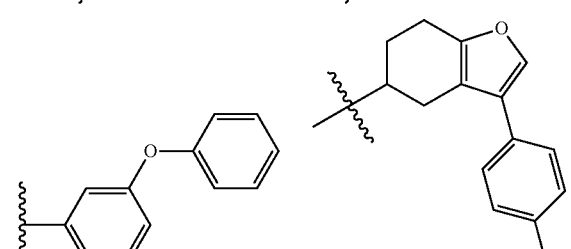
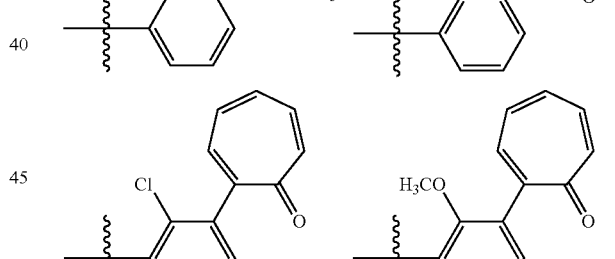
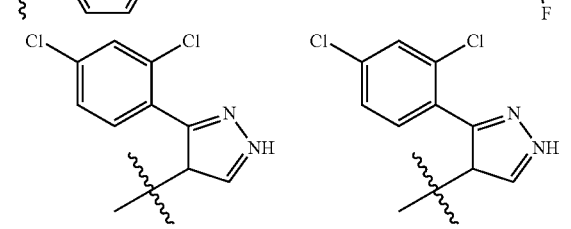
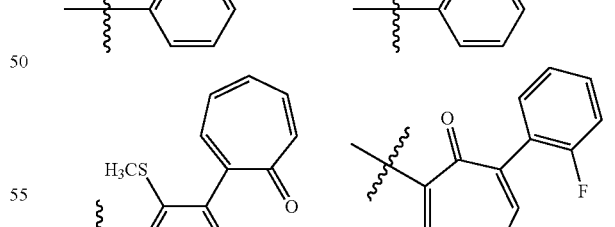
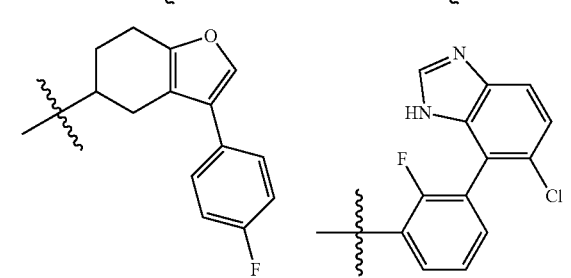
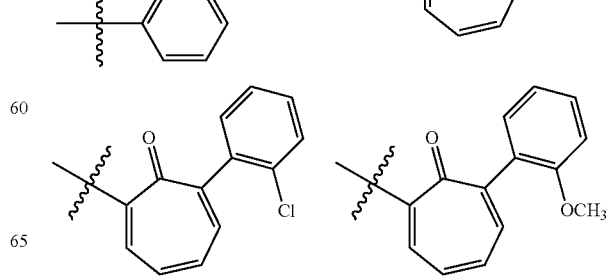

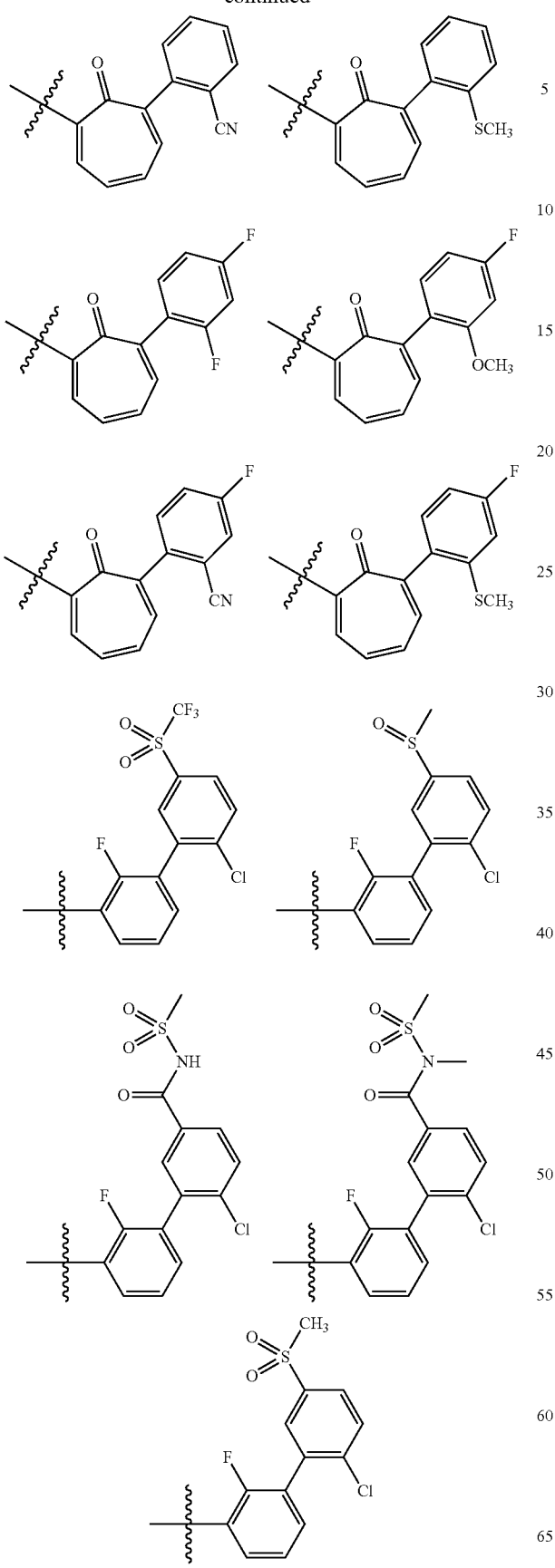
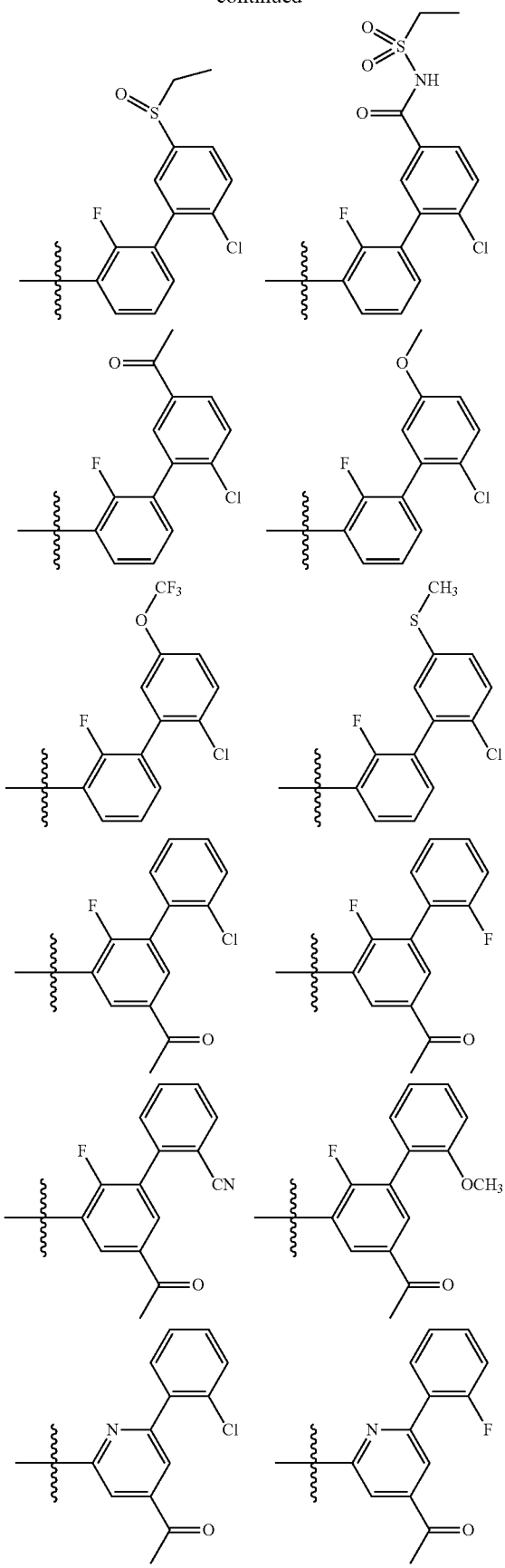

-continued
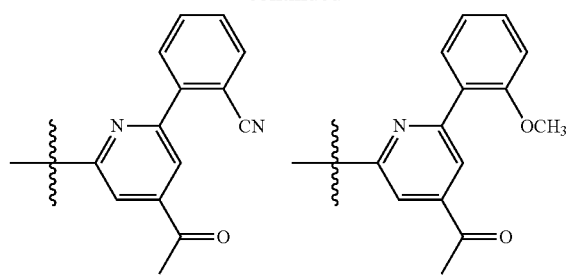
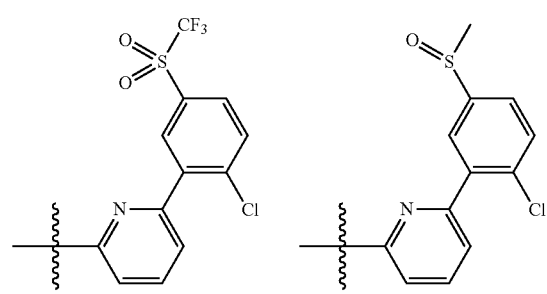
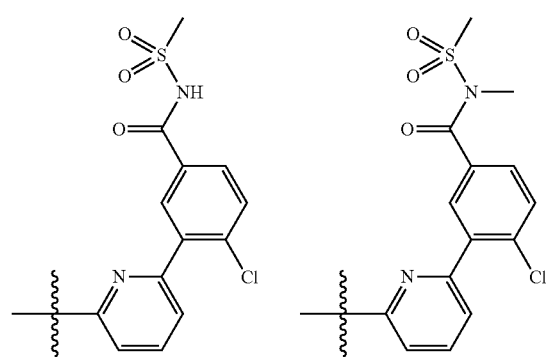
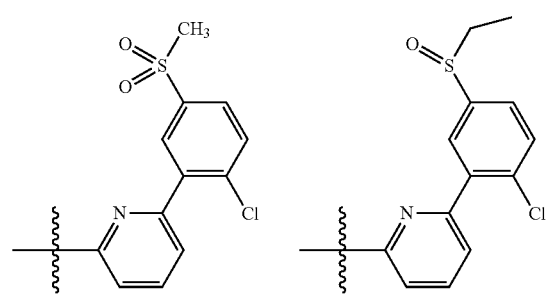
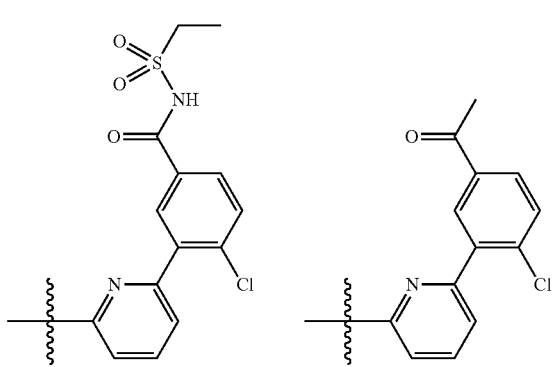
-continued
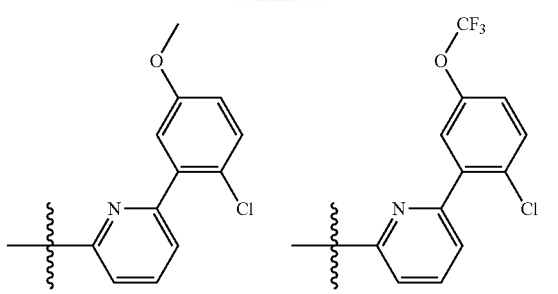
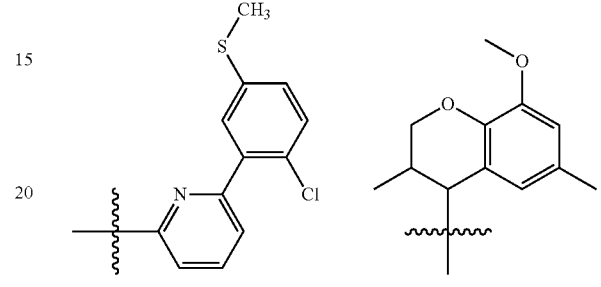
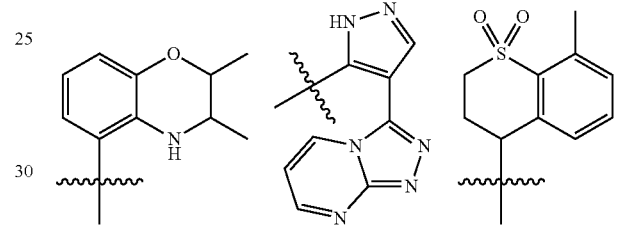
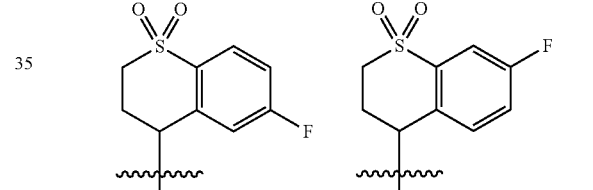
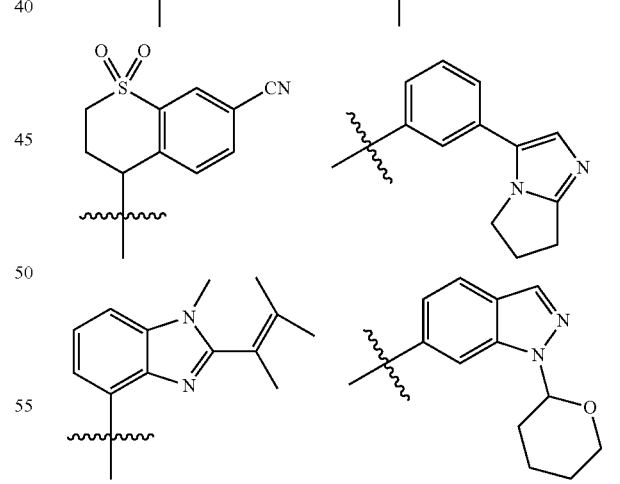
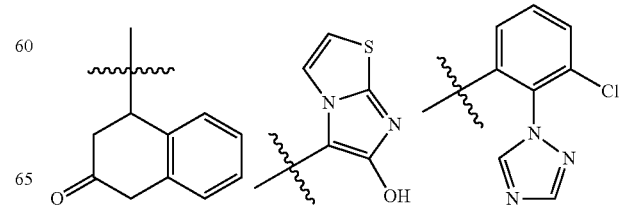

51
-continued
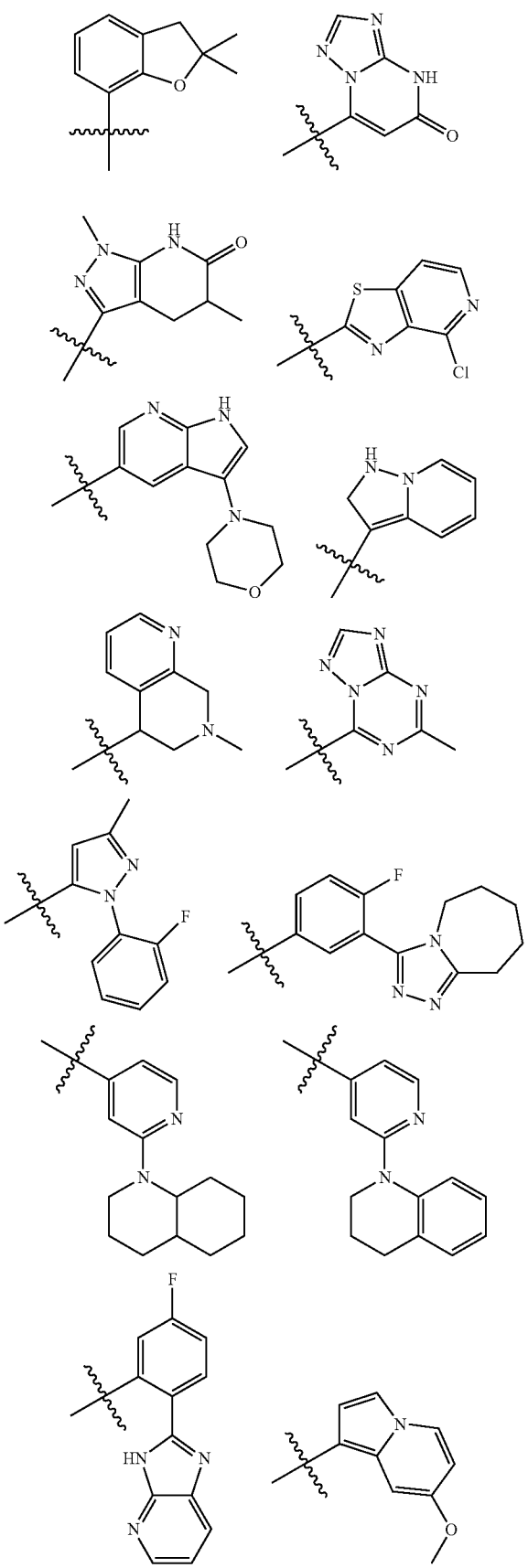
52
-continued
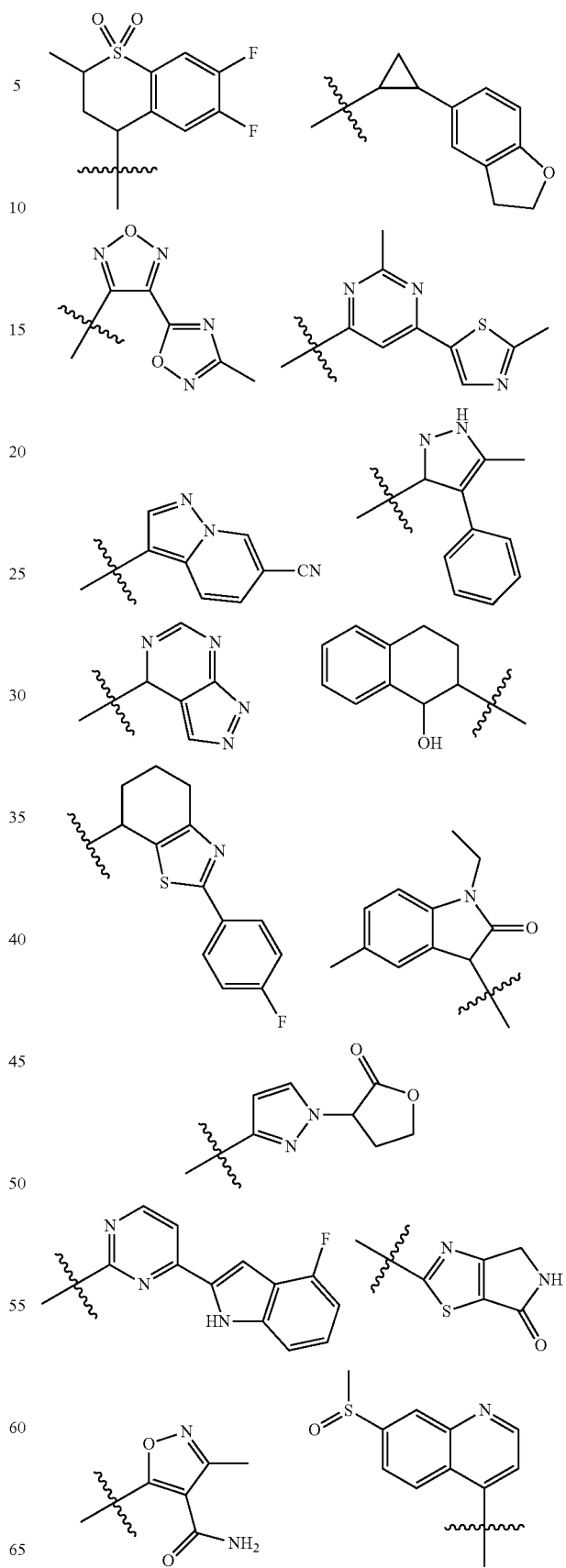

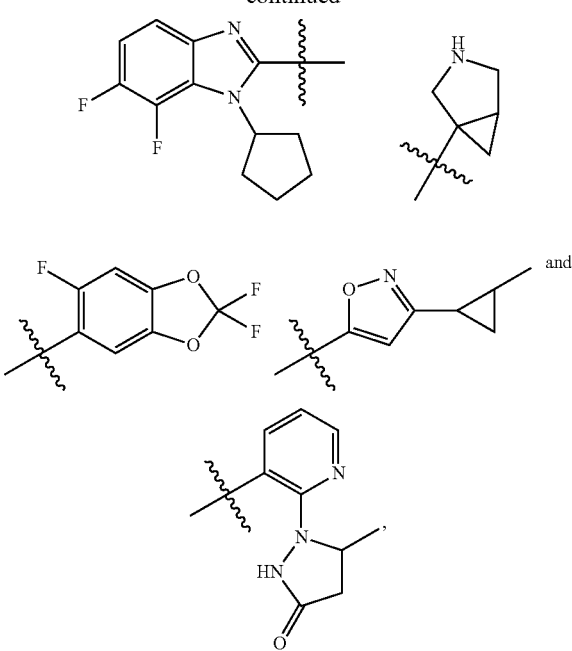
where $R^{27}$ is hydrogen, methyl, or trifluoromethyl; $R^{28}$ is hydrogen or halogen; and $R^{29}$ is hydrogen, methyl, trifluoromethyl, or —Si(CH$_3$)$_2$C(CH$_3$)$_3$.
Central Core (C=O)A Substituent
The central core (C=O)A substituent in Formula I is illustrated below:
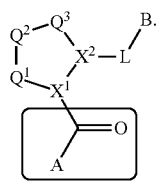
A is a group chosen from:
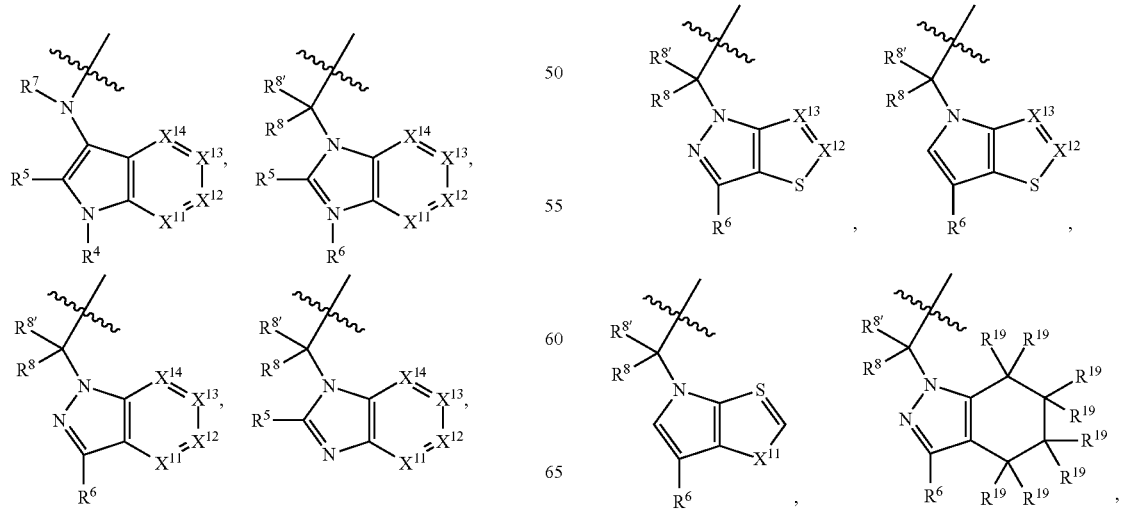

-continued

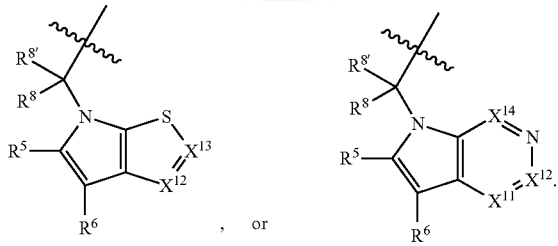

R⁴ is chosen from —CHO, —CONH₂, C₂-C₆alkanoyl, hydrogen, —SO₂NH₂, —C(CH₂)₂F, —CH(CF₃)NH₂, C₁-C₆alkyl, —C₀-C₄alkyl(C₃-C₇cycloalkyl), —C(O)C₀-C₂alkyl(C₃-C₇cycloalkyl),

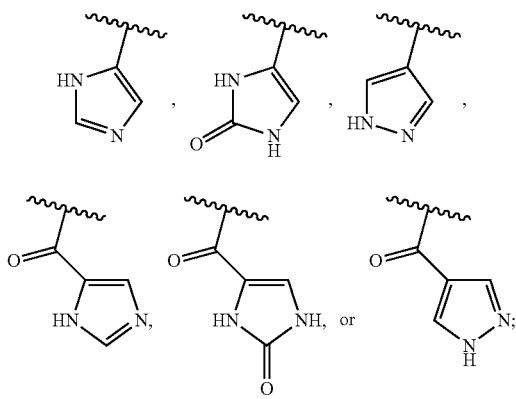

each of which R⁴ other than hydrogen, —CHO, and —CONH₂, is unsubstituted or substituted with one or more of amino, imino, halogen, hydroxyl, cyano, cyanoimino, C₁-C₂alkyl, C₁-C₂alkoxy, —C₀-C₂alkyl(mono- and di—C₁-C₄alkylamino), C₁-C₂haloalkyl, and C₁-C₂haloalkoxy.

R⁵ and R⁶ are independently chosen from —CHO, —C(O)NH₂, —C(O)NH(CH₃), C₂-C₆alkanoyl, hydrogen, hydroxyl, halogen, cyano, nitro, —COOH, —SO₂NH₂, vinyl, C₁-C₆alkyl (including methyl), C₂-C₆alkenyl, C₁-C₆alkoxy, —C₀-C₄alkyl(C₃-C₇cycloalkyl), —C(O)C₀-C₄alkyl(C₃-C₇cycloalkyl), —P(O)(OR⁹)₂, —OC(O)R⁹, —C(O)OR⁹, —C(O)N(CH₂CH₂R⁹)(R¹⁰), —NR⁹C(O)R¹⁰, phenyl, or 5- to 6-membered heteroaryl.

Each R⁵ and R⁶ other than hydrogen, hydroxyl, cyano, and —COOH is unsubstituted or optionally substituted. For example, R⁵ and R⁶ other than hydrogen, hydroxyl, cyano, and —COOH may be substituted with one or more substituents independently chosen from halogen, hydroxyl, amino, imino, cyano, cyanoimino, C₁-C₂alkyl, C₁-C₄alkoxy, —C₀-C₂alkyl(mono- and di-C₁-C₄alkylamino), C₁-C₂haloalkyl, and C₁-C₂haloalkoxy.

R⁶' is hydrogen, halogen, hydroxyl, C₁-C₄alkyl, —C₀-C₄alkyl(C₃-C₇cycloalkyl), or C₁-C₄alkoxy; or R⁶ and R⁶' may be taken together to form an oxo, vinyl, or imino group.

R⁷ is hydrogen, C₁-C₆alkyl, or —C₀-C₄alkyl(C₃-C₇cycloalkyl).

R⁸ and R⁸' are independently chosen from hydrogen, halogen, hydroxyl, C₁-C₆alkyl, —C₀-C₄alkyl(C₃-C₇cycloalkyl), C₁-C₆alkoxy, and (C₁-C₄alkylamino)C₀-C₂alkyl; or R⁸ and R⁸' are taken together to form an oxo group; or R⁸ and R⁸' can be taken together with the carbon that they are bonded to form a 3-membered carbocyclic ring.

R¹⁶ is absent or may include one or more substituents independently chosen from halogen, hydroxyl, nitro, cyano, C₁-C₆alkyl, C₂-C₆alkenyl, C₂-C₆alkanoyl, C₁-C₆alkoxy, —C₀-C₄alkyl(mono- and di-C₁-C₆alkylamino), —C₀-C₄alkyl(C₃-C₇cycloalkyl), C₁-C₂haloalkyl, and C₁-C₂haloalkoxy.

R¹⁹ is hydrogen, C₁-C₆alkyl, C₂-C₆alkenyl, C₂-C₆alkanoyl, —SO₂C₁-C₆alkyl, (mono- and di-C₁-C₆alkylamino)C₁-C₄alkyl, —C₀-C₄alkyl(C₃-C₇cycloalkyl), —C₀-C₄alkyl(C₃-C7heterocycloalkyl), —C₀-C₄alkyl(aryl), C₀-C₄alkyl(heteroaryl), and wherein R¹⁹ other than hydrogen is unsubstituted or substituted with one or more substituents independently chosen from halogen, hydroxyl, amino, —COOH, and —C(O)OC₁-C₄alkyl.

X¹¹ is N or CR¹¹.
X¹² is N or CR¹².
X¹³ is N or CR¹³.
X¹⁴ is N or CR¹⁴.
No more than 2 of X¹¹, X¹², X¹³, and X¹⁴ are N.

R¹¹, R¹⁴, and R¹⁵ are independently chosen at each occurrence from hydrogen, halogen, hydroxyl, nitro, cyano, —O(PO)(OR⁹)₂, —(PO)(OR⁹)₂, C₁-C₆alkyl, C₂-C₆alkenyl, C₂-C₆alkynyl, C₂-C₆alkenyl(aryl), C₂-C₆alkenyl(cycloalkyl), C₂-C₆alkenyl(heterocycle), C₂-C₆alkenyl(heteroaryl), C₂-C₆alkynyl, C₂-C₆alkynyl(aryl), C₂-C₆alkynyl (cycloalkyl), C₂-C₆alkynyl(heterocycle), C₂-C₆alkynyl (heteroaryl), C₂-C₆alkanoyl, C₁-C₆alkoxy, C₁-C₆thioalkyl, —C₀-C₄alkyl(mono- and di-C₁-C₆alkylamino), —C₀-C₄alkyl(C₃-C₇cycloalkyl), —C₀-C₄alkoxy(C₃-C7cycloalkyl), C₁-C₂haloalkyl, and C₁-C₂haloalkoxy.

In one embodiment, R⁵ and R⁶ are independently chosen from —CHO, —C(O)NH₂, —C(O)NH(CH₃), C₂-C₆alkanoyl, and hydrogen.

In one embodiment, each R⁵ and R⁶ other than hydrogen, hydroxyl, cyano, and —COOH is unsubstituted or substituted with one or more substituents independently chosen from halogen, hydroxyl, amino, imino, cyano, cyanoimino, C₁-C₂alkyl, C₁-C₄alkoxy, —C₀-C₂alkyl(mono- and di—C₁-C₄alkylamino), C₁-C₂haloalkyl, and C₁-C₂haloalkoxy.

In one embodiment, R⁸ and R⁸' are independently hydrogen or methyl.

In one embodiment, R⁸ and R⁸' are hydrogen.

In one embodiment, R⁷ is hydrogen or methyl.

In one embodiment, R⁷ is hydrogen.

Embodiments of Formulas IA, IB, IC, and ID

To further illustrate the invention, various embodiments of Formula IA, IB, IC and ID are provided. These are presented by way of example to show some of the variations among presented compounds within the invention and can be applied to any of the Formulas I-XXX.

In one aspect, this disclosure includes compounds and salts of Formula IA:

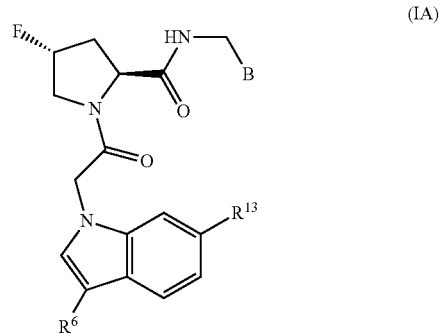

(IA)

where $R^6$, $R^{13}$, and B may carry any of the definitions set forth herein for this variable.

In another aspect, this disclosure includes compounds and salts of Formula IB, IC, and ID.

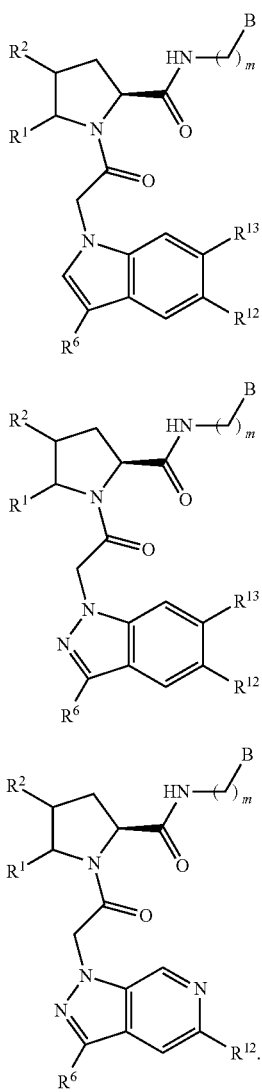

In Formulas IA, IB, IC, and ID, the variables may include any of the definitions set forth herein that results in a stable compound. In certain embodiments, the following conditions apply for Formula IB and IC.

In some embodiments, structures are provided including Formulas IB and IC, wherein m=0, $R^1$ is H, $R^2$ is F, $R^6$ is alkanoyl, $R^{12}$ is —OC(O)NR$^{24}$R$^{25}$, $R^{13}$ is H, and B is heteroaryl.

In some embodiments, structures are provided including Formulas IB and IC, wherein m=0, $R^1$ and $R^2$ are joined to form a 3 membered ring, $R^6$ is alkanoyl, $R^{12}$ is —OC(O)NR$^{24}$R$^{25}$, $R^{13}$ is H, and B is heteroaryl.

In some embodiments, structures are provided including Formulas IB and IC, wherein m=0, $R^1$ is H, $R^2$ is F, $R^6$ is amide, $R^{12}$ is —OC(O)NR$^{24}$R$^{25}$, $R^{13}$ is H, and B is heteroaryl.

In some embodiments, structures are provided including Formulas IB and IC, wherein m=0, $R^1$ and $R^2$ are joined to form a 3 membered ring, $R^6$ is amide, $R^{12}$ is —OC(O)NR$^{24}$R$^{25}$, $R^{13}$ is H, and B is heteroaryl.

In some embodiments, structures are provided including Formulas IB and IC, wherein m=0, $R^1$ is H, $R^2$ is F, $R^6$ is alkanoyl, $R^{12}$ is H, $R^{13}$ is —OC(O)NR$^{24}$R$^{25}$, and B is heteroaryl.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is —OC(O)NR$^{24}$R$^{25}$, and B is heteroaryl.

In some embodiments, structures are provided including Formulas IB and IC, wherein m=0, $R^1$ is H, $R^2$ is F, $R^6$ is amide, $R^{12}$ is H, $R^{13}$ is —OC(O)NR$^{24}$R$^{25}$, and B is heteroaryl.

In some embodiments, structures are provided including Formulas IB and IC, wherein m=0, $R^1$ and $R^2$ are joined to form a 3 membered ring, $R^6$ is amide, $R^{12}$ is H, $R^{13}$ is —OC(O)NR$^{24}$R$^{25}$, and B is heteroaryl.

In some embodiments, structures are provided including Formulas IB and IC, wherein m=0, $R^1$ is H, $R^2$ is F, $R^6$ is alkanoyl, $R^{12}$ is —OC(O)NR$^{24}$R$^{25}$, $R^{13}$ is H, and B is phenyl.

In some embodiments, structures are provided including Formulas IB and IC, wherein m=0, $R^1$ and $R^2$ are joined to form a 3 membered ring, $R^6$ is alkanoyl, $R^{12}$ is —OC(O)NR$^{24}$R$^{25}$, $R^{13}$ is H, and B is phenyl.

In some embodiments, structures are provided including Formulas IB and IC, wherein m=0, $R^1$ is H, $R^2$ is F, $R^6$ is amide, $R^{12}$ is —OC(O)NR$^{24}$R$^{25}$, $R^{13}$ is H, and B is phenyl.

In some embodiments, structures are provided including Formulas IB and IC, wherein m=0, $R^1$ and $R^2$ are joined to form a 3 membered ring, $R^6$ is amide, $R^{12}$ is —OC(O)NR$^{24}$R$^{25}$, $R^{13}$ is H, and B is phenyl.

In some embodiments, structures are provided including Formulas IB and IC, wherein m=0, $R^1$ is H, $R^2$ is F, $R^6$ is alkanoyl, $R^{12}$ is H, $R^{13}$ is —OC(O)NR$^{24}$R$^{25}$, and B is phenyl.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is —OC(O)NR$^{24}$R$^{25}$, and B is phenyl.

In some embodiments, structures are provided including Formulas IB and IC, wherein m=0, $R^1$ is H, $R^2$ is F, $R^6$ is amide, $R^{12}$ is H, $R^{13}$ is —OC(O)NR$^{24}$R$^{25}$, and B is phenyl.

In some embodiments, structures are provided including Formulas IB and IC, wherein m=0, $R^1$ and $R^2$ are joined to form a 3 membered ring, $R^6$ is amide, $R^{12}$ is H, $R^{13}$ is —OC(O)NR$^{24}$R$^{25}$, and B is phenyl.

In some embodiments, structures are provided including Formulas IB and IC, wherein m=1, $R^1$ is H, $R^2$ is F, $R^6$ is alkanoyl, $R^{12}$ is —OC(O)NR$^{24}$R$^{25}$, $R^{13}$ is H, and B is heteroaryl.

In some embodiments, structures are provided including Formulas IB and IC, wherein m=1, $R^1$ and $R^2$ are joined to form a 3 membered ring, $R^6$ is alkanoyl, $R^{12}$ is —OC(O)NR$^{24}$R$^{25}$, $R^{13}$ is H, and B is heteroaryl.

In some embodiments, structures are provided including Formulas IB and IC, wherein m=1, $R^1$ is H, $R^2$ is F, $R^6$ is amide, $R^{12}$ is —OC(O)NR$^{24}$R$^{25}$, $R^{13}$ is H, and B is heteroaryl.

In some embodiments, structures are provided including Formulas IB and IC, wherein m=1, $R^1$ and $R^2$ are joined to form a 3 membered ring, $R^6$ is amide, $R^{12}$ is —OC(O)NR$^{24}$R$^{25}$, $R^{13}$ is H, and B is heteroaryl.

In some embodiments, structures are provided including Formulas IB and IC, wherein m=1, $R^1$ is H, $R^2$ is F, $R^6$ is alkanoyl, $R^{12}$ is H, $R^{13}$ is —OC(O)NR$^{24}$R$^{25}$, and B is heteroaryl.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is —OC(O)NR$^{24}$R$^{25}$, and B is heteroaryl.

In some embodiments, structures are provided including Formulas IB and IC, wherein m=1, $R^1$ is H, $R^2$ is F, $R^6$ is amide, $R^{12}$ is H, $R^{13}$ is —OC(O)NR$^{24}$R$^{25}$, and B is heteroaryl.

In some embodiments, structures are provided including Formulas IB and IC, wherein m=1, $R^1$ and $R^2$ are joined to form a 3 membered ring, $R^6$ is amide, $R^{12}$ is H, $R^{13}$ is —OC(O)NR$^{24}$R$^{25}$, and B is heteroaryl.

In some embodiments, structures are provided including Formulas IB and IC, wherein m=1, $R^1$ is H, $R^2$ is F, $R^6$ is alkanoyl, $R^{12}$ is —OC(O)NR$^{24}$R$^{25}$, $R^{13}$ is H, and B is phenyl.

In some embodiments, structures are provided including Formulas IB and IC, wherein m=1, $R^1$ and $R^2$ are joined to form a 3 membered ring, $R^6$ is alkanoyl, $R^{12}$ is —OC(O)NR$^{24}$R$^{25}$, $R^{13}$ is H, and B is phenyl.

In some embodiments, structures are provided including Formulas IB and IC, wherein m=1, $R^1$ is H, $R^2$ is F, $R^6$ is amide, $R^{12}$ is —OC(O)NR$^{24}$R$^{25}$, $R^{13}$ is H, and B is phenyl.

In some embodiments, structures are provided including Formulas IB and IC, wherein m=1, $R^1$ and $R^2$ are joined to form a 3 membered ring, $R^6$ is amide, $R^{12}$ is —OC(O)NR$^{24}$R$^{25}$, $R^{13}$ is H, and B is phenyl.

In some embodiments, structures are provided including Formulas IB and IC, wherein m=1, $R^1$ is H, $R^2$ is F, $R^6$ is alkanoyl, $R^{12}$ is H, $R^{13}$ is —OC(O)NR$^{24}$R$^{25}$, and B is phenyl.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is —OC(O)NR$^{24}$R$^{25}$, and B is phenyl.

In some embodiments, structures are provided including Formulas IB and IC, wherein m=1, $R^1$ is H, $R^2$ is F, $R^6$ is amide, $R^{12}$ is H, $R^{13}$ is —OC(O)NR$^{24}$R$^{25}$, and B is phenyl.

In some embodiments, structures are provided including Formulas IB and IC, wherein m=1, $R^1$ and $R^2$ are joined to form a 3 membered ring, $R^6$ is amide, $R^{12}$ is H, $R^{13}$ is —OC(O)NR$^{24}$R$^{25}$, and B is phenyl.

In the above embodiments, structures are provided including Formulas IB and IC, wherein $R^{24}$ and $R^{25}$ are taken together with the nitrogen to which they are attached to form a 4- to 7-membered monocyclic heterocycloalkyl group, or a 6- to 10- membered bicyclic heterocyclic group having fused, spiro, or bridged rings, each of which is optionally substituted.

Embodiments of Formula VII

To further illustrate the invention, various embodiments of Formula VII. In one aspect, the disclosure includes compounds and salts of Formula VII:

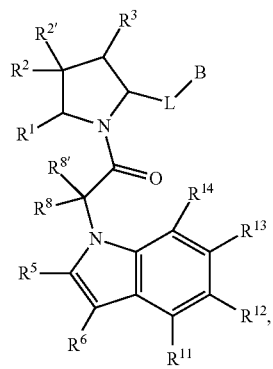

(VII)

wherein:

$R^1$, $R^2$, $R^{2'}$, and $R^3$ are independently chosen from hydrogen, halogen, $C_1$-$C_4$alkyl, $C_1$-$C_4$alkoxy, —$C_0$-$C_2$alkylNR$^9$R$^{10}$, —$C_0$-$C_4$alkyl($C_3$-$C_7$cycloalkyl), —O—$C_0$-$C_4$alkyl($C_3$-C7cycloalkyl), $C_1$-$C_2$haloalkyl, and $C_1$-$C_2$haloalkoxy;

$R^8$ and $R^{8'}$ are independently chosen from hydrogen, halogen, and methyl;

$R^5$ is hydrogen, hydroxyl, cyano, —COOH, $C_1$-$C_6$alkyl, $C_1$-$C_6$alkoxy, $C_2$-$C_6$alkanoyl —$C_0$-$C_4$alkyl($C_3$-$C_7$cycloalkyl), —C(O)$C_0$-$C_4$alkyl($C_3$-$C_7$cycloalkyl), $C_1$-$C_2$haloalkyl, or $C_1$-$C_2$haloalkoxy;

$R^6$ is —C(O)CH$_3$, —C(O)NH$_2$, —C(O)CF$_3$, —C(O)(cyclopropyl), or -ethyl(cyanoimino); and $R^{11}$ and $R^{14}$ are independently chosen from hydrogen, halogen, hydroxyl, amino, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —O$C_0$-$C_4$alkyl($C_3$-C7cycloalkyl), $C_1$-$C_2$haloalkyl, and $C_1$-$C_2$haloalkoxy.

Prodrugs of Formula I are also within the scope of the disclosure.

III. Pharmaceutical Preparations

Compounds disclosed herein can be administered as the neat chemical, but can also administered as a pharmaceutical composition, that includes an effective amount for a host in need of treatment of the selected compound of Formula I, as described herein. Accordingly, the disclosure provides pharmaceutical compositions comprising an effective amount of compound or pharmaceutically acceptable salt of Formula I, together with at least one pharmaceutically acceptable carrier. The pharmaceutical composition may contain a compound or salt of Formula I as the only active agent, or, in an alternative embodiment, Formula I and at least one additional active agent. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 25, 50, 100, 200, 250, 300, 400, 500, 600, 700, or 750 mg of active compound, or its salt. The pharmaceutical composition may also include a molar ratio of a compound of Formula I and an additional active agent. For example the pharmaceutical composition may contain a molar ratio of about 0.5:1, about 1:1, about 2:1, about 3:1 or from about 1.5:1 to about 4:1 of an another anti-inflammatory agent.

Compounds disclosed herein may be administered orally, topically, parenterally, by inhalation or spray, sublingually, via implant, including ocular implant, transdermally, via buccal administration, rectally, as an ophthalmic solution, injection, including ocular injection, intraveneous, intraaortal, intracranial, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound for Formula I that achieves the desired result, for example between 0.1 and 99 weight % (wt.%) of a compound of Formula I and usually at least about 5 wt. % of a compound of Formula I. Some embodiments contain from about 25 wt. % to about 50 wt. % or from about 5 wt. % to about 75 wt. % of the compound of Formula I.

The complement factor D inhibitors of the present invention can be administered, for example, either systemically or locally. Systemic administration includes, for example, oral, transdermal, subdermal, intraperitioneal, subcutaneous, transnasal, sublingual, or rectal. Local administration for ocular administration includes: topical, intravitreal, periocular, transscleral, retrobulbar, juxtascleral, sub-tenon, or via an intraocular device. The inhibitors may be delivered via a sustained delivery device implanted intravitreally or transsclerally, or by other known means of local ocular delivery.

IV. Methods of Treatment

The compounds and pharmaceutical compositions disclosed herein are useful for treating or preventing a disorder that is mediated by the complement pathway, and in particular, a pathway that is modulated by complement factor D. In certain embodiments, the disorder is an inflammatory disorder, an immune disorder, an autoimmune disorder, or complement factor D related disorders in a host. In one embodiment, the disorder is an ocular disorder. Complement mediated disorders that may be treated or prevented by the compounds and compositions of this disclosure include, but are not limited to, inflammatory effects of sepsis, systemic inflammatory response syndrome (SIRS), ischemia/reperfusion injury (I/R injury), psoriasis, myasthenia gravis, system lupus erythematosus (SLE), paroxysmal nocturnal hemoglobinuria (PNH), hereditary angioedema, multiple sclerosis, trauma, burn injury, capillary leak syndrome, obesity, diabetes, Alzheimer's dementia, stroke, schizophrenia, epilepsy, age-related macular degeneration, glaucoma, diabetic retinopathy, asthma, allergy, acute respiratory distress syndrome (ARDS), atypical hemolytic uremic syndrome (aHUS), hemolytic uremic syndrome (HUS), cystic fibrosis, myocardial infarction, lupus nephritides, Crohn's disease, rheumatoid arthritis, atherosclerosis, transplant rejection, prevention of fetal loss, biomaterial reactions (e.g. in hemodialysis, inplants), C3 glomerulonephritis, abdominal aortic aneurysm, neuromyelitis optica (NMO), vasculitis, neurological disorders, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during I L-2 therapy, inflammatory disorders, inflammation of autoimmune diseases, adult respiratory distress syndrome, thermal injury including burns or frostbite, myocarditis, post-ischemic reperfusion conditions, balloon angioplasty, post-pump syndrome in cardiopulmonary bypass or renal bypass, hemodialysis, renal ischemia, mesenteric artery reperfusion after aortic reconstruction, immune complex disorders and autoimmune diseases, SLE nephritis, proliferative nephritis, liver fibrosis, hemolytic anemia, tissue regeneration and neural regeneration. In addition, other known complement related disease are lung disease and disorders such as dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome, arthritis, autoimmune heart disease, inflammatory bowel disease, ischemia-reperfusion injuries, Barraquer—Simons Syndrome, hemodialysis, systemic lupus, lupus erythematosus, transplantation, diseases of the central nervous system and other neurodegenerative conditions, glomerulonephritis (including membrane proliferative glomerulonephritis), blistering cutaneous diseases (including bullous pemphigoid, pemphigus, and epidermolysis bullosa), ocular cicatrical pemphigoid, MPGN II, uveitis, adult macular degeneration, diabetic retinopathy, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion.

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

In one embodiment, a method for the treatment of paroxysmal nocturnal hemoglobinuria (PNH) is provided that includes the administration of an effective amount of a compound of Formula I, or a pharmaceutically acceptable salt thereof, optionally in a pharmaceutically acceptable carrier. In another embodiment, a method for the treatment of age-related macular degeneration (AMD) is provided that includes the administration of an effective amount of a compound of Formula I, or a pharmaceutically acceptable salt thereof, optionally in a pharmaceutically acceptable carrier. In another embodiment, a method for the treatment of rheumatoid arthritis is provided that includes the administration of an effective amount of a compound of Formula I, or a pharmaceutically acceptable salt thereof, optionally in a pharmaceutically acceptable carrier. In another embodiment, a method for the treatment of multiple sclerosis is provided that includes the administration of an effective amount of a compound of Formula I, or a pharmaceutically acceptable salt thereof, optionally in a pharmaceutically acceptable carrier. In another embodiment, a method for the treatment of myasthenia gravis is provided that includes the administration of an effective amount of a compound of Formula I, or a pharmaceutically acceptable salt thereof, optionally in a pharmaceutically acceptable carrier. In another embodiment, a method for the treatment of atypical hemolytic uremic syndrome (aHUS) is provided that includes the administration of an effective amount of a compound of Formula I, or a pharmaceutically acceptable salt thereof, optionally in a pharmaceutically acceptable carrier. In another embodiment, a method for the treatment of C3 glomerulonephritis is provided that includes the administration of an effective amount of a compound of Formula I, or a pharmaceutically acceptable salt thereof, optionally in a pharmaceutically acceptable carrier. In another embodiment, a method for the treatment of abdominal aortic aneurysm is provided that includes the administration of an effective amount of a compound of Formula I, or a pharmaceutically acceptable salt thereof, optionally in a pharmaceutically acceptable carrier. In another embodiment, a method for the treatment of neuromyelitis optica (NMO) is provided that includes the administration of an effective amount of a compound of Formula I, or a pharmaceutically acceptable salt thereof, optionally in a pharmaceutically acceptable carrier.

In some embodiments, the present invention provides methods of treating or preventing an inflammatory disorder or a complement related disease, by administering to a host in need thereof an effective amount of a compound of Formula I of the invention. In some embodiments, the present invention provides methods of treating or preventing an inflammatory disorder more generally, an immune disorder, autoimmune disorder, or complement factor D related disease, by providing an effective amount of a compound or pharmaceutically acceptable salt of Formula I to patient with a factor D mediated inflammatory disorder. A compound or salt of Formula I may be provided as the only active agent or may be provided together with one or more additional active agents.

In one embodiment, a method for the treatment of a disorder associated with a dysfunction in the complement cascade is provided that includes the administration of an effective amount of a compound of Formula I, or a pharmaceutically acceptable salt thereof, optionally in a pharmaceutically acceptable carrier. In one embodiment, a method of inhibiting activation of the alternative complement pathway in a subject is provided that includes the administration of an effective amount of a compound of Formula I, or a pharmaceutically acceptable salt thereof, optionally in a pharmaceutically acceptable carrier. In one embodiment, a method of modulating factor D activity in a subject is provided that includes the administration of an effective amount of a compound of Formula I, or a pharmaceutically acceptable salt thereof, optionally in a pharmaceutically acceptable carrier.

"Prevention" as used in this disclosure means decreasing the likelihood of the appearance of symptoms in a patient administered the compound prophylactically as compared to the likelihood of the appearance of symptoms in patients not administered the compound or decreasing the severity of symptoms in a patient administered the compound prophylactically as compared to the severity of symptoms experienced by patients with the disorder or condition who were not administered the compound. In an alternative embodiment, an effective amount of a compound of Formula I is used to prevent or prophylaxis of a complement factor D related disorder.

An effective amount of a pharmaceutical composition/combination of the invention may be an amount sufficient to (a) inhibit the progression of a disorder mediated by the complement pathway, including an inflammatory, immune, including an autoimmune, disorder or complement factor D related disease; (b) cause a regression of an inflammatory, immune, including an autoimmune, disorder or complement factor D related disease; or (c) cause a cure of an inflammatory, immune, including an autoimmune, disorder or complement factor D related disease.

An effective amount of a compound or pharmaceutical composition described herein will also provide a sufficient amount of the active agent when administered to a patient to provide a clinical benefit. Such an amount may be ascertained experimentally, for example by assaying blood concentration of the agent, or theoretically, by calculating bioavailability.

V. Combination Therapy

In one embodiment, a compound or salt of Formula I may be provided in combination or alternation with at least one additional inhibitor of the complement system or a second active compound with a different biological mechanism of action. In one embodiment, a compound or salt of Formula I may be provided in combination with a complement C5 inhibitor or C5 convertase inhibitor. In another embodiment, a compound or salt of Formula I may be provided in combination with eculizumab. In one embodiment, a compound or salt of Formula I may be provided in combination with additional inhibitors of factor D.

In one embodiment, a compound or salt of Formula I may be provided together with a compound that inhibits an enzyme that metabolizes protease inhibitors. In one embodiment, a compound or salt of Formula I may be provided together with ritonavir.

In nonlimiting embodiments, a compound or salt of Formula I may be provided together with a protease inhibitor, a soluble complement regulator, a therapeutic antibody (monoclonal or polyclonal), complement component inhibitors, receptor agonists, or siRNAs.

Nonlimiting examples of active agents in these categories are:

Protease inhibitors: plasma-derived C1-INH concentrates, for example Cetor® (Sanquin), Berinert—P® (CSL Beh-ring, Lev Pharma), and Cinryze®; and recombinant human C1-inhibitors, for example Rhucin®;

Soluble complement regulators: Soluble complement receptor 1 (TP10) (Avant Immunotherapeutics); sCR1-sLe$^x$/TP-20 (Avant Immunotherapeutics); MLN-2222/CAB-2 (Millenium Pharmaceuticals); Mirococept (Inflazyme Pharmaceuticals);

Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix);

Receptor agonists: PMX-53 (Peptech Ltd.); JPE-137 (Jerini); JSM-7717 (Jerini);

Others: Recombinant human MBL (rhMBL; Enzon Pharmaceuticals).

In an embodiment, the present invention provides a method of treating or preventing age-related macular degeneration (AMD) by administering to a subject in need thereof an effective amount of a composition comprising a compound of the current invention. In one embodiment, the compositions of the present invention are administered in combination with an anti-VEGF agent. Nonlimiting examples of anti-VEGF agents include, but are not limited to, aflibercept (Eylea®; Regeneron Pharmaceuticals); ranibizumab (Lucentis®: Genentech and Novartis); and pegaptanib (Macugen®; OSI Pharmaceuticals and Pfizer); Bevacizumab (Avastin; Genentech/Roche); anecortane acetate, squalamine lactate, and corticosteroids, including, but not limited to, triamcinolone acetonide.

In another embodiment, a compound of Formula I can be combined with a second agent in order to treat a disorder of the eye.

Examples of types of therapeutic agents that can be used in combination for ocular applications include anti-inflammatory drugs, antimicrobial agents, anti-angiogenesis agents, immunosuppressants, antibodies, steroids, ocular antihypertensive drugs and combinations thereof. Examples of therapeutic agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluorometholone, rimexolone, anecortave, cyclosporine, methotrexate, tacrolimus and combinations thereof. Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens—Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

A compound of Formula I, or a combination of Formula I and another active agent, can be administered into an eye compartment of via injection into the vitreous chamber, subretinal space, subchoroidal space, the episclera, the conjunctiva, the sclera, the anterior chamber, and the cornea and compartments therein (e.g., subepithelial, intrastromal, endothelial).

In an alternative embodiment, a compound of Formula I, or a combination of Formula I and another active agent, can be administered into an eye compartment via binding to a mucosal penetrating particle to treat a condition located in the vitreous chamber, subretinal space, subchoroidal space, the episclera, the conjunctiva, the sclera or the anterior chamber, and the cornea and compartments therein (e.g., subepithelial, intrastromal, endothelial). Mucosal penetrating particles are known in the art, and are described in, for example, PCT published application WO 2013166436 to Kala Pharmaceuticals, incorporated in its entirety herein.

In other embodiments, a composition comprising compound of Formula I suitable for topical administration to an eye is provided. The pharmaceutical composition comprises a plurality of coated particles, comprising a core particle comprising a compound of Formula I, wherein Formula I constitutes at least about 80 wt % of the core particle, and a coating comprising one or more surface-altering agents, wherein the one or more surface-altering agents comprise at least one of a poloxamer, a poly(vinyl alcohol), or a polysorbate. The one or more surface-altering agents is present on the outer surface of the core particle at a density of at least 0.01 molecules/nm. The one or more surface-altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

It will be appreciated by one of ordinary skill in the art that particles suitable for use with the presently disclosed methods can exist in a variety of shapes, including, but not limited to, spheroids, rods, disks, pyramids, cubes, cylinders, nanohelixes, nanosprings, nanorings, rod-shaped particles, arrow-shaped particles, teardrop-shaped particles, tetrapod-shaped particles, prism-shaped particles, and a plurality of other geometric and non-geometric shapes. In some embodiments, the presently disclosed particles have a spherical shape.

In one embodiment, the present invention provides a method of treating or preventing paroxysmal nocturnal hemoglobinuria (PNH) by administering to a subject in need thereof an effective amount of a composition comprising a compound of the current invention. In one embodiment, the present invention provides a method of treating or preventing paroxysmal nocturnal hemoglobinuria (PNH) by administering to a subject in need thereof an effective amount of a composition comprising a compound of the current invention in combination or alternation with additional inhibitors of the complement system or another active compound with a different biological mechanism of action. In another embodiment, the present invention provides a method of treating or preventing paroxysmal nocturnal hemoglobinuria (PNH) by administering to a subject in need thereof an effective amount of a composition comprising a compound of the current invention in combination or alternation with eculizumab.

In one embodiment, the present invention provides a method of treating or preventing rheumatoid arthritis by administering to a subject in need thereof an effective amount of a composition comprising a compound of the current invention. In one embodiment, the present invention provides a method of treating or preventing rheumatoid arthritis by administering to a subject in need thereof an effective amount of a composition comprising a compound of the current invention in combination or alternation with an additional inhibitor of the complement system. In another embodiment, the present invention provides a method of treating or preventing rheumatoid arthritis by administering to a subject in need thereof an effective amount of a composition comprising a compound of the current invention in combination or alternation with methotrexate.

In certain embodiments, a compound of Formula I is administered in combination or alternation with at least one anti-rhuematoid arthritis drug selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a subject in need thereof an effective amount of a composition comprising a compound of the current invention. In one embodiment, the present invention provides a method of treating or preventing multiple sclerosis by administering to a subject in need thereof an effective amount of a composition comprising a compound of the current invention in combination or alternation with additional inhibitors of the complement system. In another embodiment, the present invention provides a method of treating or preventing multiple sclerosis by administering to a subject in need thereof an effective amount of a composition comprising a compound of the current invention in combination or alternation with a corticosteroid. Examples of corticosteroids include, but are not limited to, prednisone, dexamethasone, solumedrol, and methylprednisolone.

In one embodiment, a compound of Formula I is combined with at least one anti-multiple sclerosis drug selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), Solu-Medrol (methylprednisolone), High-dose oral Deltasone (prednisone), H.P. Acthar Gel (ACTH), and combinations thereof.

In one aspect, a compound or salt of Formula I may be provided in combination or alternation with an immunosuppressive agent or an anti-inflammatory agent.

In one embodiment of the present invention, a compound described herein can be administered in combination or alternation with at least one immunosuppressive agent. The immunosuppressive agent as nonlimiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g.ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

Examples of anti-inflammatory agents include methotrexate, dexamethasone, dexamethasone alcohol, dexamethasone sodium phosphate, fluromethalone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, a compound of Formula I is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

VI. Process of Preparation of Compounds of Formula I

Abbreviations (Boc)$_2$O di-tert-butyl dicarbonate
AcCl acetyl chloride
ACN Acetonitrile
AcOEt, EtOAc ethyl acetate
Aq aqueous
CH$_3$OH, MeOH Methanol
CsF Cesium fluoride
CuI Cuprous iodide
dba dibenzylideneacetone
DCM, CH$_2$Cl$_2$ Dichloromethane
DIEA, DIPEA N,N-diisopropylethylamine
DMA N,N-dimethylacetamide
DMF N,N-dimethylformamide
DMSO Dimethylsulfoxide
DPPA Diphenyl phosphoryl azide
dppf 1,1'-bis(diphenylphosphino)ferrocene
Et3N, TEA Triethylamine
EtOAc Ethylacetate
EtOH Ethanol
FA formic acid
HATU 1-[Bis(dimethylamino)methylene]-1H-1,2,3-triazolo[4,5-b]pyridinium 3-oxide hexafluorophosphate
HCl Hydrochloric acid
IPA isopropyl alcohol
$^i$Pr2NE$_t$ N,N-diisopropylethylamine
K$_2$CO$_3$ Potassium carbonate
LiOH Lithium hydroxide
MTBE Methyl $^t$butylether
Na$_2$SO$_4$ Sodium sulfate
NaCl Sodium chloride
NaH Sodium hydride
NaHCO$_3$ Sodium bicarbonate
NEt$_3$ triethylamine
Pd (OAc)$_2$ Palladium acetate
Pd(dppf)Cl$_2$ [1,1'-Bis(diphenylphosphino) ferrocene]dichloropalladium(II)
Pd(PPh$_3$)$_2$Cl$_2$ Bis(triphenylphosphine)palladium(II) dichloride
Pd(PPh$_3$)$_4$ Tetrakis(triphenylphosphine)palladium(0)
Pd$_2$(dba)$_3$ Tris(dibenzylideneacetone)dipalladium(0)
POCl$_3$ phosphoryl chloride
PPh$_3$ Triphenylphosphine
RT Room temperature
RT room temperature
TBAF tetra-n-butylammonium fluoride
TBDMS tert-butyldimethylsilyl
TBDMSCl tert-butyldimethylsilyl chloride
tBuOK potassium tert-butoxide
TEA triethylamine
Tf$_2$O trifluoromethanesulfonic anhydride
TFA trifluoroacetic acid
TFA Trifluoroacetic acid
THF Tetrahydrofuran
TMS tetramethylsilyl
TMSBr bromotrimethylsilane
t$_R$ Retention time
Xantphos 4,5-bis(diphenylphosphino)-9,9-dimethylxanthene
Zn (CN)$_2$ Zinc cyanide General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

LC Method A
Instrument: Waters Acquity Ultra Performance LC
Column: ACQUITY UPLC BEH C18 2.1×50 mm, 1.7 μm
Column Temperature: 40° C.
Mobile Phase: Solvent A: H$_2$O+0.05% FA; Solvent B: CH$_3$CN+0.05% FA
Flow Rate: 0.8 mL/min
Gradient: 0.24 min @ 15% B, 3.26 min gradient (15-85% B), then 0.5 min @ 85% B.
Detection: UV (PDA), ELS, and MS (SQ in EI mode)

LC Method B
Instrument: Shimadzu LC-2010A HT
Column: Athena, C18-WP, 50×4.6 mm, 5 μm
Column Temperature: 40° C.
Mobile Phase: Solvent A: H$_2$O/CH$_3$OH/FA=90/10/0.1; Solvent B: H$_2$O/CH$_3$OH/FA=10/90/0.1
Flow Rate: 3 mL/min
Gradient: 0.4 min @ 30% B, 3.4 min gradient (30-100% B), then 0.8 min @ 100% B
Detection: UV (220/254 nm)

EXAMPLE 1

General Route of Synthesis

A compound of the present invention can be prepared, for example, from a central core. In one embodiment, for example, the central core Structure 1 is an N-protected aminoacid where $X^1$ is nitrogen and PG =protecting group. In one embodiment, the central core is coupled to an amine to generate an amide of Structure 2 (wherein L-B includes a C(O)N moiety). Structure 2 can then be deprotected to generate Structure 3. Structure 3 is coupled to Structure 4 (A—COOH) to generate a second amide bond, forming a compound within Formula I. The chemistry is illustrated in Route 1.

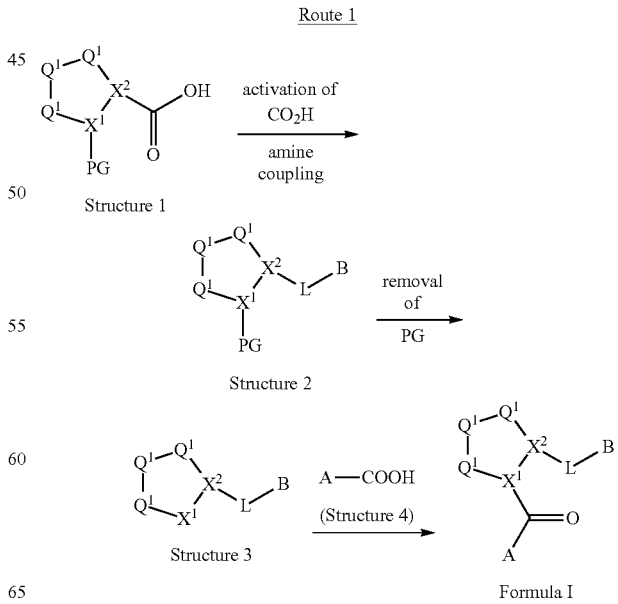

In an alternative embodiment, central core Structure 5 is reacted with a heterocyclic or heteroaryl compound to generate a compound of Structure 6. In one embodiment, Structure 6 is deprotected to generate a carboxylic acid, Structure 7. In one embodiment, Structure 7 is coupled to an amine to generate a compound of Formula I. This chemistry is illustrated in Route 2.

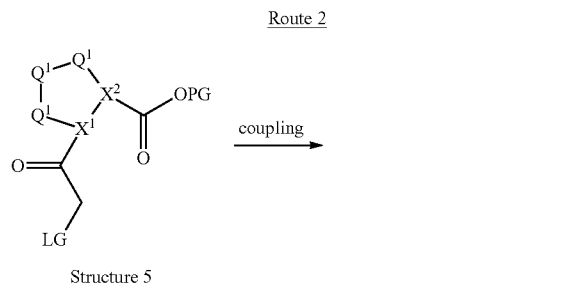

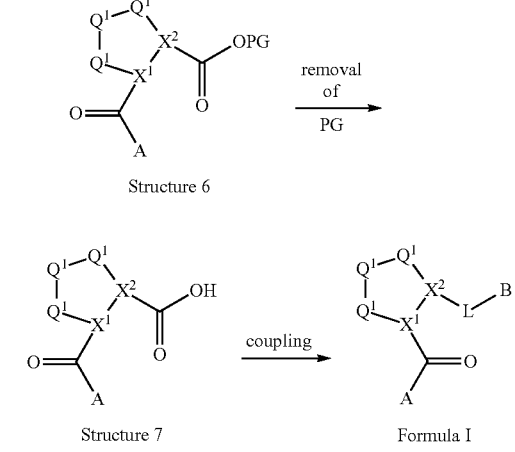

In an alternative embodiment, Structure 8 is deprotected to generate an amine which is Structure 9. Structure 9 is then coupled to generate an amide which is Structure 6. Structure 6 is then deprotected to generate a carboxylic acid which is Structure 7. Structure 7 is then coupled to form the amide which falls within Formula I. The chemistry is illustrated in Route 3.

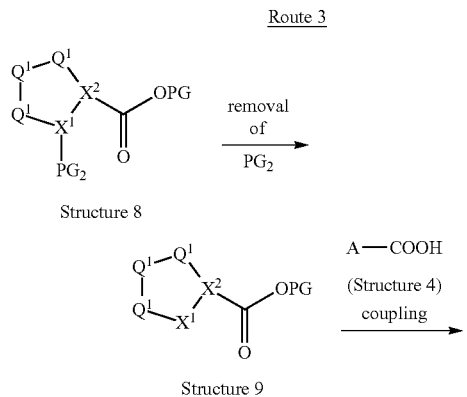

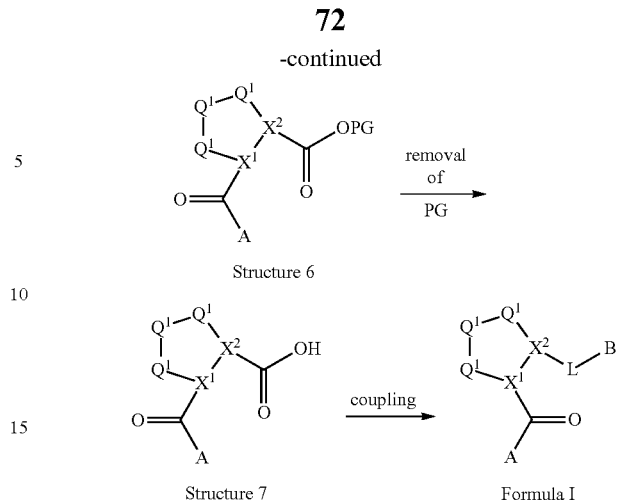

In an alternate embodiment, a heteroaryl compound of Structure 10 is acylated to generate Structure 11. In an alternate embodiment, Structure 10 is treated with for example, an inorganic cyanide and organometallic catalysts to generate $R^6$=cyano. The cyano group can be reacted with an oxime to generate an amide at the $R^6$ position; —C(O)NH$_2$. The PG is a protecting group, for example, benzyl. Structure 11 is next coupled to an activated ester, Structure 12, to generate Structure 13. In one embodiment, the LG (leaving group) is a halide. The protecting group on Structure 13 is removed to generate Structure 14. The ester, Structure 14, is hydrolyzed to form the acid; Structure 15. Structure 15 is coupled to Structure 3 from Route 1 to generate Structure 16. This chemistry is illustrated in Route 4.

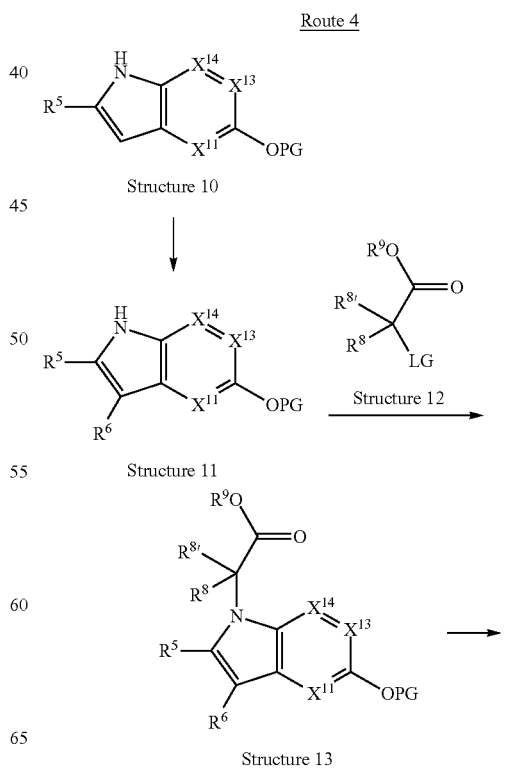

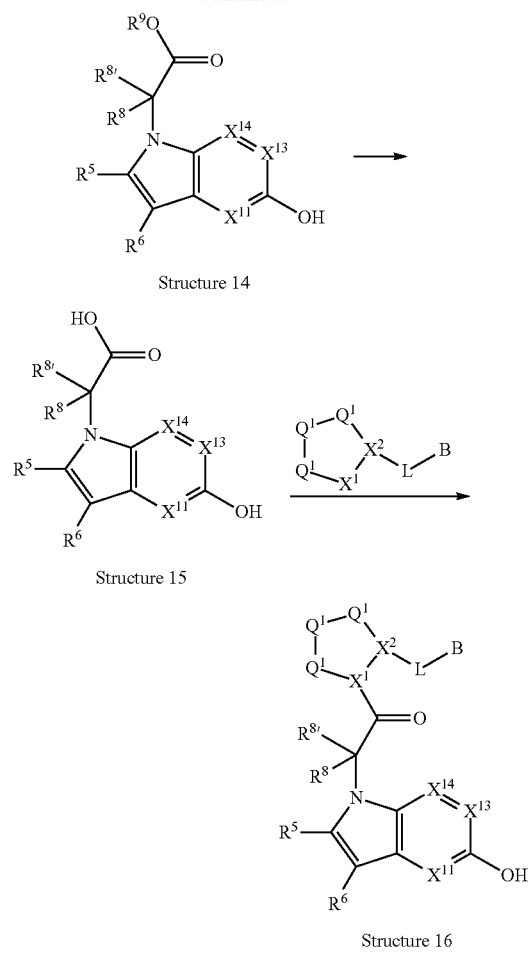

Structure 14

Structure 15

Structure 16

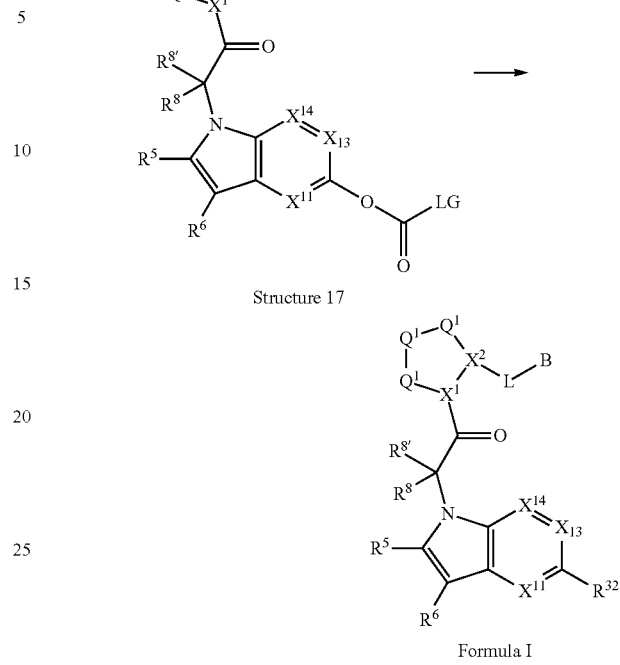

Structure 17

Formula I

Structure 16, from Route 4, is treated with a chloroformate to generate a carbonate, Structure 17, wherein LG is a leaving group. In one embodiment, the leaving group is p-nitrophenol. Structure 17 is treated with an amine to generate compounds within Formula I wherein $R^{32}$ is —OC(O)$NR^{21}R^{22}$, —OC(O)$NR^{24}R^{25}$, or —OC(O)$NR^9(CH_2)_{1-4}P(O)(OR^{21})(OR^{22})$. In some embodiments, Structure 16 is treated with an acid chloride or anhydride to generate compounds of Formula I wherein $R^{32}$ is —OC(O)$(CH_2)_{1-4}R^{21}$. This chemistry is illustrated in Route 5.

In an alternate embodiment, a heteroaryl compound of Structure 18 is acylated to generate Structure 19. In an alternate embodiment, Structure 18 can be treated with for example, an inorganic cyanide and organometallic catalysts to generate $R^6$=cyano. The cyano group can be treated with for example, an oxime to generate an amide, $R^6$ =—C(O)$NH_2$. The PG is a protecting group, for example benzyl. Structure 19 is next coupled to an activated ester, Structure 12, from Route 4, to generate Structure 20. In one embodiment, the LG (leaving group) is a halogen. The protecting group is removed to generate Structure 21. The ester in Structure 21 is hydrolyzed to form the acid; Structure 22. Structure 22 is coupled to Structure 3 from Route 1 to generate Structure 23. This chemistry is illustrated in Route 6.

Route 5

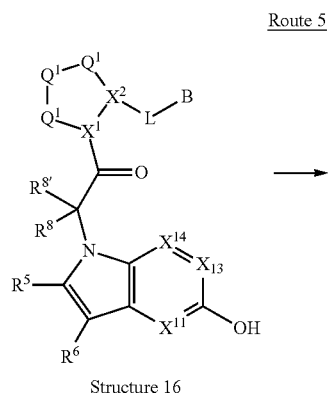

Structure 16

Route 6

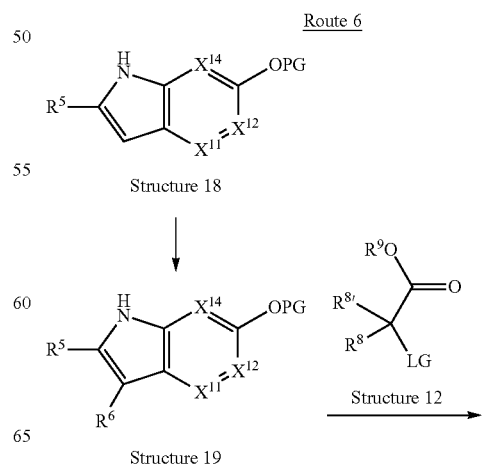

Structure 18

Structure 19    Structure 12

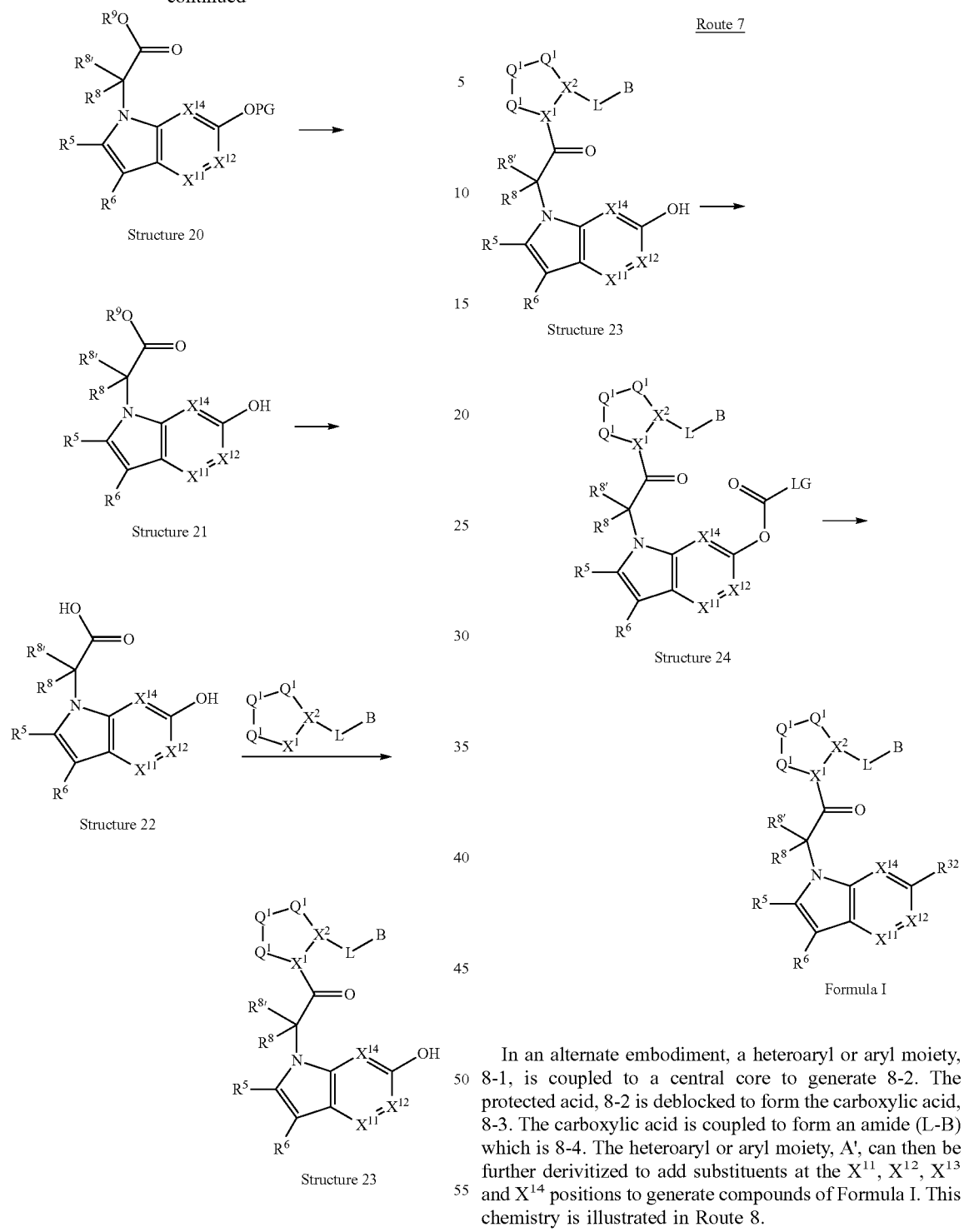

Structure 23, from Route 6, is activated with a carbonate group to generate Structure 24. In one embodiment, the leaving group is p-nitrophenol. The carbonate, Structure 24, is treated with an amine to generate compounds of Formula I wherein $R^{32}$ is —OC(O)$NR^{21}R^{22}$, —OC(O)$NR^{24}R^{25}$, or —OC(O)$NR^9(CH_2)_{1-4}P(O)(OR^{21})(OR^{22})$. The chemistry is illustrated in Route 7. In some embodiments, Structure 23 is treated with an acid chloride or anhydride to generate compounds of Formula I wherein $R^{32}$ is —OC(O)$(CH_2)_{1-4}R^{21}$.

In an alternate embodiment, a heteroaryl or aryl moiety, 8-1, is coupled to a central core to generate 8-2. The protected acid, 8-2 is deblocked to form the carboxylic acid, 8-3. The carboxylic acid is coupled to form an amide (L-B) which is 8-4. The heteroaryl or aryl moiety, A', can then be further derivitized to add substituents at the $X^{11}$, $X^{12}$, $X^{13}$ and $X^{14}$ positions to generate compounds of Formula I. This chemistry is illustrated in Route 8.

Route 8

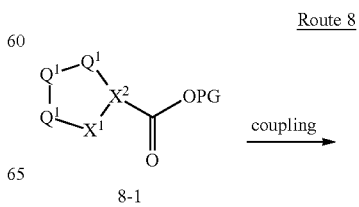

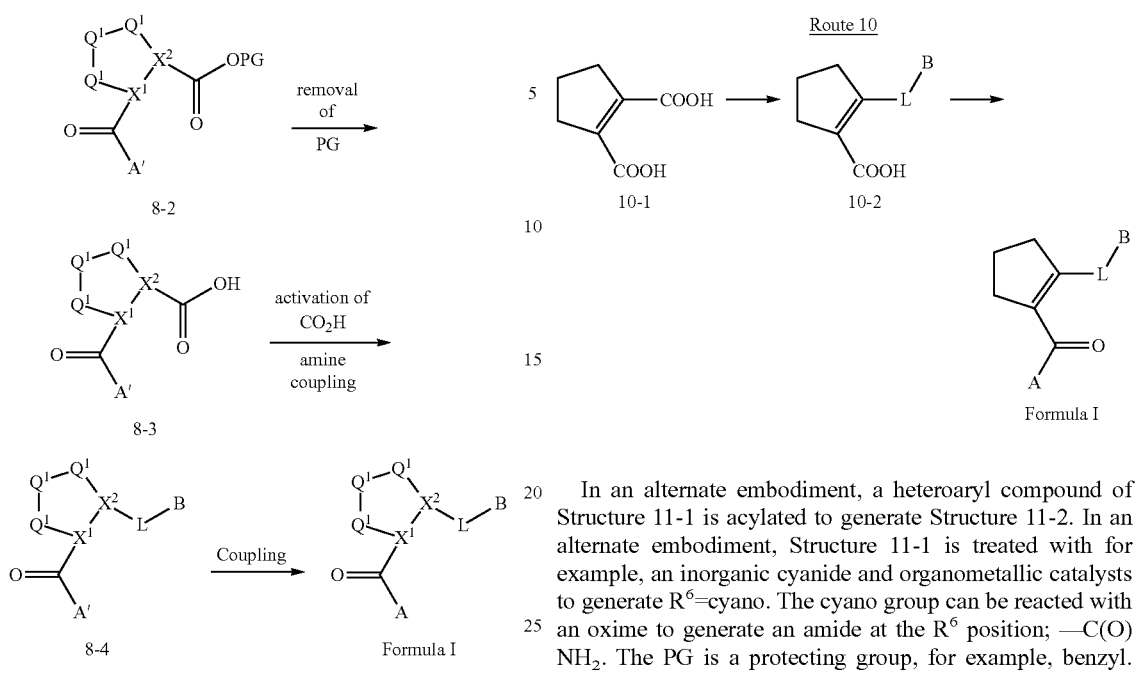

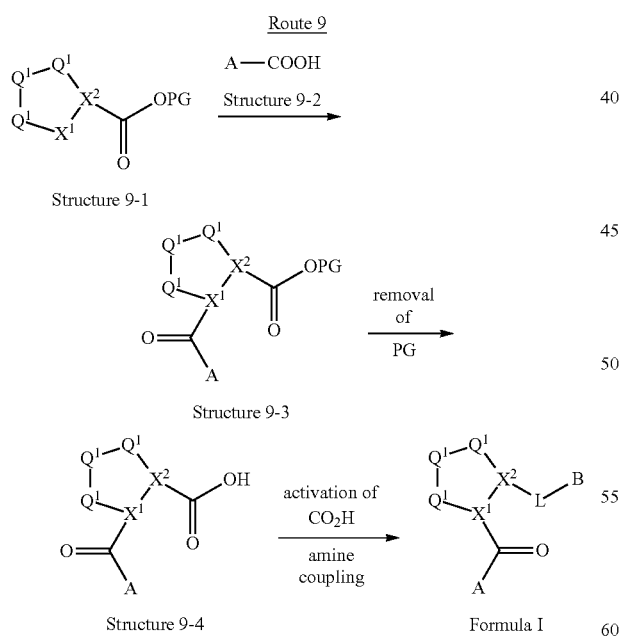

In an alternate embodiment, Structure 9-1 is coupled to an acid, Structure 9-2, to generate Structure 9-3. The carboxylic acid, Structure 9-3, is deblocked to generate a carboxylic acid which is Structure 9-4. Carboxylic acid Structure 9-4 is coupled to an amine to form an amide (L-B) and compounds within Formula I. This chemistry is illustrated in Route 9.

In an alternate embodiment, Structure 10-1 is coupled to an amine to generate an amide (L-B), which is Structure 10-2. Structure 10-2, is coupled to an amine to generate compounds within Formula I. This chemistry is illustrated in Route 10.

In an alternate embodiment, a heteroaryl compound of Structure 11-1 is acylated to generate Structure 11-2. In an alternate embodiment, Structure 11-1 is treated with for example, an inorganic cyanide and organometallic catalysts to generate $R^6$=cyano. The cyano group can be reacted with an oxime to generate an amide at the $R^6$ position; —C(O)NH$_2$. The PG is a protecting group, for example, benzyl. Structure 11-2 is next coupled to an activated ester, Structure 11-3, to generate Structure 11-4. In one embodiment, the LG (leaving group) is a halide. The protecting group on Structure 11-4 is removed to generate Structure 11-5. The ester, Structure 11-5, is hydrolyzed to form the acid which is Structure 11-6. Structure 11-6 is coupled to Structure 3 from Route 1 to generate Structure 11-7. This chemistry is illustrated in Route 11.

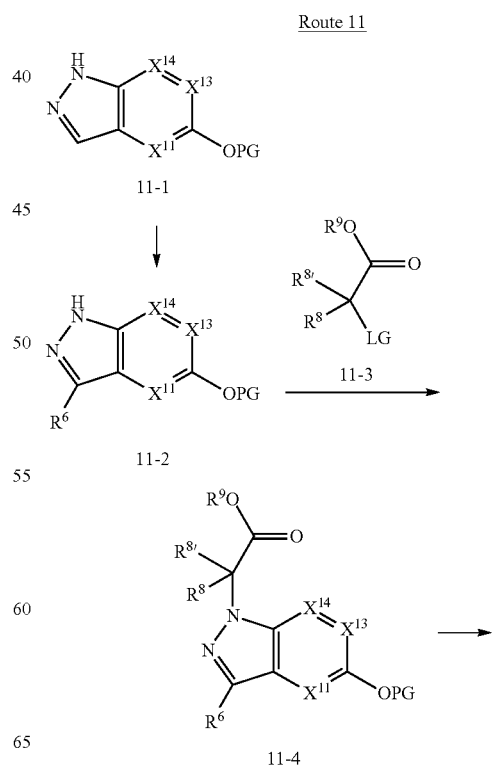

-continued

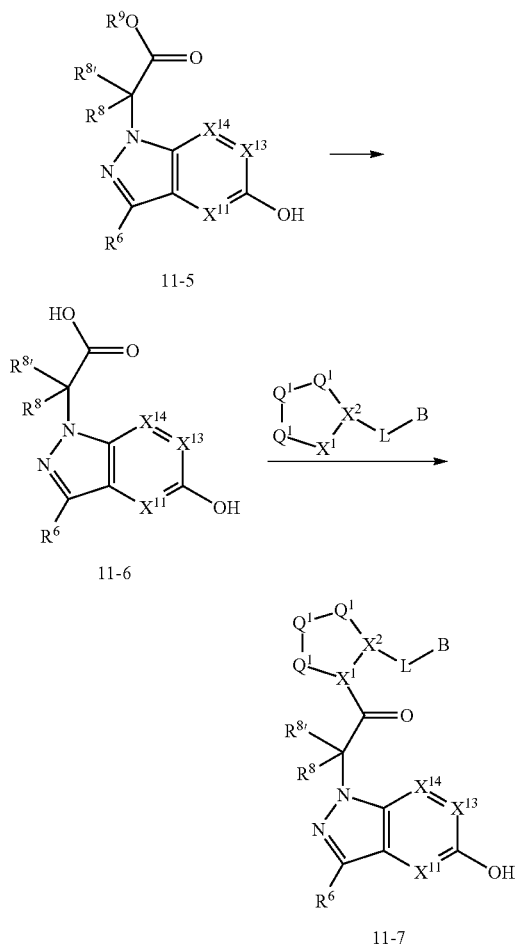

11-5

11-6

11-7

Structure 11-7, from Route 11, is treated with a chloroformate to generate a carbonate, Structure 12-1, wherein LG is a leaving group. In one embodiment, the leaving group is p-nitrophenol. Structure 12-1 is treated with an amine to generate compounds within Formula I wherein $R^{32}$ is —OC(O)$NR^{21}R^{22}$, —OC(O)$NR^{24}R^{25}$, or —OC(O)$NR^{9}(CH_2)_{1-4}$P(O)(O$R^{21}$)(O$R^{22}$). The chemistry is illustrated in Route 12. In some embodiments, Structure 11-7 is treated with an acid chloride or anhydride to generate compounds of Formula I wherein $R^{32}$ is —OC(O)$(CH_2)_{1-4}R^{21}$.

Route 12

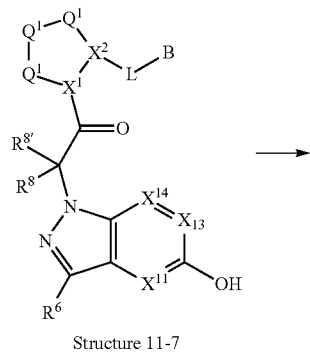

Structure 11-7

-continued

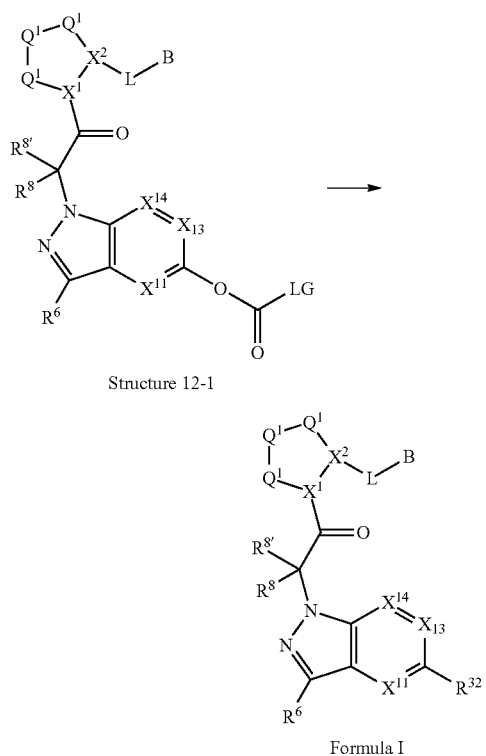

Structure 12-1

Formula I

In an alternate embodiment, a heteroaryl compound of Structure 13-1 is acylated to generate Structure 13-2. In an alternate embodiment, Structure 13-1 can be treated with for example, an inorganic cyanide and organometallic catalysts to generate $R^6$=cyano. The cyano group can be treated with for example, an oxime to generate an amide, $R^6$ =—C(O)$NH_2$. The PG is a protecting group, for example benzyl. Structure 13-2 is next coupled to an activated ester, Structure 13-3, to generate Structure 13-4. In one embodiment, the LG (leaving group) is a halide. The protecting group is removed to generate Structure 13-5. The ester in Structure 13-5 is hydrolyzed to form the acid which is Structure 13-6. Structure 13-6 is coupled to Structure 3 from Route 1 to generate Structure 13-7. This chemistry is illustrated in Route 13.

Route 13

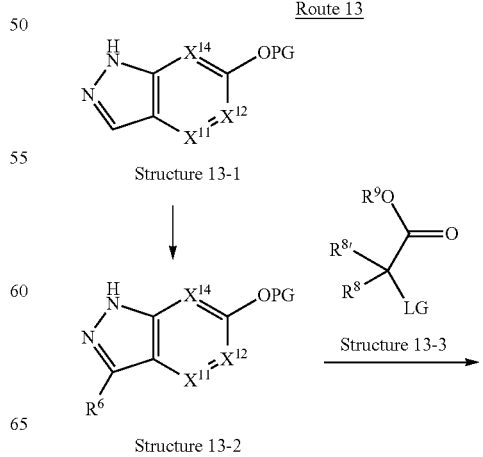

Structure 13-1

Structure 13-2

Structure 13-3

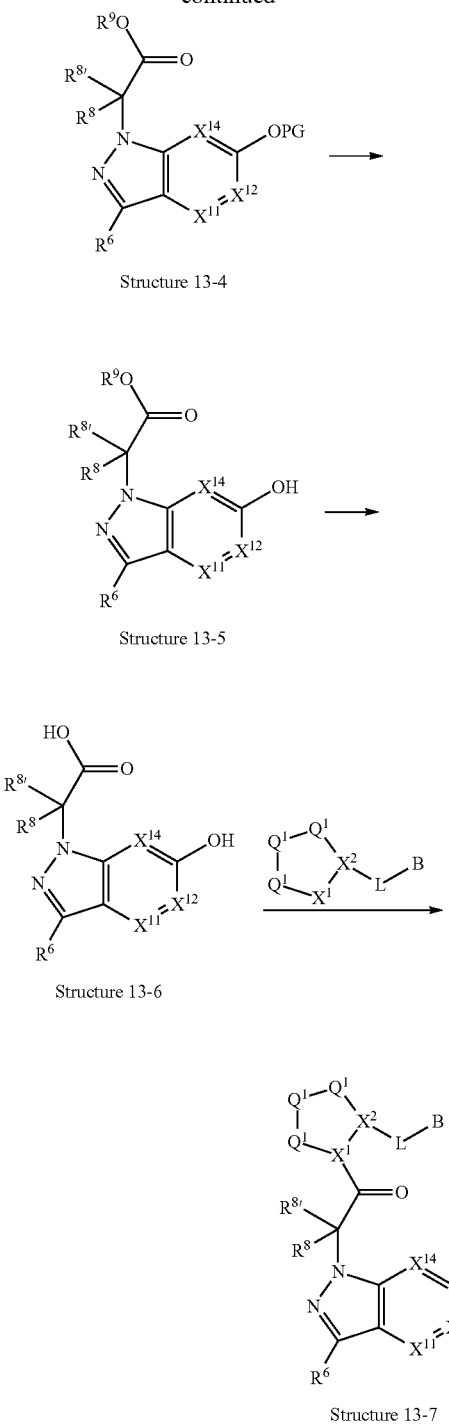

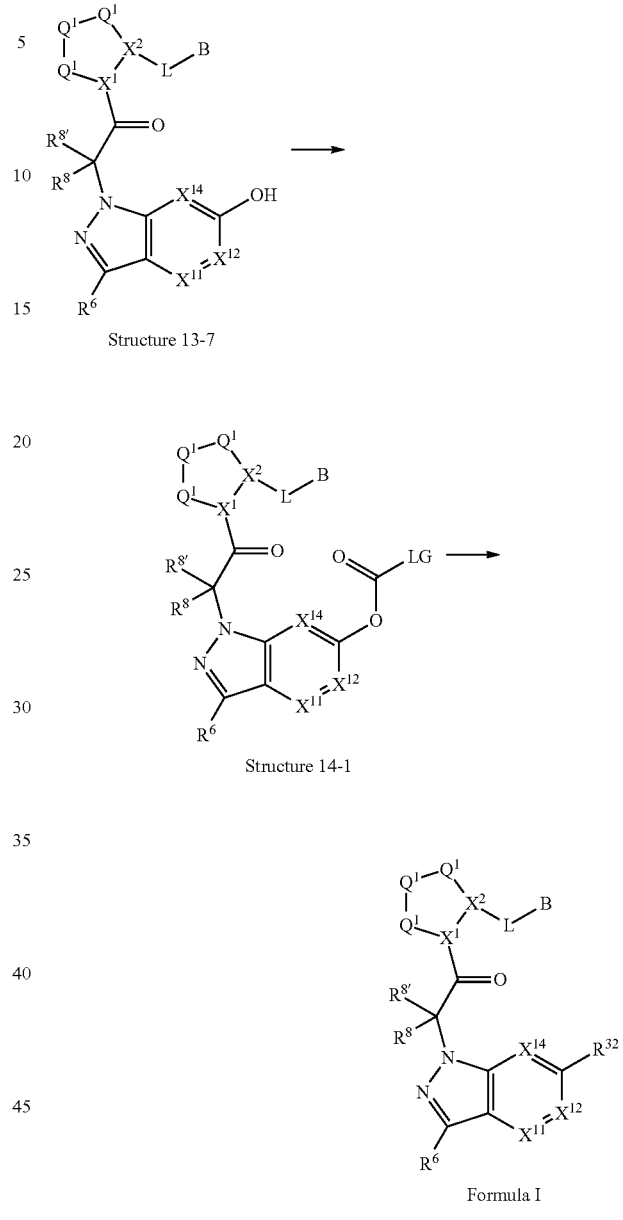

Structure 13-7, from Route 13, is activated with a carbonate group to generate Structure 14-1. In one embodiment, the leaving group is p-nitrophenol. The carbonate, Structure 14-1, is treated with an amine to generate compounds of Formula I wherein $R^{32}$ is —OC(O)NR$^{21}$R$^{22}$, —OC(O)NR$^{24}$R$^{25}$, or —OC(O)NR$^9$(CH$_2$)$_{1-4}$P(O)(OR$^{21}$)(OR$^{22}$). The chemistry is illustrated in Route 14. In some embodiments, Structure 13-7 is treated with an acid chloride or anhydride to generate compounds of Formula I wherein $R^{32}$ is —OC(O)(CH$_2$)$_{1-4}$R$^{21}$.

In one embodiment, Structure 15-1 is acylated to generate Structure 15-2. In alternate embodiment, Structure 15-1 is treated with an inorganic cyanide and organometallic catalyst to generate $R^6$=cyano. The cyano group can be treated with an oxime to generate an amide, —C(O)NH$_2$ at the $R^6$ position. Structure 15-2 is coupled to Structure 15-3 to generate Structure 15-4. In one embodiment, the leaving group, LG, is a halide. Structure 15-4 is treated with an acid to generate Structure 15-5. In some embodiments, the acid is trifluoroacetic acid. Structure 15-5 is treated with a base and a sulfoxide to generate Struture 15-6. In one embodiment, the sulfoxide is dimethyl sulfoxide. In one embodiment, the base is lithium bis(trimethylsilyl)amide. Compound 15-6 is coupled with Structure 3 from Route 1 to generate compounds of Formula I. This chemistry is illustrated in Route 15.

Route 15

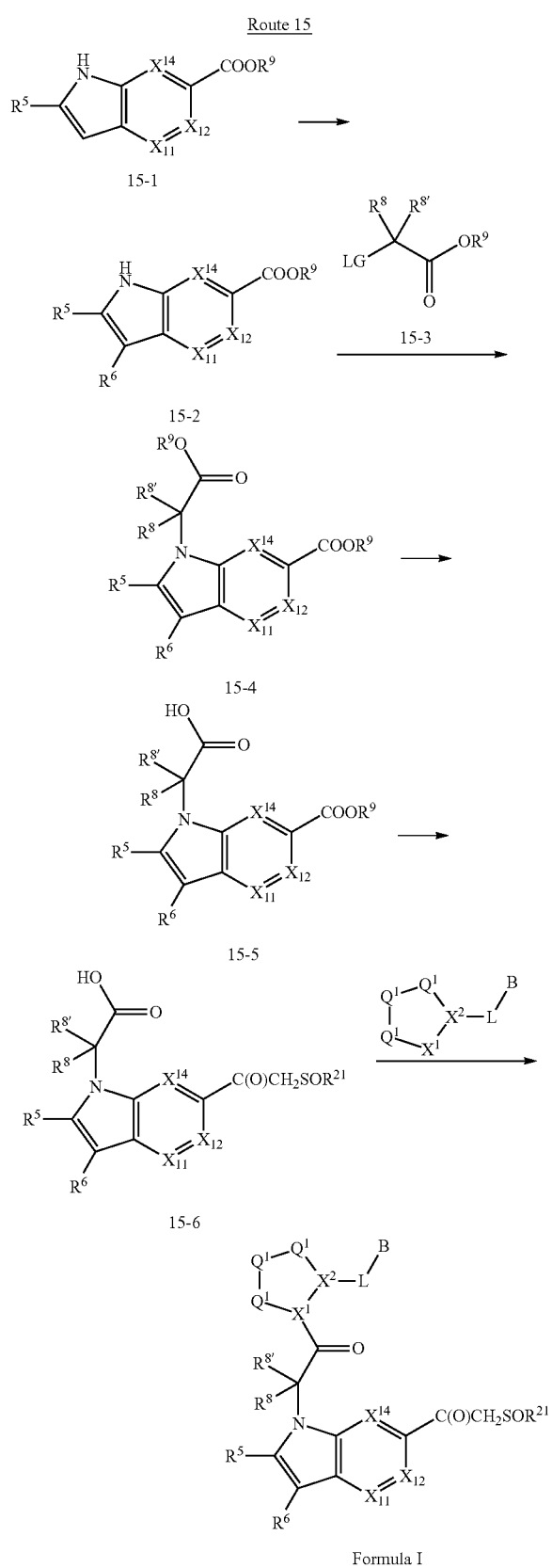

In one embodiment, Structure 16-1 is acylated to generate Structure 16-2. In an alternate embodiment, Structure 16-1 is treated with an inorganic cyanide and organometallic catalyst to generate $R^6$=cyano. The cyano group can be treated with an oxime to generate an amide, —C(O)NH$_2$ at the $R^6$ position. Structure 16-2 is coupled to Structure 16-3 to generate Structure 16-4. In one embodiment, the leaving group, LG, is a halide. Structure 16-4 is treated with an acid to generate Structure 16-5. In some embodiments, the acid is trifluoroacetic acid. Structure 16-5 is treated with a base and a sulfoxide to generate compound 16-6. In one embodiment, the sulfoxide is dimethyl sulfoxide. In one embodiment, the base is lithium bis(trimethylsilyl)amide. Compound 16-6 is coupled with Structure 3 from Route 1 to generate compounds within Formula I. This chemistry is illustrated in Route 16.

Route 16

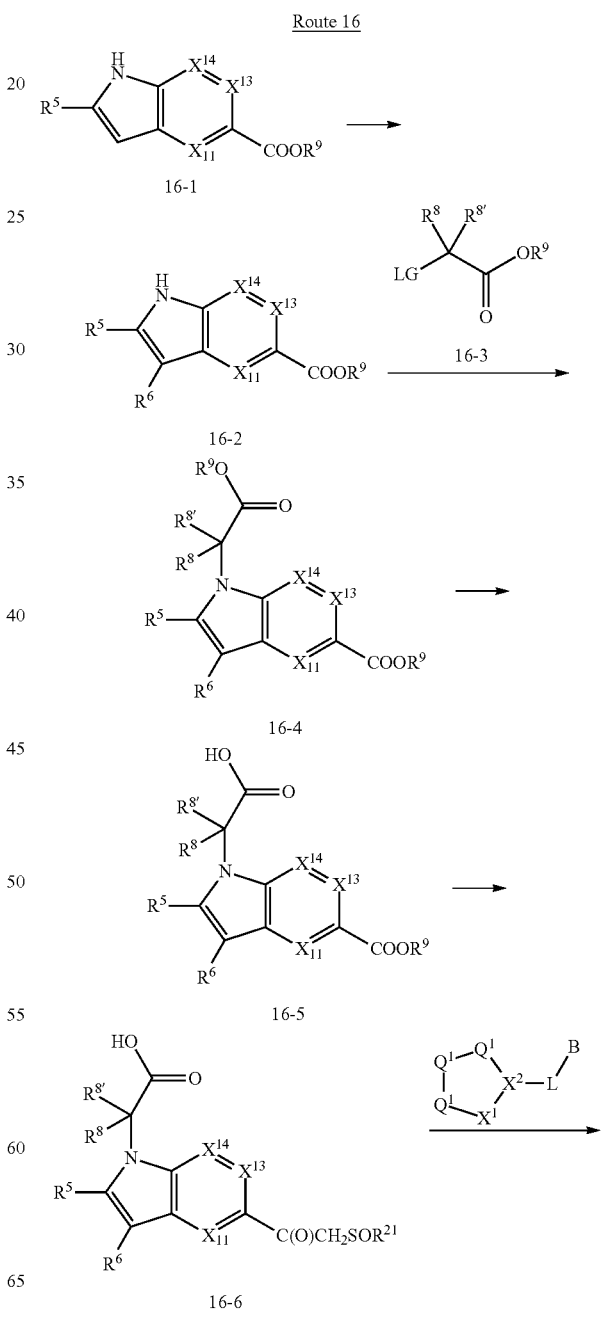

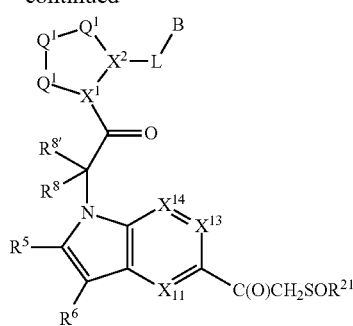

Formula I

In one embodiment, Structure 17-1 is acylated to generate Structure 17-2. In alternate embodiment, Structure 17-1 is treated with an inorganic cyanide and organometallic catalyst to generate $R^6$=cyano. The cyano group can be treated with an oxime to generate an amide, —C(O)NH$_2$ at the $R^6$ position. Structure 17-2 is coupled to Structure 17-3 to generate Structure 17-4. In one embodiment, the leaving group, LG, is a halide. Structure 17-4 is treated with an acid to generate Structure 17-5. In some embodiments, the acid is trifluoroacetic acid. Structure 17-5 is treated with a base and a sulfoxide to generate compound 17-6. In one embodiment, the sulfoxide is dimethyl sulfoxide. In one embodiment, the base is lithium bis(trimethylsilyl)amide. Compound 17-6 is coupled with Structure 3 from Route 1 to generate compounds of Formula I. This chemistry is illustrated in Route 17.

In one embodiment, Structure 18-1 is acylated to generate Structure 18-2. In alternate embodiment, Structure 18-1 is treated with an inorganic cyanide and organometallic catalyst to generate $R^6$=cyano. The cyano group can be treated with an oxime to generate an amide, —C(O)NH$_2$ at the $R^6$ position. Structure 18-2 is coupled to Structure 18-3 to generate Structure 18-4. In one embodiment, the leaving group, LG, is a halide. Structure 18-4 is treated with an acid to generate Structure 18-5. In some embodiments, the acid is trifluoroacetic acid. Structure 18-5 is treated with a base and a sulfoxide to generate compound 18-6. In one embodiment, the sulfoxide is dimethyl sulfoxide. In one embodiment, the base is lithium bis(trimethylsilyl)amide. Compound 18-6 is coupled with Structure 3 from Route 1 to generate compounds of Formula I. This chemistry is illustrated in Route 18.

EXAMPLE 2
Examples of Central Synthons
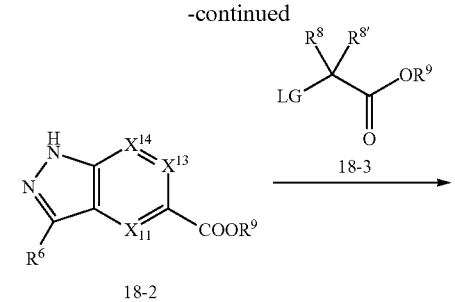
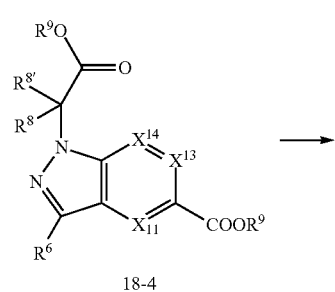
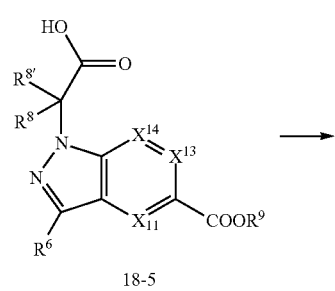
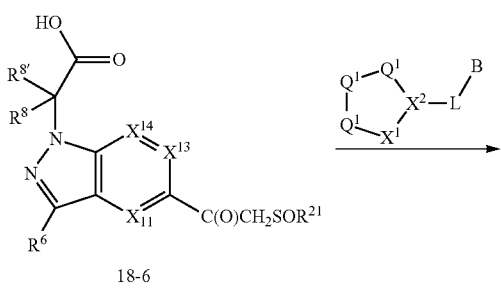
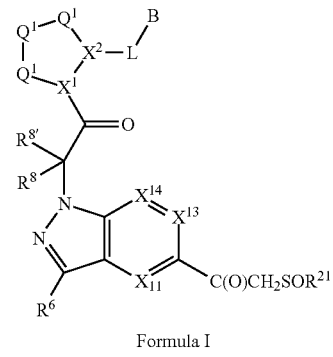
Formula I
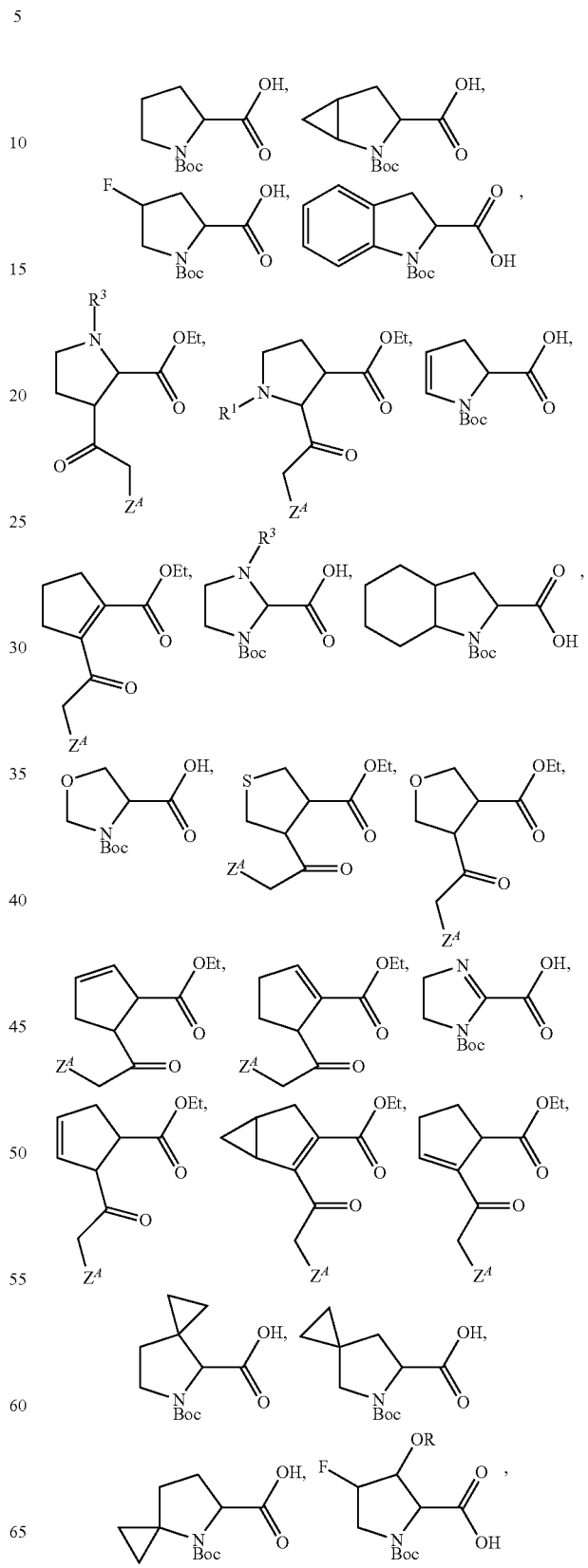

-continued
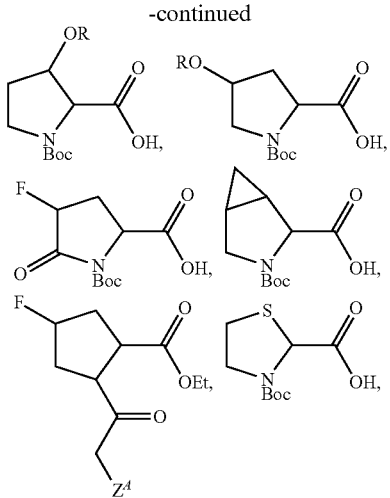
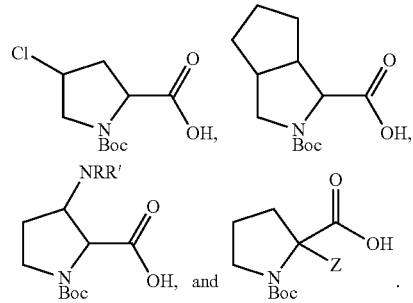
$Z^A$ is halogen.
In one embodiment, deuterated L-proline synthons are disclosed. Deuterated synthons include, but are not limited to, for example, the following compounds:
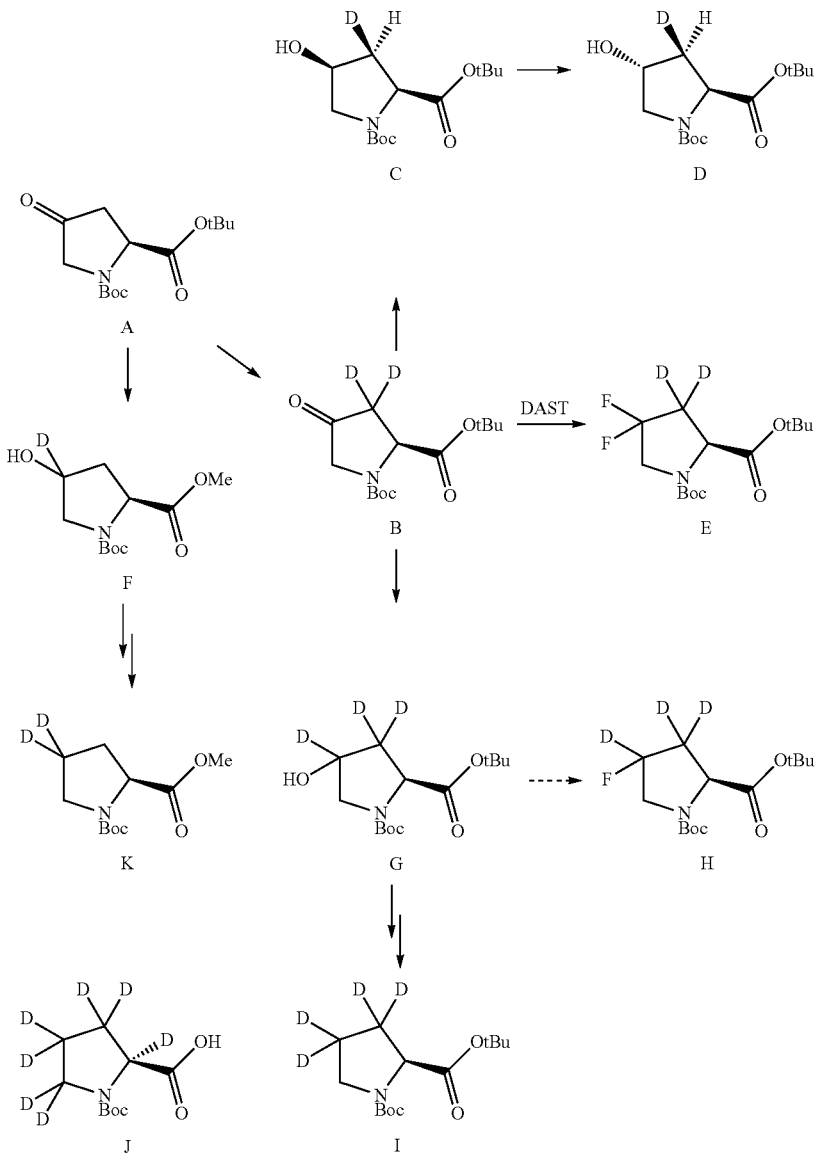

Structure A can be treated with deuterium oxide to generate Structure B. See, Barraclough, P. et al. Tetrahedron Lett. 2005, 46, 4653-4655; Barraclough, P. et al. Org. Biomol. Chem. 2006, 4, 1483-1491 and WO 2014/037480 (p.103). Structure B can be reduced to generate Structure C. See, Barraclough, P. et al. Tetrahedron Lett. 2005, 46, 4653-4655; Barraclough, P. et al. Org. Biomol. Chem. 2006, 4, 1483-1491. Structure C can be treated with Mitsunobu reaction conditions to generate Structure D. Structure B can be treated with DAST to generate Structure E. See, WO 2014/037480. Structure A can be treated with sodium borodeuteride to generate Structure F. See, Dormoy, J.- R.; Castro, B. *Synthesis* 1986, 81-82. Compound F can be used to generate Structure K. See, Dormoy, J.- R.; Castro, B. *Synthesis* 1986, 81-82. Structure B can be treated with a deuterated reducing agent, for example sodium borodeuteride to generate Structure G. Structure G can be treated with DAST to generate Structure H. Structure F can be used to generate Structure K. See, Dormoy, J.- R.; Castro, B. *Synthesis* 1986, 81-82. Structure G can be used to generate Structure I. Structure J can be prepared according to Hruby, V. J. et al. *J. Am. Chem. Soc.* 1979, 101, 202-212. Structures A-J can be used to prepare compounds of Formula I.

EXAMPLE 3

Preparation of Central-L-B Synthons

Routes 1a, 1b and 1c.

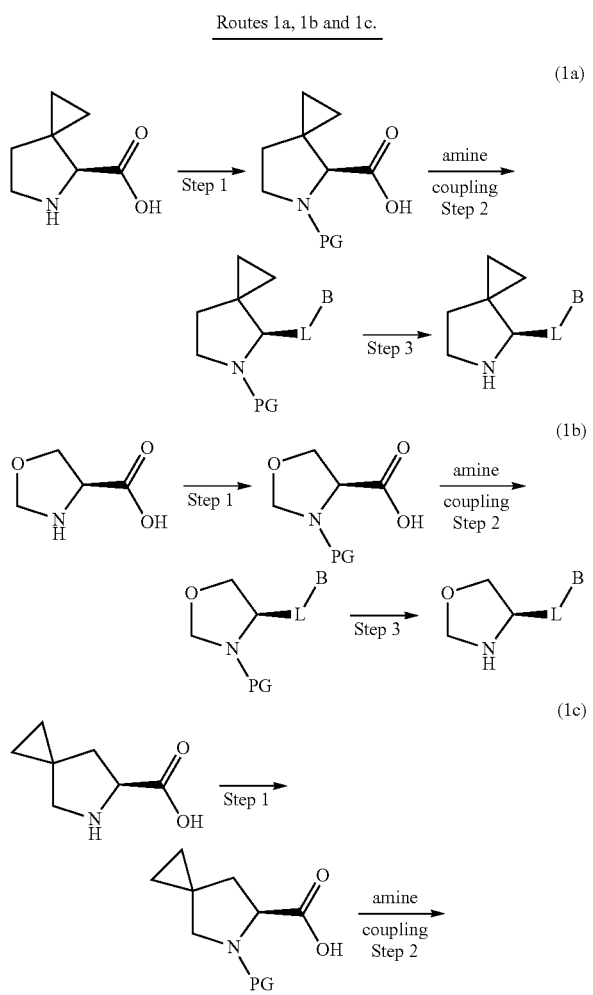

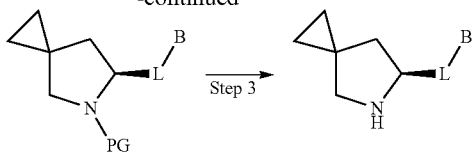

In Route 1a, 5-azaspiro[2.4]heptane-4,5-dicarboxylic acid, 5-(1,1-dimethylethyl) ester, (4S)-, CAS 209269-08-9, can be prepared as described in Tandon, M. et al. Bioorg. Med. Chem. Lett. 1998, 8, 1139-1144. In Step 2, the protected azaspiro[2.4]heptane is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1b, (4S) 4-oxazolidinecarboxylic acid, hydrochloride is treated with an amine protecting reagent. In one embodiment, the amine protecting reagent is di-tert-butyl dicarbonate. In another embodiment, 3,4-oxazolidinedicarboxylic acid, 3-(1,1-dimethylethyl) ester, (4S)-, is commercially available from JPM2 Pharmaceuticals. In one embodiment the reaction is carried out in an organic solvent in the presence of a base. In one embodiment, the organic solvent is acetonitrile. In one embodiment, the base is 4-dimentylaminopyridine (DMAP). In Step 2, the protected 4-oxazolidinecarboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1c, (S)-5-(tert-Butoxycarbonyl)-5-azaspiro[2.4] heptane-6-caboxylic acid, CAS 1129634-44-1, is commercially available from Ark Pharm. In Step 2, the carboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

Routes 2a, 2b, 2c and 2d.

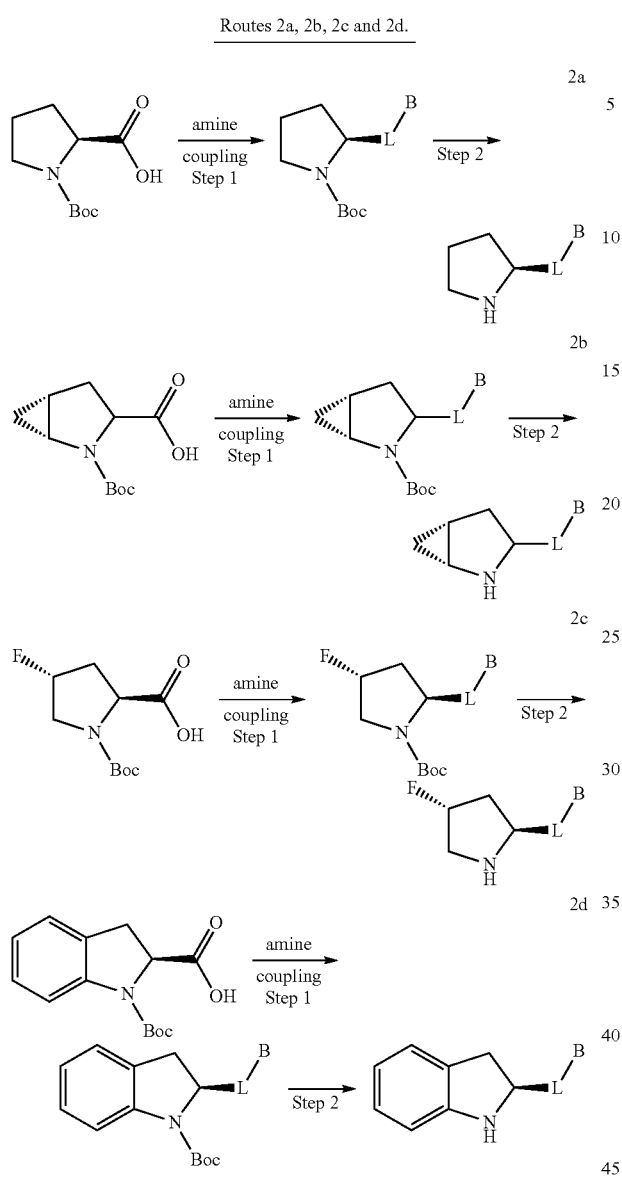

In Route 2a, commercially available Boc-L-proline is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2b, commercially available (1R, 3S, 5R)-2-[(tert-butoxy)carbonyl]-2-azabicyclo[3.1.0]hexane-3-carboxylic acid, from Enamine, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2c, commercially available (2S,4R)-1-(tert-butoxycarbonyl)-4fluoropyrrolidine-2-carboxylic acid, from Manchester Organics, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2d, commercially available (S)-1-(tert-butoxycarbonyl)indoline-2-carboxylic acid, from Chem-Impex, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane. This chemistry is illustrated in Scheme 2.

Additional starting materials that can readily be converted to Central-L-B-Synthons include, but are not limited to: (S)-1-(tert-butoxycarbonyl)-2,3-dihydro-1H-pyrrole-2-carboxylic acid, CAS 90104-21-5, available from Ark Pharm; cyclopent-1-ene-1,2-dicarboxylic acid, CAS 3128-15-2, purchased from Ark Pharm; imidazole, 1H-imidazole-1,2-dicarboxylic acid, 1-(1,1-dimethylethyl) 2-ethyl ester, CAS 553650-00-3, commercially available from FCH Group; Boc-L-octahydroindole-2-carboxylic acid can be purchased from Chem Impex. The compound,

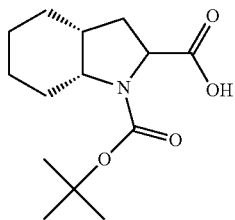 [SMILES: CC(C)(C)OC(=O)N1C(C(=O)O)C[C@H]2CCCC[C@H]21]

can be prepared according to the procedures disclosed in WO 2004/111041; (S)-Boc-5-oxopyrrolidine-2-carboxylic acid is available from the Aldrich Chemical Co.; (1S,2S, 5R)-3-(tert-butoxycarbonyl)-3-azabicyclo[3.3.0]hexane-2-carboxylic acid is available from Ark Pharm; (S)-3-Boc-thiazolidine-2-carboxylic acid is available from Alfa Aesar; (2S,4R)-1-(tert-butoxycarbonyl)-4-chloropyrrolidine-2-carboxylic acid is available from Arch Bioscience; (1S,3aR, 6aS)-2-(tert-butoxycarbonyl)octahydrocyclopenta[c]pyrrole-1-carboxylic acid is available from Ark Pharm; 1,2-pyrrolidinedicarboxylic acid, 3-[[(phenylmethoxy)carbonyl]

amino]-, 1-(1,1-dimethylethyl) ester, (2S,3R) can be prepared as disclosed in WO 2004/007501. The Cbz group can be removed and the amino group can be alkylated to generate central core compounds of the present invention.

The compound

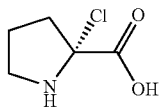

can be prepared as disclosed by Braun, J. V.; Heymons, Albrecht Berichte der Deutschen Chemischen Gesellschaft [Abteilung] B: Abhandlungen (1930) 63B, 502-7.

The compounds (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester can be prepared as a mixture according to WO 2012/093101 to Novartis and the regioisomers can be ultimately separated once coupled to generate the central core-L-B synthons. The compound (S)-Boc-5-oxopyrrolidine-2-carboxylic acid is available from the Aldrich Chemical Co.

EXAMPLE 4

Synthesis of Intermediates 4A. (2S,4R)-Tert-Butyl 2-((3-Chloro-2-Fluorobenzyl)Carbamoyl)-4-Fluoropyrrolidine-1-Carboxylate.

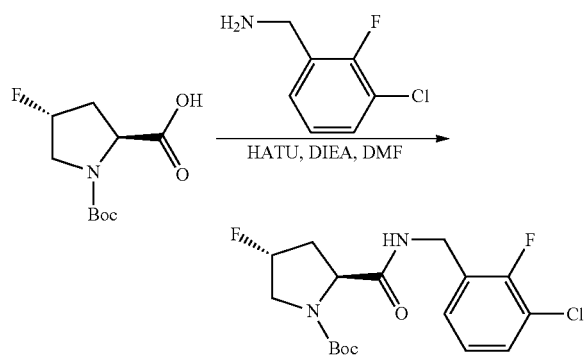

(2S,4R)-1-(tert-butoxycarbonyl)-4-fluoropyrrolidine-2-carboxylic acid (2.33 gm, 10 mmol) was dissolved in DMF (50 ml) and $^i$Pr2NEt (8.6 ml, 5 eq.) was added, followed by the addition of (3-chloro-2-fluorophenyl) methanamine (3.18 gm 20 mmol) at 5° C. Then HATU (8 gm, 2.1 eq) was added slowly at same temperature. The reaction mixture was then stirred for 18 h at RT. After completion of the reaction monitored by HPLC, the reaction mixture was diluted with 1M citric acid solution (200 ml+NaCl solid 20 gm) and extracted with DCM (150 mL×2), the organic layer was then washed with an aqueous solution of NaHCO₃ (100 ml) and washed with water (100 ml), brine (100 ml) and dried over Na₂SO₄ and concentrated under reduced pressure. The remaining residue was purified by column chromatography (eluted with DCM/EtOAc) to give (2S,4R)-tert-butyl 2-((3-chloro-2-fluorobenzyl)carbamoyl)-4-fluoropyrrolidine-1-carboxylate.

4B. (2S,4R)-N-(3-Chloro-2-Fluorobenzyl)-4-Fluoropyrrolidine-2-Carboxamide Hydrochloride (A).

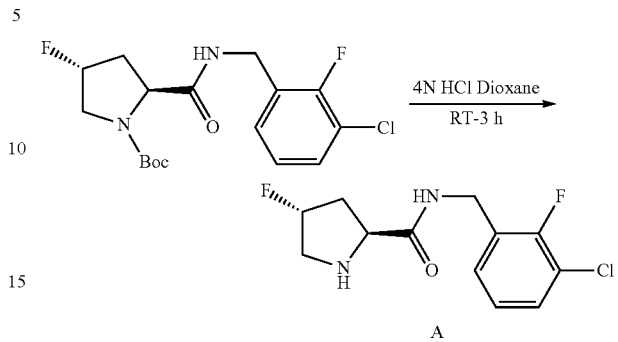

(2S,4R)-tert-butyl 2-((3-chloro-2-fluorobenzyl)carbamoyl)-4-fluoropyrrolidine-1-carboxylate (500 mg,) was taken in 4N HCl dioxane (30 ml ) and resulting reaction mixture was stirred at rt for 3 h. After completion of the reaction monitored by HPLC solvent was removed under reduced pressure. The residue, A, was used for next reaction.

4C. 2-(3-Acetyl-1H-Indol-1-Yl)Acetic Acid (B)

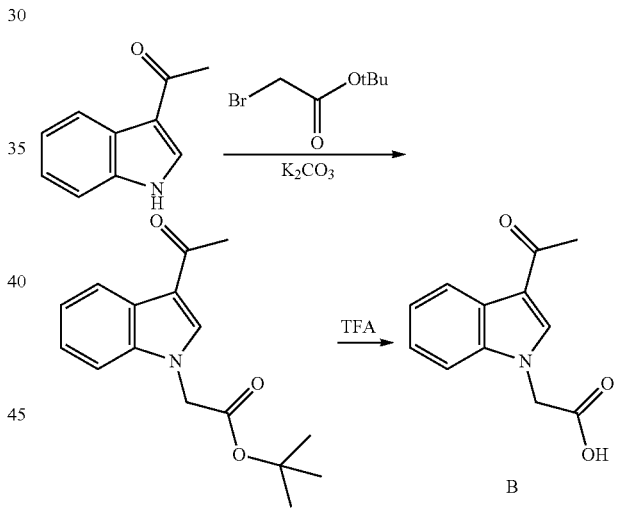

A mixture of 3-Acetylindole (10.09 g) and t-butylbromoacetate (13.71 g) were reflux in acetonitrile in presence of potassium carbonate (9.7 g) for 24 h. The reaction mixture was cooled to room temperature and filtered and evaporated to dryness. The residue was purified by chromatography over silica gel and eluted with a mixture of ethyl acetate in methylene chloride to afford tert-butyl 2-(3-acetyl-1H-indol-1-yl)acetate.

Tert-butyl 2-(3-acetyl-1H-indol-1-yl)acetate was stirred overnight in a mixture of trifluoroacetic acid in methylene chloride and diluted with methanol and evaporated to dryness. The residue was treated with 1M sodium hydroxide and extracted with methylene chloride. The aqueous layer was acidified with 6M HCl and the residue filtered, washed with water and dried to give 2-(3-acetyl-1H-indol-1-yl) acetic acid (B).

4D. 1-(3-Amino-1H-Indol-1-Yl)Ethanone Hydrochloride (C).

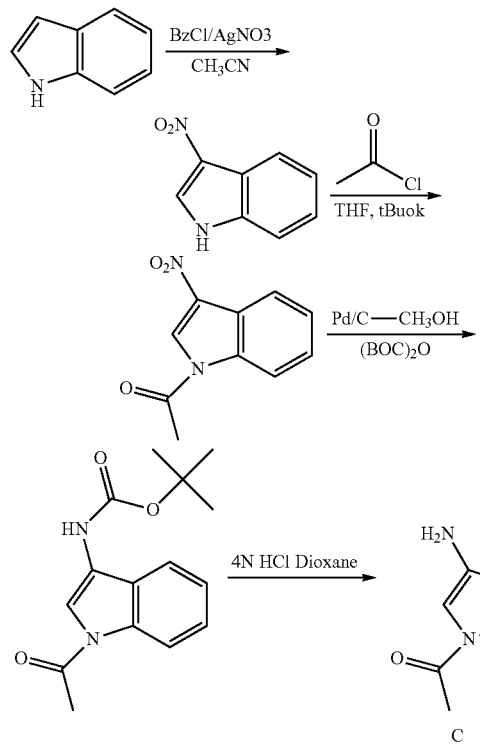

To a stirred solution of AgNO₃ (9.3 g, 1.07 equiv) in acetonitrile was added benzoyl chloride (7.47 g, 1.04 equiv) dropwise at 0° C. The mixture was stirred for 10 min, and then solution of 1H-indole (6 g, 1 equiv) in acetonitrile was added at 0° C. and stirred for 1 h at RT. The reaction mixture was poured into ice to get a dark brown precipitate. The precipitate was filtered washed with water dried. The crude residue was purified by flash column chromatography (ISCO with hexanes/EtOAc) to give 3-nitro-1H-indole.

A stirred solution of 3-nitro-1H-indole (1 g, 1 equiv) in dry THF was cooled to 5° C. Then tBuOK (830 mg, 1.2 equiv) was added slowly, and the resulting mixture was stirred 10 min. Acetyl chloride (525 mg, 1.2 equiv) was added and the reaction mixture was stirred for 30 min. After completion of the reaction as monitored by HPLC, solvent was removed under reduced pressure, diluted with DCM washed with an aqueous solution of NaHCO₃. The organic layer was separated washed with brine and concentrated under reduced pressure. The remaining residue was purified by flash column chromatography (ISCO eluted with DCM/EtOAc) to give 1-(3-nitro-1H-indol-1-yl)ethanone.

To a mixture of 1-(3-nitro-1H-indol-1-yl)ethanone (600 mg, 2.942 mmol) and di-tert-butyl dicarbonate (1.925 g, 8.826 mmol) in methanol (50 mL) was added 5% Pd/C (20 mg). The resulting reaction mixture was stirred under hydrogen 24 h, after completion of the reaction Pd/C was filtered using celite, and the filtrate was concentrated under reduced pressure. The remaining residue was purified by flash column chromatography (ISCO eluted with DCM/EtOAc) to give tert-butyl (1-acetyl-1H-indol-3-yl)carbamate.

Tert-butyl (1-acetyl-1H-indol-3-yl) carbamate (300 mg, 1.1 mmol) was taken in 4N HCl dioxane (10 ml) and resulting reaction mixture was stirred at rt for 3 h. After completion of the reaction solvent was removed under reduced pressure. This material, 1-(3-amino-1H-indol-1-yl) ethanone hydrochloride (C), was used directly in the next synthetic step.

4E. 2-(3-Acetyl-6-Hydroxy-1H-Indol-1-Yl)Acetic Acid (D)

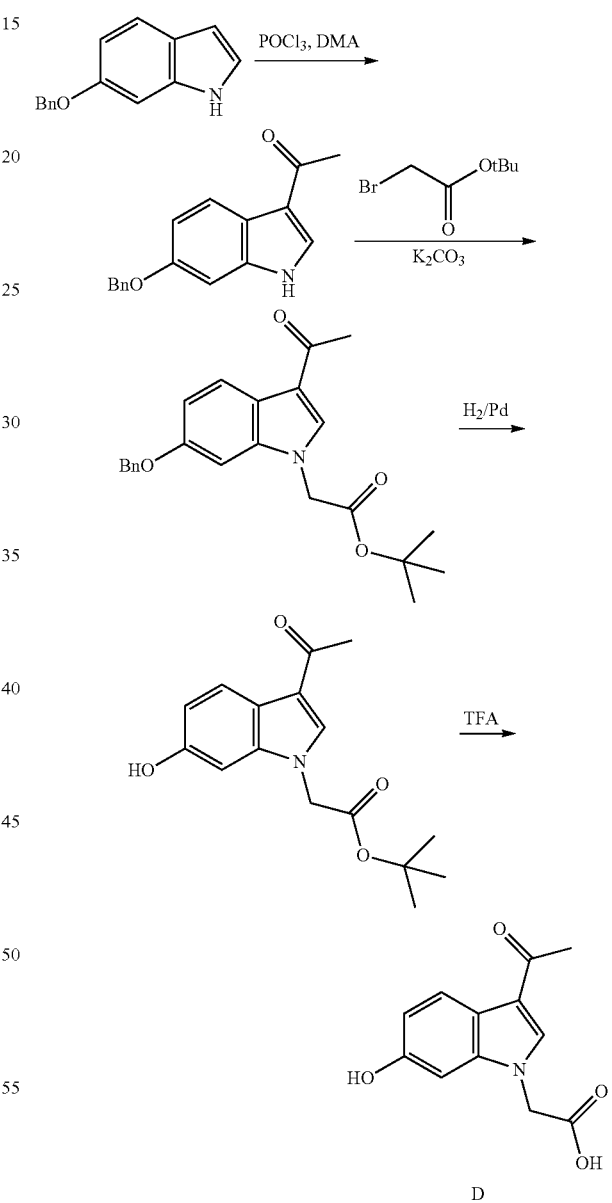

6-Benzyloxyindole was acetylated using reported procedure (Eur. J. Med Chem., (2011), 46, 756) and alkylated following the procedure describe for compound B. The benzyl group was removed by hydrogenation over palladium on charcoal and the t-butyl group removed again as described for compound B.

4F. 2-(3-Acetyl-5-Hydroxy-1H-Indol-1-Yl)Acetic Acid (E).

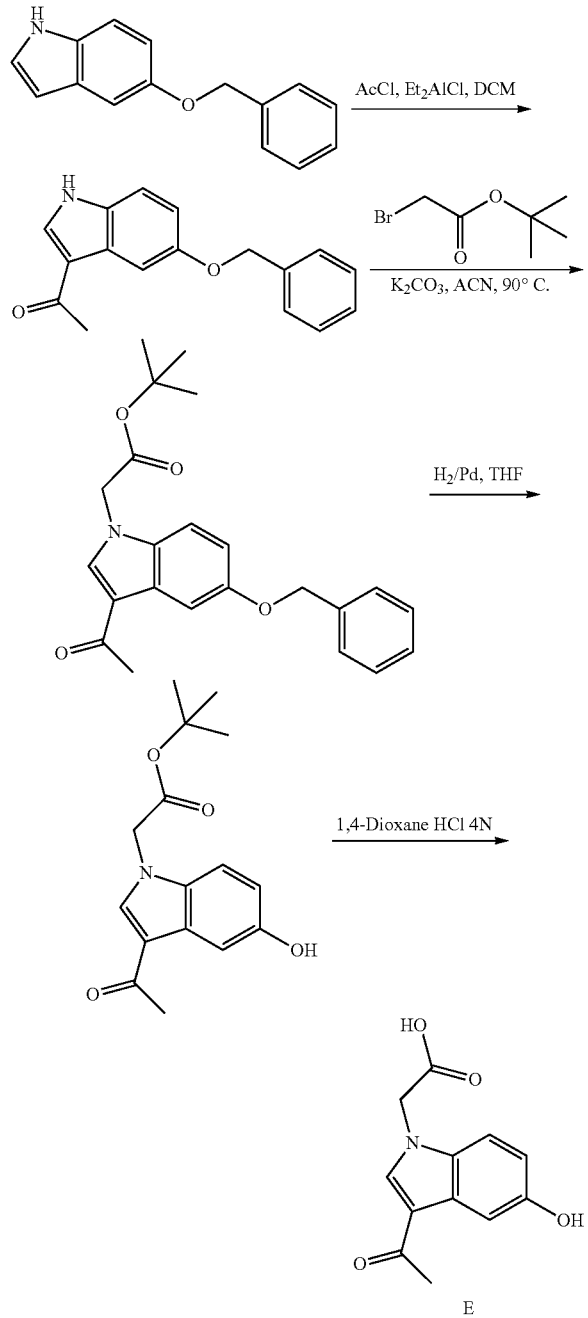

To a stirred solution of 5-(benzyloxy)-1H-indole (11.08 g, 1 equiv) in 200 mL DCM was added diethylaluminium chloride (1 M solution in Hexane; 74.6 mL, 1.5 equiv) drop wise at 0° C. The mixture was stirred for 30 min, and then a solution of acetyl chloride (5.3 mL, 1.5 equiv) in 150 mL DCM was added at 0° C. and the reaction was stirred for 1 h at 0° C. A 5% aqueous citric acid solution was added at 0° C. and the reaction was stirred for 15 min at RT. The precipitate was filtered and washed with water, and the organic filtrate was dried and concentrated under reduced pressure. The residue was purified by flash column chromatography (silica gel eluted with DCM/CH$_3$OH) to give 1-(5-(Benzyloxy)-1H-indol-3-yl)ethanone.

To a suspension of 1-(5-(benzyloxy)-1H-indol-3-yl)ethanone (6.5 gm, 1 equiv) and K$_2$CO$_3$ (3.72 gm, 1.1 equiv) in 50 mL acetonitrile was added tert-butyl 2-bromoacetate (3.92 mL, 1.1 equiv) dropwise at RT. The resulting mixture was then heated to reflux for 18 h. After cooling to RT, the mixture was diluted with DCM (100 mL), and then filtered through the celite pad; filtrate was concentrated under reduced pressure. The remaining residue was purified by flash column chromatography (silica gel eluted with DCM/EtOAc) to give tert-Butyl 2-(3-acetyl-5-(benzyloxy)-1H-indol-1-yl)acetate.

To tent-Butyl 2-(3-acetyl-5-(benzyloxy)-1H-indol-1-yl) acetate (6 g) in THF (80 mL) was added Pd/C (0.05 equiv). The reaction mixture was stirred at RT for 5 h under H$_2$ (1 atm). The reaction mixture was then filtered through a pad of Celite and washed with CH$_2$Cl$_2$ and MeOH. The filtrate was concentrated under reduced pressure and the remaining residue was purified by flash column chromatography (silica gel eluted with DCM/EtOAc) to give tent-Butyl 2-(3-acetyl-5-hydroxy-1H-indol-1-yl)acetate.

Tert-Butyl 2-(3-acetyl-5-hydroxy-1H-indol-1-yl)acetate (814 mg, 2.8 mmol) was taken up in 4 N HCl dioxane (10 mL) and the resulting reaction mixture was stirred at RT for 48 h. The solvent was then removed under reduced pressure to give 2-(3-acetyl-5-hydroxy-1H-indol-1-yl)acetic acid (E) which could be used directly in the next synthetic step.

EXAMPLE 5

Synthesis of 3-Acetyl-1-(2-((2S,4R)-2-((3-Chloro-2-Fluorobenzyl)Carbamoyl)-4-Fluoropyrrolidin-1-Yl)-2-Oxoethyl)-1H-Indol-5-Yl Cyclopropylcarbamate

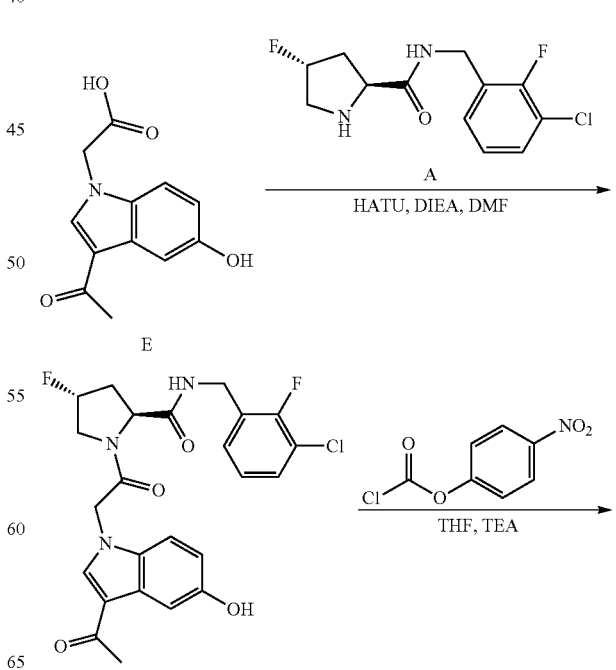

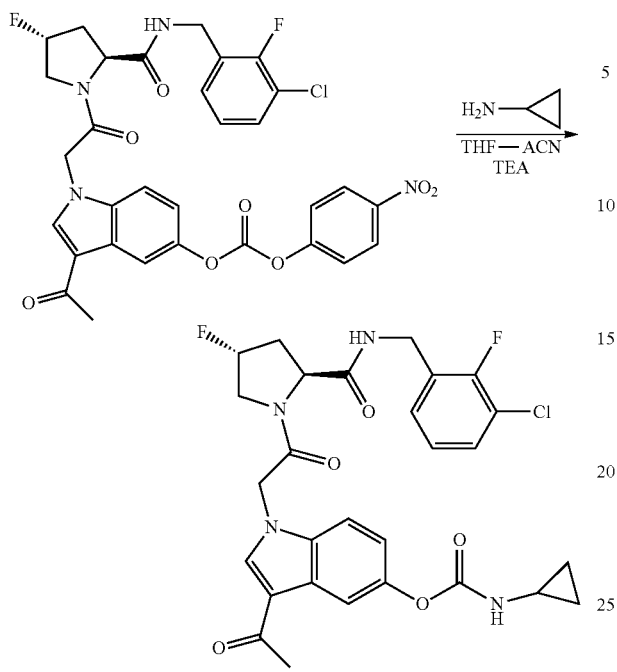

2-(3-acetyl-5-hydroxy-1H-indol-1-yl)acetic acid (2.8 mmol) E was dissolved in DMF (20 mL) and ᶦPr2NEt (2.076 mL, 5 equiv) was added, followed by the addition of (2S,4R)-N-(3-chloro-2-fluorobenzyl)-4-fluoropyrrolidine-2-carboxamide hydrochloride A (788 mg, 2.54 mmol) at 5° C. HATU (2.026 g, 2.1 equiv) was then added slowly at the same temperature and the reaction mixture was stirred for 18 h at RT. The reaction mixture was then diluted with 1 M citric acid solution (100 mL, containing 10 g NaCl) and extracted with DCM (2×50 mL). The organic layer was washed with an aqueous solution of NaHCO₃ (40 mL), washed with water (40 mL), washed with brine (40 mL), dried over Na₂SO₄, and concentrated under reduced pressure. The remaining residue was purified by flash column chromatography (silica gel eluted with DCM/EtOAc) to give (2S,4R)-N-(3-chloro-2-fluorobenzyl)-1-(2-(3-acetyl-5-hydroxy-1H-indol-1-yl)acetyl)-4-fluoropyrrolidine-2-carboxamide.

(2S,4R)-N-(3-chloro-2-fluorobenzyl)-1-(2-(3-acetyl-5-hydroxy-1H-indol-1-yl)acetyl)-4-fluoropyrrolidine-2-carboxamide (220 mg, 1 equiv) was dissolved in THF (20 mL) and NEt₃ (100 µl, 1.7 equiv) was added, followed by the addition of 4-nitrophenyl chloroformate (136 mg, 1.5 equiv) at 0° C. The reaction mixture was then stirred for 18 h at RT, diluted with 5 mL water, and extracted with ethyl acetate (50 mL). The organic layer was dried over Na₂SO₄ and concentrated under reduced pressure. The remaining residue was purified by flash column chromatography (silica gel eluted with DCM/EtOAc) to give 3-Acetyl-1-(2S,4R)-2-((3-chloro-2-fluorobenzyl)carbamoyl)-4-fluoropyrrolidin-1-yl)-2-oxoethyl)-1H-indol-5-yl (4-nitrophenyl) carbonate.

3-Acetyl-1-(2-((2S,4R)-2-((3-chloro-2-fluorobenzyl)carbamoyl)-4-fluoropyrrolidin-1-yl)-2-oxoethyl)-1H-indol-5-yl (4-nitrophenyl) carbonate was dissolved in a mixture of THF (5 mL), ACN (5 mL), and cyclopropanamine (12.86 µl, 2 equiv), followed by the addition of NEt₃ (30 µl, 3 equiv) at 0° C. The reaction mixture was then stirred for 24 h at RT. The reaction mixture was then concentrated under reduced pressure and the remaining residue was purified by flash column chromatography (silica gel eluted with DCM/CH₃OH) to give (2S,4R)-N2-(1-acetyl-1H-indol-3-yl)-N1-(3-chloro-2-fluorobenzyl)-4-fluoropyrrolidine-1,2-dicarboxamide. ¹H NMR (400 MHz, DMSO-d₆, 300 K): (major rotamer) δ 0.53 (s, br, 2H), 0.65 (d, J=5.6 Hz, 2H), 2.04-2.18 (m, 1H), 2.42 (s, 3H), 2.54-2.58 (m, 1H), 3.90 (ddd, J=22, 9.6, 3.2 Hz, 1H), 4.14 (dd, J=8.8, 12.4 Hz, 1H), 4.32 (dd, J=22.4, 6.0 Hz, 1H), 4.40-4.49 (m, 2H), 5.18 (d, J=17.2 Hz, 1H), 5.39 (d, J=17.2 Hz, 1H), 5.51 (d, J=52.8 Hz, 1H), 6.92-7.01 (m, 2H), 7.16-7.24 (m, 1H), 7.40-7.45 (m, 2H), 7.82-7.87 (m, 2H), 8.22 (s, 1H), 8.60 (t, J=5.6 Hz, 1H). ¹⁹F NMR (376 MHz, DMSO-d₆, 300 K): (major rotamer) δ -121.3, -176.1. LC (method 1): $t_R$=1.73 min. LC/MS (O) m/z: [M+H]⁺calcd for $C_{28}H_{27}ClF_2N_4O_5$, 573; found, 573.

EXAMPLE 6

Synthesis of (2S,4R)-1-(2-(3-Acetyl-6-(2-(Methylsulfinyl)Acetyl)-1H-Indol-1-Yl)Acetyl)-N-(3-Chloro-2-Fluorobenzyl)-4-Fluoropyrrolidine-2-Carboxamide

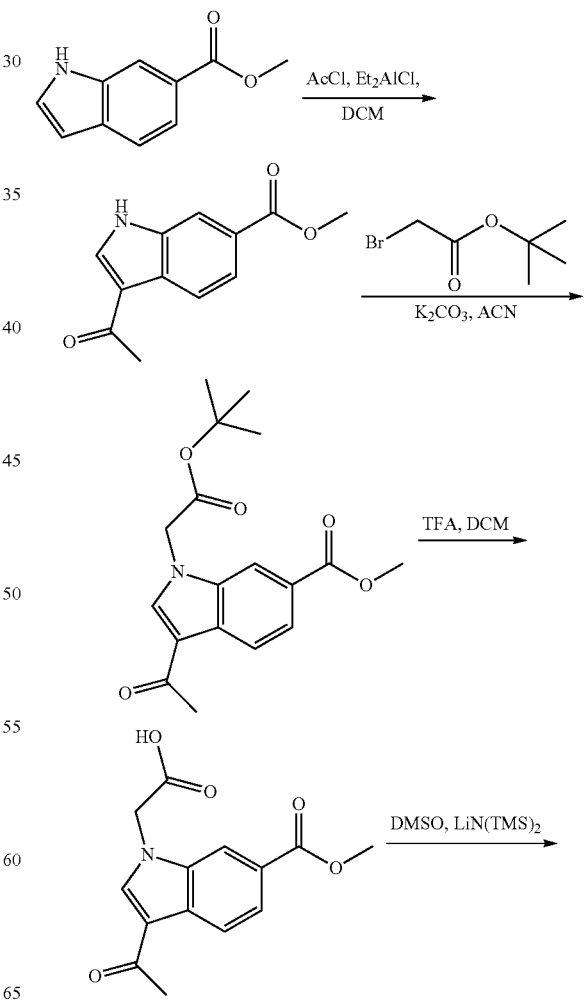

103
-continued

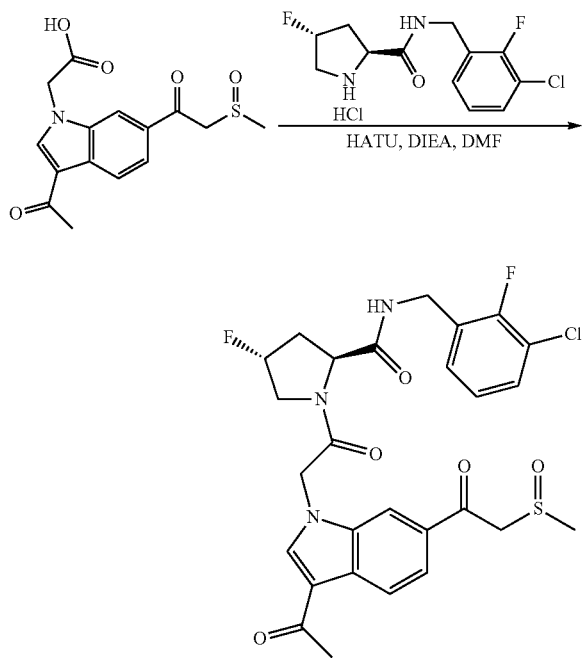

Into a solution of methyl 1H-indole-6-carboxylate (1.06 g) in DCM (20 ml), Et$_2$AlCl (1.0 M in Hexane, 9.09 ml) was added slowly at 0° C. under argon and stirring was continued for 30 min. A solution of acetyl chloride (0.653 ml) in DCM (20 ml) was added, and the mixture was stirred to rt overnight. The dark reaction mixture was poured in to 5% aq. citric acid solution (100 ml) at 0° C. and stirred. The precipitate was collected by filtration and dried to give methyl 3-acetyl-1H-indole-6-carboxylate (1.2 g).

A mixture of 3-acetyl-1H-indole-6-carboxylate (0.7 g) and tert-butyl 2-bromoacetate (0.52 ml) was refluxed in acetonitrile (15 ml) in the presence of K$_2$CO$_3$ (0.49 g) overnight. After cooled to rt, the solid was filtered off and the filtrate was concentrated. The residue was dissolved in DCM (30 ml) and washed with 1N HCl (5 ml), NaHCO$_3$ aq. (10 ml) and brine sequentially. After dried over anhydrous Na$_2$SO$_4$, the solvent was removed under reduced pressure to give methyl 3-acetyl-1-(2-(tert-butoxy)-2-oxoethyl)-1H-indole-6-carboxylate (1.04 g) as a gray colored solid.

3-Acetyl-1-(2-(tert-butoxy)-2-oxoethyl)-1H-indole-6-carboxylate (205 mg) in DCM (3 ml) was treated with TFA (3 ml) at rt for 4 hr. Volatiles were evaporated under vacuum to give 2-(3-acetyl-6-(methoxycarbonyl)-1H-indol-1-yl)acetic acid for the next step.

Into a flask charged with anhydrous DMSO (5 ml), lithium bis(trimethylsilyl)amide (2.0 M in THF, 5 ml) was added at rt with stirring. The mixture was cooled to 0° C., and then 2-(3-acetyl-6-(methoxycarbonyl)-1H-indol-1-yl)acetic acid from above in DMSO (5 ml) was added. The reaction mixture was stirred gradually to rt in 2 hr and cooled back to 0° C. Aqueous solution of citric acid (5%, 50 ml) was added to quench the reaction. NaCl was added to saturate the aq. and the pH was adjusted to ~2. AcOEt doped with 5% of 2,2,2-trifluoroethanol was used for extraction. Organic layer was dried over anhydrous Na$_2$SO$_4$, and the solvent was removed under reduced pressure. The residue was titrated with MeOH and filtered to give 2-(3-acetyl-6-(2-(methylsulfinyl)acetyl)-1H-indol-1-yl)acetic acid (66 mg).

Into a mixture of 2-(3-acetyl-6-(2-(methylsulfinyl)acetyl)-1H-indol-1-yl)acetic acid (66 mg) and (2S,4R)-N-(3-chloro-2-fluorobenzyl)-4-fluoropyrrolidine-2-carboxamide hydrochloride (64 mg) in DMF (1 ml), HATU (0.117 g) followed by DIEA (0.174 ml) was added. After stirred at rt for 2h, water (10 ml) was added and extacted with AcOEt (20 ml). Crude obtained after evaporation of solvent was purified on ISCO with 10% of MeOH in DCM to give (2S,4R)-1-(2-(3-acetyl-6-(2-(methylsulfinyl)acetyl)-1H-indol-1-yl)acetyl)-N-(3-chloro-2-fluorobenzyl)-4-fluoropyrrolidine-2-carboxamide (30 mg). $^1$H NMR (400 MHz, CDCl$_3$-MeOD, 300 K): (major rotamer) δ 2.15-2.37 (m, 1H), 2.60 (s, 3H), 2.75 (s, 3H), 3.95-4.15 (m, 1H), 4.50-4.70 (m, 3H), 5.10-5.25 (m, 2H), 5.45 (d, J=52.8 Hz, 1H), 6.70-6.80 (m, 1H), 7.14-7.2 (m, 2H), 7.84-8.18 (s, 2H), 8.40 (s, 1H), 8.39-8.42 (m, 2H). LC (method 1): $t_R$=1.35 min. LC/MS (EI) m/z: calcd for C$_{27}$H$_{26}$ClF$_2$N$_3$O$_5$S, 577; found, [M+H]$^+$578.

EXAMPLE 7

Additional Syntheses of Non-Limiting Examples of Compounds of Formula I

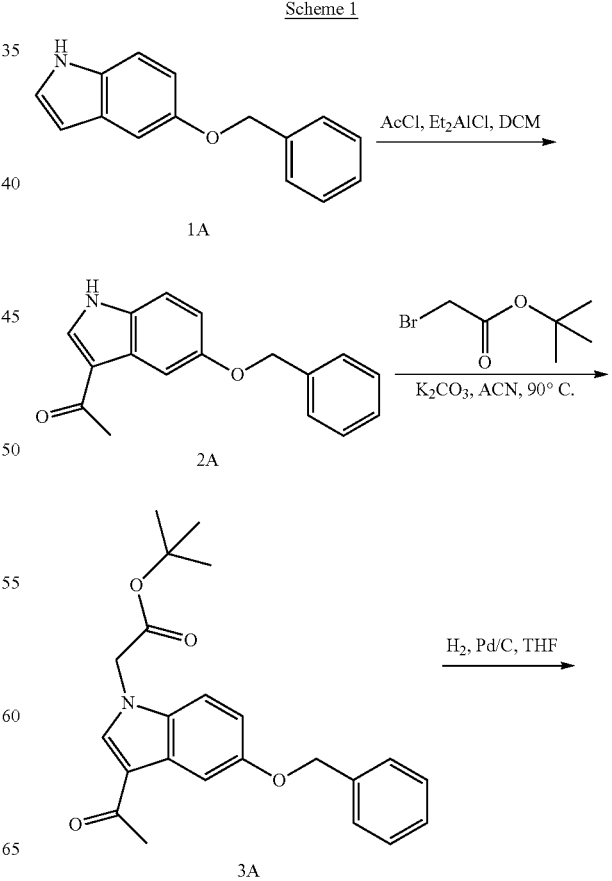

105
-continued

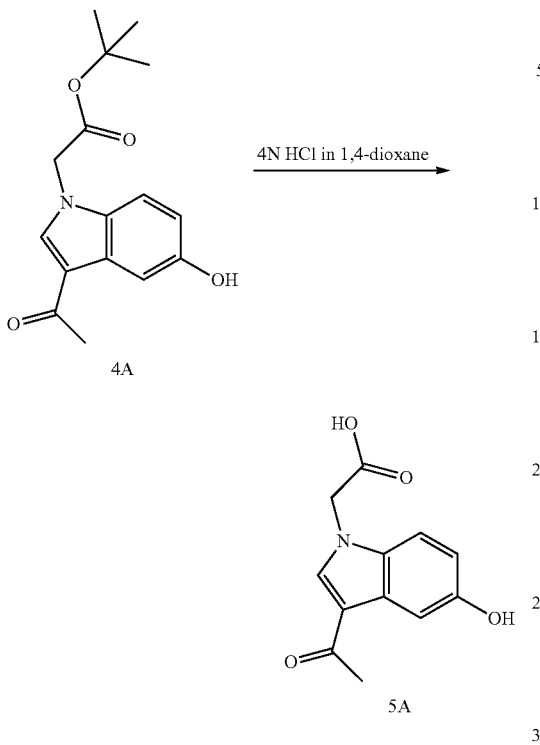

Compound 2A: 1-(5-(Benzyloxy)-1H-indol-3-yl) ethanone.

To a stirred solution of 5-(benzyloxy)-1H-indole (11.08 g, 1 equiv) in DCM (200 mL) was added diethylaluminium chloride (1 M solution in hexane; 74.6 mL, 1.5 equiv) dropwise at 0° C. The mixture was stirred for 30 min, and then a solution of acetyl chloride (5.3 mL, 1.5 equiv) in DCM (150 mL) was added at 0° C. and stirred for 1 h at this temperature. A 5% aq citric acid solution was added at 0° C. and the reaction mixture was stirred for 15 min at RT. The precipitate was collected by filtration, washed with water, and dried in vacuo to give 2A.

Compound 3A: tert-Butyl 2-(3-acetyl-5-(benzyloxy)-1H-indol-1-yl) acetate.

To a suspension of 1-(5-(benzyloxy)-1H-indol-3-yl)ethanone (6.5 g, 1 equiv) and $K_2CO_3$ (3.72 g, 1.1 equiv) in 50 mL acetonitrile was added tert-butyl 2-bromoacetate (3.92 mL, 1.1 equiv) dropwise at RT. The resulting mixture was then heated to reflux for 18 h. After cooling to RT, the mixture was diluted with DCM (100 mL), and then filtered through a pad of Celite; the filtrate was concentrated under reduced pressure. The remaining residue was purified by flash column chromatography over silica gel eluted with DCM/EtOAc to give 3A.

Compound 4A: tert-Butyl 2-(3-acetyl-5-hydroxy-1H-indol-1-yl) acetate.

To tert-Butyl 2-(3-acetyl-5-(benzyloxy)-1H-indol-1-yl) acetate (6 g) in THF (80 mL) was added Pd/C (0.05 equiv). The reaction mixture was stirred at RT for 5 h under an atmosphere of $H_2$. The reaction mixture was filtered through a pad of Celite and washed with DCM and MeOH. The filtrate was concentrated under reduced pressure and the remaining residue was purified by flash column chromatography over silica gel eluted with DCM/EtOAc to give 4A.

Compound 5A: 2-(3-Acetyl-5-hydroxy-1H-indol-1-yl) acetic acid.

106 tert-Butyl 2-(3-acetyl-5-hydroxy-1H-indol-1-yl)acetate (814 mg, 2.8 mmol) was taken in 4 N HCl in dioxane (10 mL) and the resulting reaction mixture was stirred at rt for 48 h. The solvent was removed under reduced pressure and the remaining material was used directly in the next synthetic step.

Scheme 2

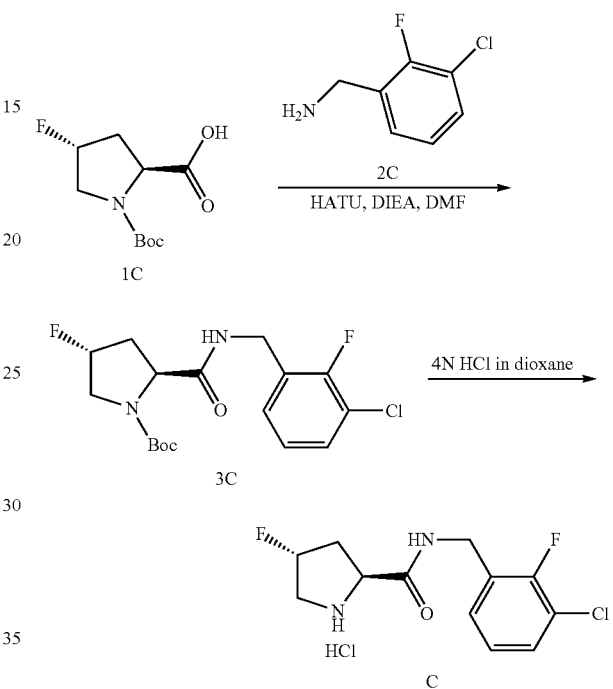

Compound 3C: (2S,4R)-tert-Butyl 2-((3-chloro-2-fluorobenzyl)carbamoyl)-4-fluoropyrrolidine-1-carboxylate.

(2S,4R)-1-(tert-Butoxycarbonyl)-4-fluoropyrrolidine-2-carboxylic acid 1C (2.33 g, 10 mmol) was dissolved in DMF (50 mL) and DIEA (8.6 mL, 5 equiv) was added, followed by the addition of (3-chloro-2-fluorophenyl) methanamine 2C (3.18 g 20 mmol) at 5° C. HATU (8 g, 2.1 equiv) was then added slowly at the same temperature. The reaction mixture was stirred for 18 h at RT, then the reaction mixture was diluted with 1 M citric acid solution (200 mL+20 g solid NaCl) and extracted with DCM (2×150 mL). The separated organic layer was washed successively with aq $NaHCO_3$ (100 mL), water (100 mL), and brine (100 mL), then dried over $Na_2SO_4$ and concentrated under reduced pressure. The remaining residue was purified by column chromatography over silica gel eluted with DCM/EtOAc to give 3C.

Compound C: (2S,4R)-N-(3-Chloro-2-Fluorobenzyl)-4-Fluoropyrrolidine-2-Carboxamide Hydrochloride.

(2S,4R)-tert-Butyl 2-((3-chloro-2-fluorobenzyl)carbamoyl)-4-fluoropyrrolidine-1-carboxylate (3C, 500 mg,) was taken in 4 N HCl in dioxane (20 mL) and the resulting reaction mixture was stirred at RT for 3 h. The solvent was removed under reduced pressure and the residue C was used directly in the next reaction.

Scheme 3

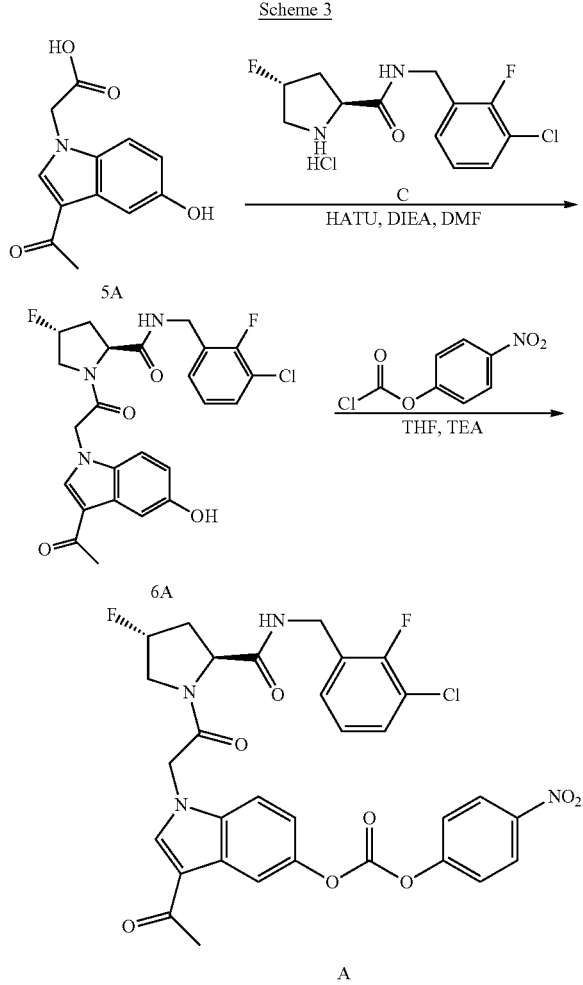

Compound 6A: (2S,4R)-1-(2-(3-acetyl-5-hydroxy-1H-indol-1-yl)acetyl)-N-(3-chloro-2-fluorobenzyl)-4-fluoropyrrolidine-2-carboxamide.

Compound 5A (2.8 mmol) from the previous reaction was dissolved in DMF (20 mL) and DIEA (2.076 mL, 5 equiv) was added, which was followed by the addition of (2S,4R)-N-(3-chloro-2-fluorobenzyl)-4-fluoropyrrolidine-2-carboxamide hydrochloride C (788 mg, 2.54 m.mol) at 5° C. HATU (2.026 g, 2.1 equiv) was then added slowly at the same temperature. The reaction mixture was then stirred for 18 h at rt, and the reaction mixture was diluted with 1 M citric acid solution and extracted with DCM. The separated organic layer was then washed successively with aq $NaHCO_3$, water, and brine, then dried over $Na_2SO_4$ and concentrated under reduced pressure. The remaining residue was purified by flash column chromatography over silica gel eluted with DCM/EtOAc to give 6A.

Compound A: 3-Acetyl-1-(2-((2S,4R)-2-((3-chloro-2-fluorobenzyl)carbamoyl)-4-fluoropyrrolidin-1-yl)-2-oxoethyl)-1H-indol-5-yl (4-nitrophenyl) carbonate.

Compound 6A (220 mg, 1 equiv) from the previous reaction was dissolved in THF (20 mL) and triethylamine (100 µL, 1.7 equiv) was added, which was followed by the addition of 4-nitrophenyl carbonochloridate (136 mg, 1.5 equiv) at 0° C. The reaction mixture was stirred for 18 h at RT, then diluted with water (5 mL) and extracted with ethyl acetate (50 mL). The separated organic layer was dried over $Na_2SO_4$ and concentrated under reduced pressure. The remaining residue was purified by flash column chromatography over silica gel eluted with DCM/EtOAc to give A.

Scheme 4

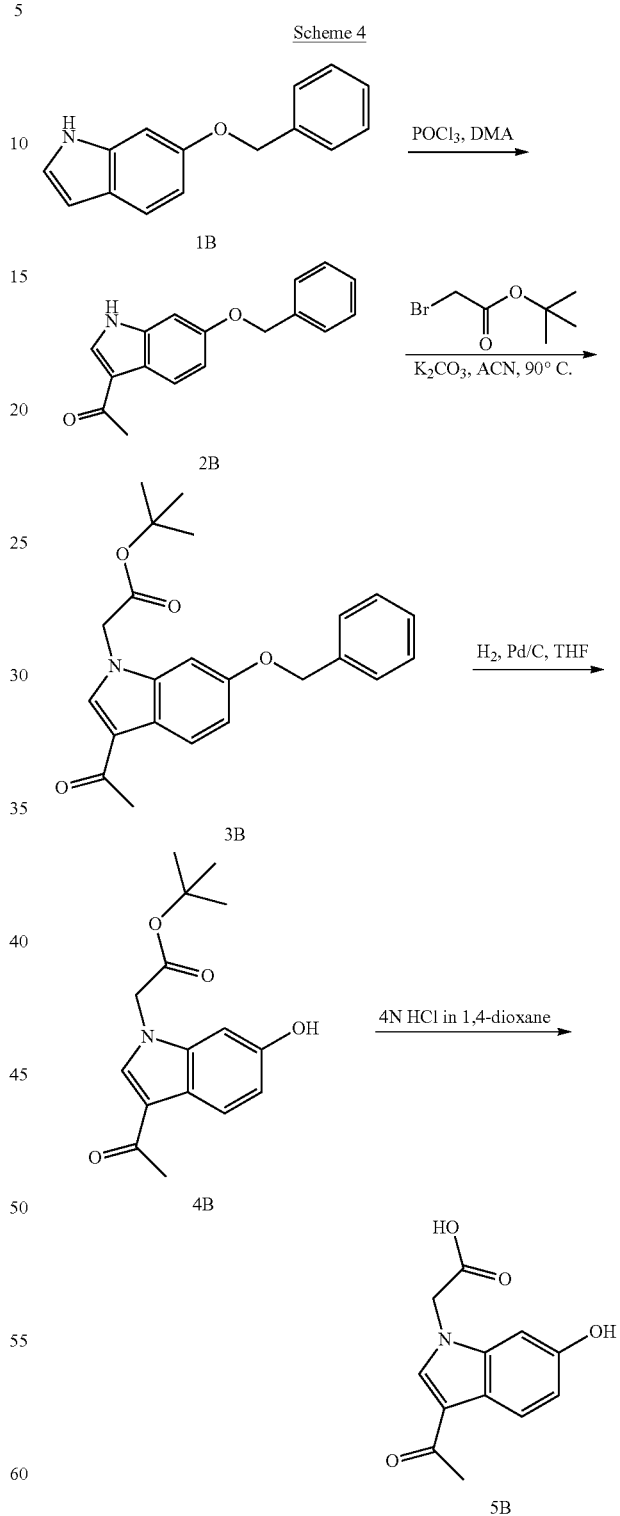

Compound 2B: 1-(6-(benzyloxy)-1H-indol-3-yl) ethanone.

Phosphoryl chloride (103 mL, 10 equiv) was added to ice-cold dimethylacetamide (311 mL, 30 equiv) with stirring and cooling in ice. 6-Benzyloxy indole (25 g, 1 equiv) was added and the reaction mixture was stirred at RT for 12 h, then poured over ice and basified with a 4 N aq sodium hydroxide solution until a precipitate formed. The solid was collected by filtration, washed with water, and dried. The solid was then slurried with methanol, collected by filtration, and dried to give 2B.

Compound 3B: tert-Butyl 2-(3-acetyl-6-(benzyloxy)-1H-indol-1-yl) acetate.

To a mixture of 1-(6-(benzyloxy)-1H-indol-3-yl)ethanone (25 g, 1 equiv) and potassium carbonate (11.6 g, 1.1 equiv) in acetonitrile (384 mL) was added tert-butyl bromoacetate (12.4 mL, 1.1 equiv) dropwise at RT. The resulting mixture was heated to reflux for 12 h, allowed to cool to RT, poured into water, and extracted with EtOAc. The combined organic extracts were concentrated under reduced pressure. The resulting solid was slurried with MTBE, collected by filtration, and dried to give 3B.

Compound 4B: tert-Butyl 2-(3-acetyl-6-hydroxy-1H-indol-1-yl) acetate.

A mixture of tert-butyl 2-(3-acetyl-6-(benzyloxy)-1H-indol-1-yl)acetate (22 g, 1 equiv), DCM/MeOH (600 mL), and Pd/C (2.2 g, 10%) was stirred at RT for 12 h under an atmosphere of $H_2$ (3.5 kg/cm$^2$). The reaction mixture was filtered through a pad of Celite and washed with DCM and MeOH. The filtrate was evaporated under reduce pressure, and the remaining crude product was slurried with DCM, collected by filtration, and dried to give 4B.

Compound 5B: 2-(3-Acetyl-6-hydroxy-1H-indol-1-yl) acetic acid.

tert-Butyl 2-(3-acetyl-6-hydroxy-1H-indol-1-yl)acetate (814 mg, 2.8 mmol) was taken in 4 N HCl in dioxane (10 mL) and the resulting reaction mixture was stirred at RT for 48 h. The solvent was removed under reduced pressure and the remaining material was used directly in the next synthetic step.

Scheme 5

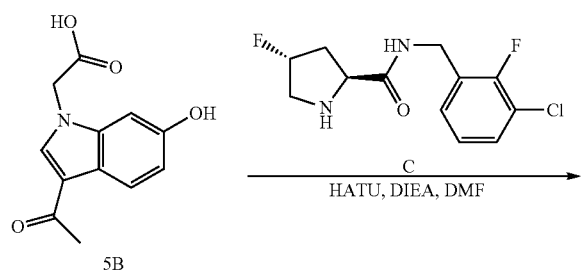

Compound 6B: (2S,4R)-1-(2-(3-Acetyl-6-hydroxy-1H-indol-1-yl)acetyl)-N-(3-chloro-2-fluorobenzyl)-4-fluoropyrrolidine-2-carboxamide.

(2S,4R)-N-(3-chloro-2-fluorobenzyl)-4-fluoropyrrolidine-2-carboxamide hydrochloride C (2.42 g) and 2-(3-acetyl-6-hydroxy-1H-indol-1-yl) acetic acid 5B (1.61 g) were dissolved in DMF (40 mL) and treated with HATU (3.56 g) in the presence of DIEA (4.08 mL) at RT overnight. After the solvent was removed under reduced pressure, the residue was purified by flash column chromatography on silica gel using 0-5% MeOH in DCM as eluent to give 6B.

Compound B: 3-Acetyl-1-(2-((2S,4R)-2-((3-chloro-2-fluorobenzyl)carbamoyl)-4-fluoropyrrolidin-1-yl)-2-oxoethyl)-1H-indol-6-yl (4-nitrophenyl) carbonate.

Compound 6B (450 mg, 1 equiv) from the previous reaction was dissolved in THF (20 mL) and triethylamine (200 1.7 equiv) was added, which was followed by the addition of 4-nitrophenyl carbonochloridate (277 mg, 1.5 equiv) at 0° C. The reaction mixture was then stirred for 18 h at RT, and then the reaction mixture was diluted with water (10 mL) and extracted with ethyl acetate (50 mL). The separated organic layer was dried over $Na_2SO_4$ and concentrated under reduced pressure. The remaining residue was purified by flash column chromatography over silica gel (eluted with DCM/EtOAc) to give B.

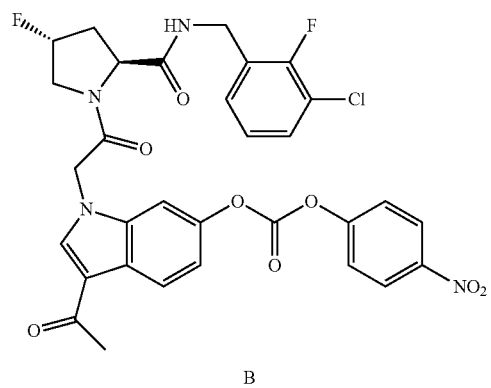

B

Scheme 6

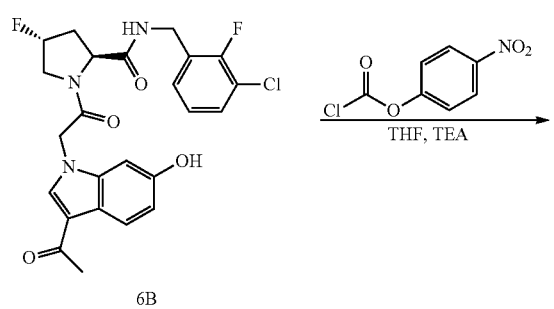

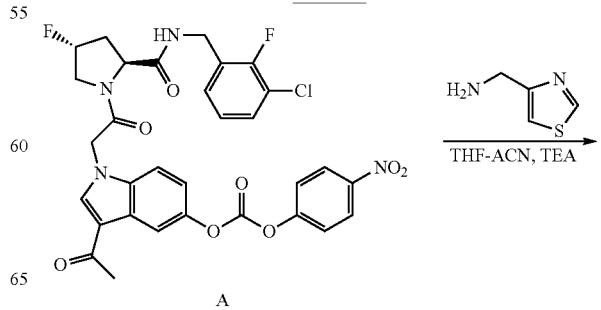

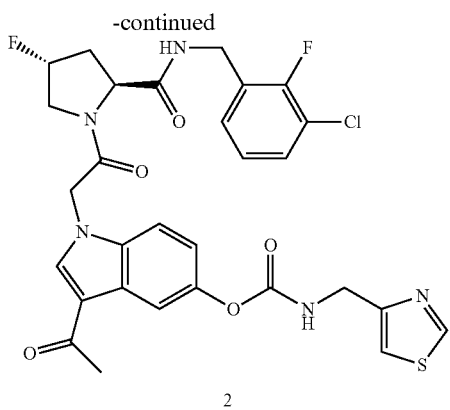

2

Compound 2: 3-Acetyl-1-(2-((2S,4R)-2-((3-chloro-2-fluorobenzyl)carbamoyl)-4-fluoropyrrolidin-1-yl)-2-oxoethyl)-1H-indol-5-yl (thiazol-4-ylmethyl)carbamate.

A mixture of 3-acetyl-1-(2-((2S,4R)-2-((3-chloro-2-fluorobenzyl)carbamoyl)-4-fluoropyrrolidin-1-yl)-2-oxoethyl)-1H-indol-5-yl (4-nitrophenyl) carbonate (A, 60 mg, 0.093 mmol), THF (5 mL), ACN (5 mL), and thiazol-4-ylmethanamine (16.8 mg, 1.2 equiv) was treated with triethylamine (32 μL, 2.5 equiv) at 0° C. The reaction mixture was stirred for 24 h at RT and concentrated under reduced pressure. The remaining residue was purified by flash column chromatography over silica gel (eluted with DCM/MeOH) to give 2. $^1$H NMR (400 MHz, DMSO-$d_6$, 300 K): (major rotamer) δ 2.01-2.18 (m, 1H), 2.42 (s, 3H), 2.48-2.56 (m, 1H), 3.84-3.98 (m, 1H), 4.07-4.19 (m, 1H), 4.24-4.50 (m, 5H), 5.18 (d, J=12 Hz, 1H), 5.4 (d, J=16 Hz, 1H), 5.44-5.58 (m, 1H), 6.98 (t, J=8, 2H), 7.14-7.24 (m, 1H), 7.38-7.43 (m, 1H), 7.54 (s, 1H), 7.86-7.87 (m, 1H), 8.28 (s, 2H), 8.59-8.62 (m, 1H), 9.09-9.10 (m, 1H), $^{19}$F NMR (376 MHz, DMSO-$d_6$, 300 K): (major rotamer) δ -176.10,-121.85. LC (method A): $t_R$=1.64 min. LC/MS (EI) m/z: calcd for $C_{29}H_{26}ClF_2N_5O_5S$, 629; found, [M+H]$^+$630.

Scheme 7

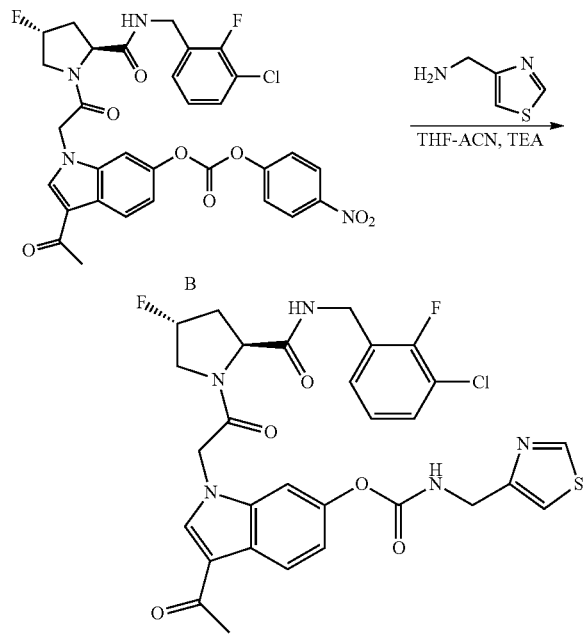

3

Compound 3: 3-Acetyl-1-(2-((2S,4R)-2-((3-chloro-2-fluorobenzyl)carbamoyl)-4-fluoropyrrolidin-1-yl)-2-oxoethyl)-1H-indol-6-yl (thiazol-4-ylmethyl)carbamate.

A mixture of 3-acetyl-1-(2-((2S,4R)-2-((3-chloro-2-fluorobenzyl)carbamoyl)-4-fluoropyrrolidin-1-yl)-2-oxoethyl)-1H-indol-6-yl (4-nitrophenyl) carbonate (B, 60 mg, 0.093mmol), THF (5 mL), ACN (5 mL), and thiazol-4-ylmethanamine (16.8 mg, 1.2 equiv) was treated with triethylamine (32 μL, 2.5 equiv) at 0° C. The reaction mixture was stirred for 24 h at RT, and then concentrated under reduced pressure. The remaining residue was purified by flash column chromatography over silica gel, eluted with DCM/CH$_3$OH to give 3. $^1$H NMR (400 MHz, DMSO-$d_6$, 300 K): (major rotamer) δ 2.01-2.18 (m, 1H), 2.43 (s, 3H), 2.45-2.56 (m, 1H), 3.84-3.86 (m, 1H), 4.10-4.19 (m, 1H), 4.24-4.48 (m, 5H), 5.16 (d, J=16 Hz, 1H), 5.375 (d, J=20 Hz, 1H), 5.44-5.57 (m, 1H), 6.98-7.01 (m, 2H), 7.23-7.26 (m, 1H), 7.34-7.49 (m, 3H), 8.13-8.17 (m, 1H), 8.22 (s, 1H), 8.27-8.31 (m, 1H), 8.58-8.61 (m, 1H), 9.07 (d, J=4 Hz, 1H), $^{19}$F NMR (376 MHz, DMSO-$d_6$, 300 K): (major rotamer) δ -176.05, -121.77. LC (method A): $t_R$=1.68 min. LC/MS (EI) m/z: calcd for $C_{29}H_{26}ClF_2N_5O_5S$, 629; found, [M+H]$^+$ 630.

Scheme 8

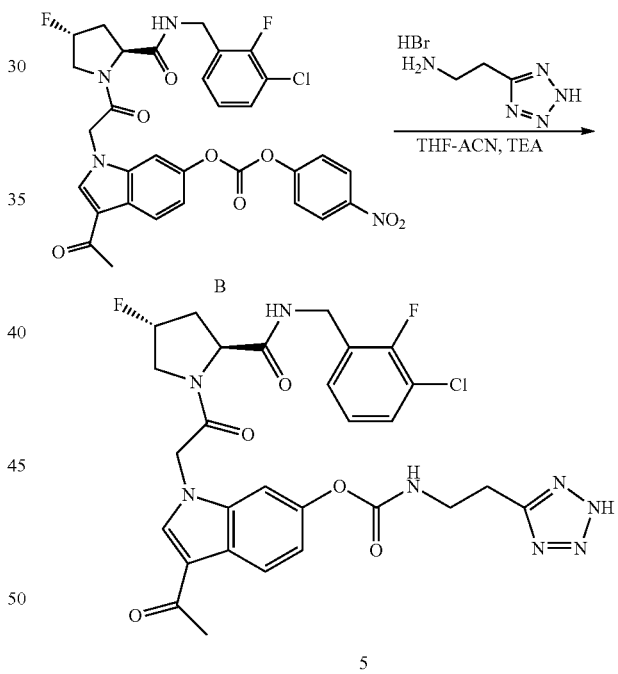

5

Compound 5: 3-Acetyl-1-(2-((2S,4R)-2-((3-chloro-2-fluorobenzyl)carbamoyl)-4-fluoropyrrolidin-1-yl)-2-oxoethyl)-1H-indol-6-yl (2-(2H-tetrazol-5-yl)ethyl)carbamate.

A mixture of 3-acetyl-1-(2-((2S,4R)-2-((3-chloro-2-fluorobenzyl)carbamoyl)-4-fluoropyrrolidin-1-yl)-2-oxoethyl)-1H-indol-6-yl (4-nitrophenyl) carbonate (B, 60 mg, 0.093 mmol), THF (5 mL), ACN (5 mL), and 2-(2H-tetrazol-5-yl)ethanamine hydrobromide (22 mg, 1.2 equiv) was treated with triethylamine (38 μL, 3 equiv) at 0° C. The reaction mixture was then stirred for 24 h at RT, and concentrated under reduced pressure. The remaining residue was purified by flash column chromatography over silica gel (eluted with DCM/MeOH) to give 5. $^1$H NMR (400 MHz, DMSO-$d_6$, 300 K): (major rotamer) δ 2.00-2.17 (m, 1H), 2.42 (s, 3H), 2.47-2.56 (m, 1H),3.07-3.11(m, 2H), 3.43-3.48 (m, 2H) 3.83-3.87 (m, 1H), 4.10-4.19 (m, 1H), 4.25-4.48 (m, 3H), 5.16 (d, J=16 Hz, 1H), 5.37 (d, J=16 Hz, 1H), 5.44-5.57 (m, 1H), 6.94-7.07 (m, 2H), 7.24 (t, J=8, 1H), 7.31 (d, J=4 Hz, 1H), 7.43 (t, J=8 Hz, 1H), 7.91-7.85 (m, 1H), 8.11-8.14 (m, 1H), 8.22 (s, 1H), 8.59-8.62 (m, 1H), $^{19}$F NMR (376 MHz, DMSO-$d_6$, 300 K): (major rotamer) δ −176.06, −121.77. LC (method A): $t_R$=1.45 min. LC/MS (EI) m/z: calcd for $C_{28}H_{27}ClF_2N_8O_5$, 628; found, [M+H]$^+$629.

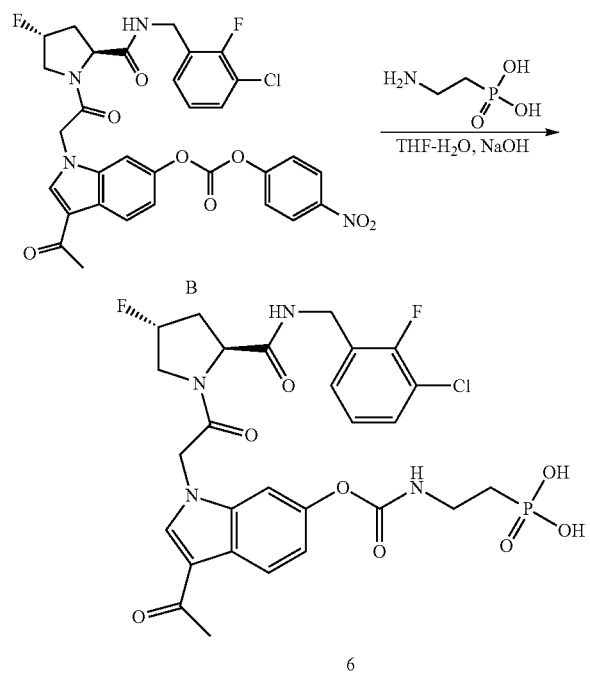

Scheme 9

Compound 6: (2-(((((3-Acetyl-1-(2-((2S,4R)-2-((3-chloro-2-fluorobenzyl)carbamoyl)-4-fluoropyrrolidin-1-yl)-2-oxoethyl)-1H-indol-6-yl)oxy)carbonyl)amino)ethyl)phosphonic acid.

A mixture of 3-acetyl-1-(2-((2S,4R)-2-((3-chloro-2-fluorobenzyl)carbamoyl)-4-fluoropyrrolidin-1-yl)-2-oxoethyl)-1H-indol-6-yl (4-nitrophenyl) carbonate (B, 60 mg, 0.093 mmol), THF (3 mL), water (3 mL), and (2-aminoethyl) phosphoric acid (24 mg, 2 equiv) was treated with 1 N NaOH (372 µL, 4 equiv) at 0° C. The reaction mixture was stirred for 48 h at RT, volatiles were removed under reduced pressure and the residue was purified by preparative HPLC to give title compound 6. $^1$H NMR (400 MHz, DMSO-$d_6$, 300 K): (major rotamer) δ 1.76-1.86 (m, 2H), 2.00-2.17 (m, 1H), 2.42 (s, 3H), 2.47-2.55 (m, 1H), 3.23-3.30 (m, 2H), 3.84-3.96 (m, 1H), 4.10-4.19 (m, 1H), 4.25-4.49 (m, 3H), 5.15 (d, J=20 Hz, 1H), 5.37 (d, J=16 Hz, 1H), 5.44-5.57 (m, 1H), 6.96-7.07 (m, 2H), 7.26 (t, J=8, 1H), 7.30-7.31 (m, 1H), 7.43 (t, J=8 Hz, 1H), 7.66-7.70 (m, 1H), 8.12-8.14 (m, 1H), 8.22 (s, 1H), 8.58-8.61 (m, 1H), $^{19}$F NMR (376 MHz, DMSO-$d_6$, 300 K): (major rotamer) δ −176.05, −121.24. LC (method A): $t_R$=1.16 min. LC/MS (EI) m/z: calcd for $C_{27}H_{28}ClF_2N_4O_8P$, 640; found, [M+H]$^+$641.

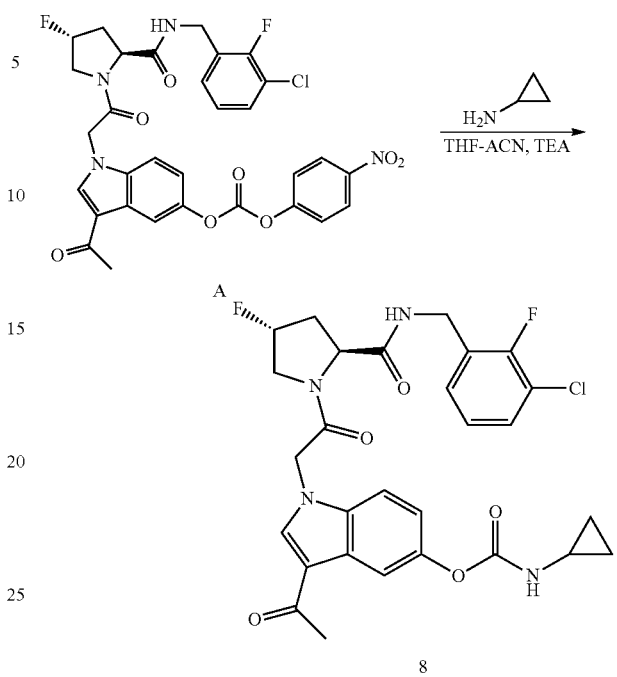

Scheme 10

Compound 8: 3-Acetyl-1-(2-((2S,4R)-2-((3-chloro-2-fluorobenzyl)carbamoyl)-4-fluoropyrrolidin-1-yl)-2-oxoethyl)-1H-indol-5-yl cyclopropylcarbamate.

A mixture of 3-acetyl-1-(2-((2S,4R)-2-((3-chloro-2-fluorobenzyl)carbamoyl)-4-fluoropyrrolidin-1-yl)-2-oxoethyl)-1H-indol-5-yl (4-nitrophenyl) carbonate (A, 60 mg, 0.093 mmol), THF (5 mL), ACN (5 mL), and cyclopropanamine (12.86 µL, 2 equiv) was treated with triethylamine (38 µL, 3 equiv) at 0° C. The reaction mixture was stirred for 24 h at RT, and then concentrated under reduced pressure. The remaining residue was purified by flash column chromatography over silica gel (eluted with DCM/MeOH) to give 8. $^1$H NMR (400 MHz, DMSO-$d_6$, 300 K): (major rotamer) δ 0.53 (s, br, 2H), 0.65 (d, J=5.6 Hz, 2H) 2.04-2.18 (m, 1H), 2.42 (s, 3H), 2.54-2.58 (m, 1H), 3.90 (ddd, J=22, 9.6, 3.2 Hz, 1H), 4.14 (dd, J=8.8, 12.4 Hz, 1H), 4.32 (dd, J=22.4, 6.0 Hz, 1H), 4.40-4.49 (m, 2H), 5.18 (d, J=17.2 Hz, 1H), 5.39 (d, J=17.2 Hz, 1H), 5.51 (d, J=52.8 Hz, 1H), 6.92-7.01 (m, 2H), 7.16-7.24 (m, 1H), 7.40-7.45 (m, 2H), 7.82-7.87 (m, 2H), 8.22 (s, 1H), 8.60 (t, J=5.6 Hz, 1H), $^{19}$F NMR (376 MHz, DMSO-$d_6$, 300 K): −176.1, −121.25, LC (method 1): $t_R$=1.73 min. LC/MS (APCI) m/z: calcd for $C_{28}H_{27}ClF_2N_4O_5$, 572; found, [M+H]$^+$573.

Scheme 11

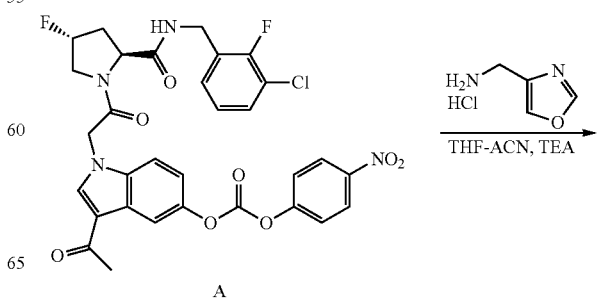

115
-continued

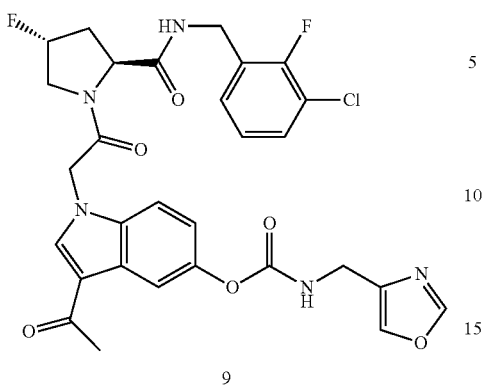

9

Compound 9: 3-Acetyl-1-(2-((2S,4R)-2-((3-chloro-2-fluorobenzyl)carbamoyl)-4- fluoropyrrolidin-1-yl)-2-oxoethyl)-1H-indol-5-yl (oxazol-4-ylmethyl)carbamate.

A mixture of 3-acetyl-1-(2-((2S,4R)-2-((3-chloro-2-fluorobenzyl)carbamoyl)-4- fluoropyrrolidin-1-yl)-2-oxoethyl)-1H-indol-5-yl (4-nitrophenyl) carbonate (A, 60 mg, 0.093 mmol), THF (5 mL), ACN (5 mL), and oxazol-4-ylmethanamine hydrochloride (15 mg, 1.2 equiv) was treated with triethylamine (38 µL, 3 equiv) at 0° C. The reaction mixture was stirred for 24 h at RT, and then reaction mixture was concentrated under reduced pressure. The remaining residue was purified by flash column chromatography over silica gel (eluted with DCM/MeOH) to give 9. $^1$H NMR (400 MHz, DMSO-$d_6$, 300 K): (major rotamer) δ 2.01-2.18 (m, 1H), 2.42 (s, 3H), 2.46-2.56 (m, 1H), 3.85-3.97 (m, 1H), 4.10-4.50 (m, 6H), 5.18 (d, J=16 Hz, 1H), 5.395 (d, J=20 Hz, 1H), 5.44-5.57 (m, 1H), 6.94-7.00 (m, 2H), 7.16-7.24 (m, 1H), 7.38-7.43 (m, 2H), 7.81 (s, 1H), 8.01 (s, 1H), 8.14-8.17 (m, 1H), 8.27 (s, 1H), 8.35 (s, 1H), 8.60 (t, J=4 Hz, 1H), $^{19}$F NMR (376 MHz, DMSO-$d_6$, 300 K): (major rotamer) δ −176.10, −121.85. LC (method A): $t_R$=1.55 min. LC/MS (EI) m/z: calcd for $C_{29}H_{26}ClF_2N_5O_6$, 613; found, [M+H]$^+$ 614.

116
-continued

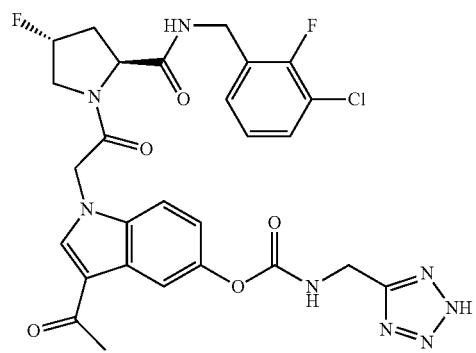

10

Compound 10: 3-Acetyl-1-(2-((2S,4R)-2-((3-chloro-2-fluorobenzyl)carbamoyl)-4-fluoropyrrolidin-1-yl)-2-oxoethyl)-1H-indol-5-yl ((2H-tetrazol-5-yl)methyl)carbamate (10).

A mixture of 3-acetyl-1-(2-((2S,4R)-2-((3-chloro-2-fluorobenzyl)carbamoyl)-4-fluoropyrrolidin-1-yl)-2-oxoethyl)-1H-indol-5-yl (4-nitrophenyl) carbonate (A, 60 mg, 0.093 mmol), THF (5 mL), ACN (5 mL), and (2H-tetrazol-5-yl)methanamine (12 mg, 1.2 equiv) was treated with triethylamine (38 µL, 3 equiv) at 0° C. The reaction mixture was stirred for 24 h at RT, and then concentrated under reduced pressure. The remaining residue was purified by flash column chromatography over silica gel (eluted with DCM/MeOH) to give 10. $^1$H NMR (400 MHz, DMSO-$d_6$, 300 K): (major rotamer) δ 2.02-2.18 (m, 1H), 2.42 (s, 3H), 2.46-2.56 (m, 1H), 3.85-3.96 (m, 1H), 4.10-4.19 (m, 1H), 4.24-4.29 (m, 1H), 4.35-4.50 (m, 2H), 4.63 (d, J=8, 2H), 5.19 (d, J=20 Hz, 1H), 5.40 (d, J=20 Hz, 1H), 5.42-5.57 (m, 1H), 6.96-7.00 (m, 2H), 7.19-7.24 (m, 1H), 7.38-7.45 (m, 2H), 7.91 (s, 1H), 8.28 (s, 1H), 8.42-8.45 (m, 1H), 8.58-8.61 (m, 1H), $^{19}$F NMR (376 MHz, DMSO-$d_6$, 300 K): (major rotamer) δ −176.10, −121.82. LC (method A): $t_R$=1.37 min. LC/MS (EI) m/z: calcd for $C_{27}H_{25}ClF_2N_8O_5$, 614; found, [M+H]$^+$ 615.

Scheme 13

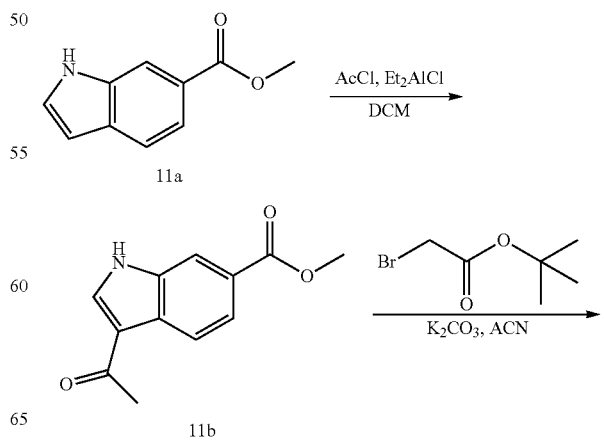

Scheme 12

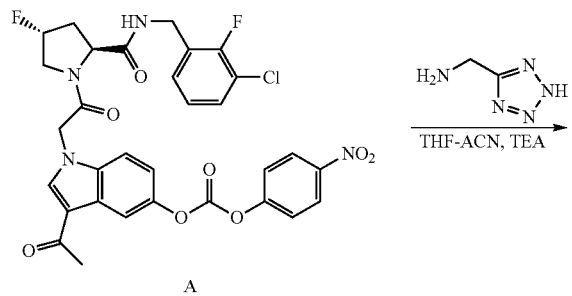

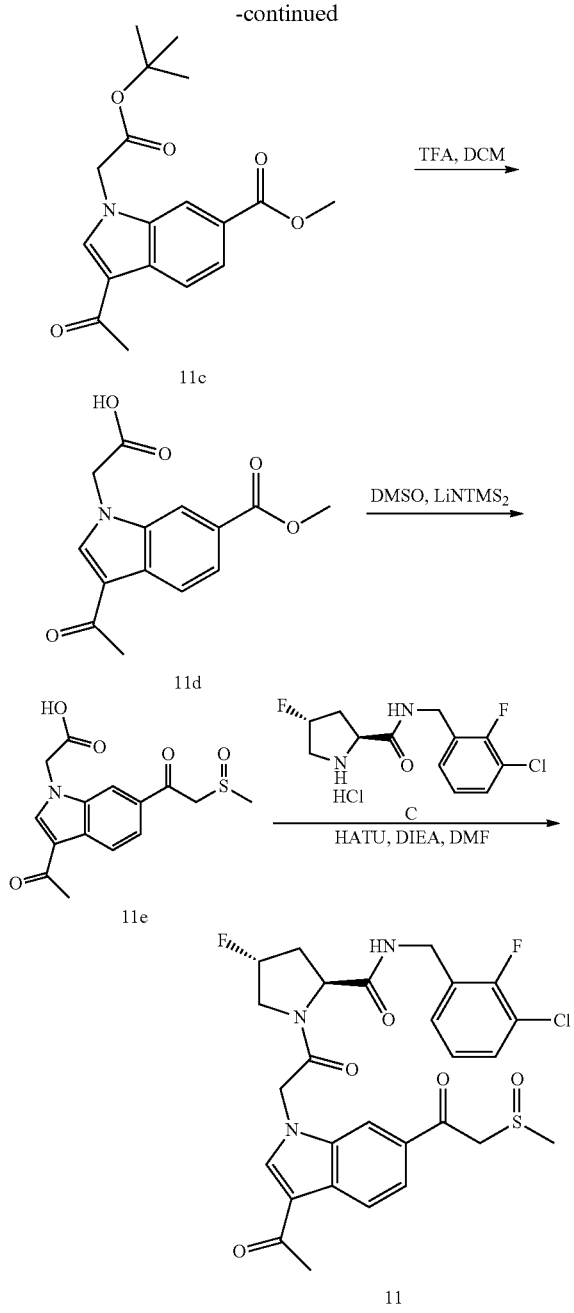

Compound 11b: Methyl 3-acetyl-1H-indole-6-carboxylate.

Into a solution of methyl 1H-indole-6-carboxylate (1.06 g) in DCM (20 mL), Et₂AlCl (1.0 M in hexane, 9.09 mL) was added slowly at 0° C. under argon and stirring was continued for 30 min. A solution of acetyl chloride (0.653 mL) in DCM (20 mL) was added, and the mixture was stirred at RT overnight. The dark reaction mixture was poured into a 5% aq citric acid solution (100 mL) at 0° C. and stirred. The precipitate was collected by filtration and dried to give 11b.

Compound 11c: Methyl 3-acetyl-1-(2-(tert-butoxy)-2-oxoethyl)-1H-indole-6-carboxylate.

A mixture of 3-acetyl-1H-indole-6-carboxylate (0.7 g) and tert-butyl 2-bromoacetate (0.52 mL) was refluxed in acetonitrile (15 mL) in the presence of K₂CO₃ (0.49 g) overnight. After cooling to RT, the solid was removed by filtration and the filtrate was concentrated under reduced pressure. The remaining residue was dissolved in DCM (30 mL) and washed sequentially with 1 N HCl (5 mL), NaHCO₃ aq (10 mL), and brine. After dried over anhydrous Na₂SO₄, the solvent was removed under reduced pressure to give 11c.

Compound 11d: 2-(3-Acetyl-6-(methoxycarbonyl)-1H-indol-1-yl)acetic acid.

3-Acetyl-1-(2-(tert-butoxy)-2-oxoethyl)-1H-indole-6-carboxylate (205 mg) in DCM (3 mL) was treated with TFA (3 mL) at RT for 4 h. Volatiles were removed under reduced pressure to give 2-(3-acetyl-6-(methoxycarbonyl)-1H-indol-1-yl)acetic acid (11d).

Compound 11e: 2-(3-Acetyl-6-(2-(methylsulfinyl)acetyl)-1H-indol-1-yl)acetic acid.

Into a flask charged with anhydrous DMSO (5 mL), lithium bis(trimethylsilyl) amide (2.0 M in THF, 5 mL) was added at RT with stirring. The mixture was cooled to 0° C., and then 2-(3-acetyl-6-(methoxycarbonyl)-1H-indol-1-yl) acetic acid (11d) from above in DMSO (5 mL) was added. The reaction mixture was stirred gradually to RT over 2 h and then cooled to 0° C. An aq solution of citric acid (5%, 50 mL) was added to quench the reaction. NaCl was added to saturate the aq layer and the pH was adjusted to ~2. EtOAc containing 5% of 2,2,2-trifluoroethanol was used for extraction. The separated organic layer was dried over anhydrous Na₂SO₄, and the solvent was removed under reduced pressure. The residue was tritrated with MeOH and filtered to give 11e.

Compound 11: (2S,4R)-1-(2-(3-acetyl-6-(2-(methylsulfinyl)acetyl)-1H-indol-1-yl)acetyl)-N-(3-chloro-2-fluorobenzyl)-4-fluoropyrrolidine-2-carboxamide.

Into a mixture of 2-(3-acetyl-6-(2-(methylsulfinyl) acetyl)-1H-indol-1-yl)acetic acid (66 mg) and (2S,4R)-N-(3-chloro-2-fluorobenzyl)-4-fluoropyrrolidine-2-carboxamide hydrochloride (64 mg) in DMF (1 mL) was added HATU (0.117 g) followed by DIEA (0.174 mL). After stirred at RT for 2 h, water (10 mL) was added and the mixture was extracted with EtOAc (20 mL). The crude obtained after evaporation of the separated organic layer was purified by flash column chromatography over silica gel (eluted with DCM/MeOH) to give (2S,4R)-1-(2-(3-acetyl-6-(2-(methylsulfinyl)acetyl)-1H-indol-1-yl)acetyl)-N-(3-chloro-2-fluorobenzyl)-4-fluoropyrrolidine-2-carboxamide 11. $^1$H NMR (400 MHz, CDCl₃/CD₃OD, 300 K): (major rotamer) δ 2.15-2.37 (m, 1H), 2.60 (s, 3H), 2.75 (s, 3H), 3.95-4.15 (m, 1H), 4.50-4.70 (m, 3H), 5.10-5.25 (m, 2H), 5.45 (d, J=52.8 Hz, 1H), 6.70-6.80 (m, 1H), 7.14-7.2 (m, 2H), 7.84-8.18 (s, 2H), 8.40 (s, 1H), 8.39-8.42 (m, 2H). LC (method 1): $t_R$=1.35 min. LC/MS (EI) m/z: calcd for C₂₇H₂₆ClF₂N₃O₅S, 577; found, [M+H]⁺578.

Scheme 14

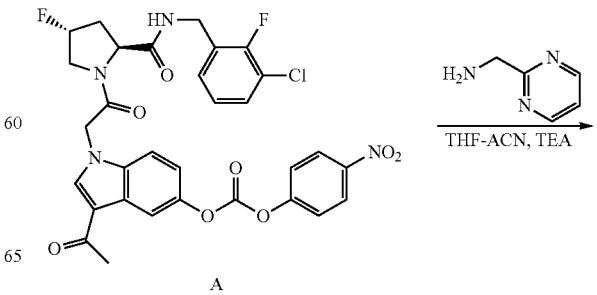

-continued

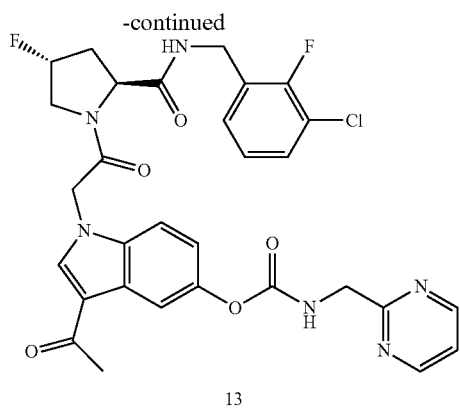

13

Compound 13: 3-Acetyl-1-(2-((2S,4R)-2-((3-chloro-2-fluorobenzyl)carbamoyl)-4-fluoropyrrolidin-1-yl)-2-oxoethyl)-1H-indol-5-yl(pyrimidin-2-ylmethyl)carbamate.

A mixture of 3-acetyl-1-(2-((2S,4R)-2-((3-chloro-2-fluorobenzyl)carbamoyl)-4-fluoropyrrolidin-1-yl)-2-oxoethyl)-1H-indol-5-yl (4-nitrophenyl) carbonate (A, 40 mg, 0.061 mmol), THF (3 mL), ACN (3 mL), and pyrimidin-2-ylmethanamine (9.97 mg, 1.5 equiv) was treated with triethylamine (26 µL, 3 equiv) at 0° C. The reaction mixture was stirred for 24 h at RT, and then concentrated under reduced pressure. The remaining residue was purified by flash column chromatography over silica gel (eluted with DCM/MeOH) to give 13. $^1$H NMR (400 MHz, DMSO-$d_6$, 300 K): (major rotamer) δ 2.01-2.18 (m, 1H), 2.42 (s, 3H), 2.45-2.56 (m, 1H), 3.84-3.96 (m, 1H), 4.10-4.19 (m, 1H), 4.23-4.51 (m, 5H), 5.18 (d, J=16 Hz, 1H), 5.38 (d, J=20 Hz, 1H), 5.44-5.57 (m, 1H), 6.97 (t, J=8, 2H), 7.18-7.24 (m, 1H), 7.38-7.45 (m, 3H), 7.88 (s, 1H), 8.18-8.22 (m, 1H), 8.27 (s, 1H), 8.58-8.61 (m, 1H), 8.83 (d, J=8, 2H), $^{19}$F NMR (376 MHz, DMSO-$d_6$, 300 K): (major rotamer) δ -176.10, -121.86. LC (method A): $t_R$=1.10 min. LC/MS (EI) m/z: calcd for $C_{30}H_{27}ClF_2N_6O_5$, 624; found, [M+H]$^+$625.

Compound 14: 3-Acetyl-1-(2-((2S,4R)-2-((3-chloro-2-fluorobenzyl)carbamoyl)-4-fluoropyrrolidin-1-yl)-2-oxoethyl)-1H-indol-5-yl (2-(2H-tetrazol-5-yl)ethyl)carbamate.

A mixture of 3-acetyl-1-(2-((2S,4R)-2-((3-chloro-2-fluorobenzyl)carbamoyl)-4-fluoropyrrolidin-1-yl)-2-oxoethyl)-1H-indol-5-yl (4-nitrophenyl) carbonate (A, 40 mg, 0.061 mmol), THF (3 mL), ACN (3 mL), and 2-(2H-tetrazol-5-yl)ethanamine hydrobromide (17.65 mg, 1.5 equiv) was treated with triethylamine (16.97 µL, 2 equiv) at 0° C. The reaction mixture was then stirred for 24 h at RT, and then the reaction mixture was concentrated under reduced pressure. The remaining residue was purified by flash column chromatography over silica gel (eluted with DCM/MeOH) to give 14. $^1$H NMR (400 MHz, DMSO-$d_6$, 300 K): (major rotamer) δ 2.00-2.17 (m, 1H), 2.42 (s, 3H), 2.45-2.56 (m, 1H), 3.12 (t, J=8, 2H), 3.45-3.50 (m, 2H) 3.84-3.97 (m, 1H), 4.10-4.18 (m, 1H), 4.23-4.29 (m, 1H), 4.35-4.49 (m, 2H), 5.18 (d, J=20 Hz, 1H), 5.39 (d, J=20 Hz, 1H), 5.44-5.57 (m, 1H), 6.91-6.94 (m, 1H), 6.99 (t, J=8, 1H), 7.20-7.24 (m, 1H), 7.39-7.43 (m, 2H), 7.82-7.88 (m, 2H), 8.27 (s, 1H), 8.58-8.61 (m, 1H), $^{19}$F NMR (376 MHz, DMSO-$d^6$, 300 K): (major rotamer) δ -176.11, -121.81. LC (method A): $t_R$=1.14 min. LC/MS (EI) m/z: calcd for $C_{28}H_{27}ClF_2N_8O_5$, 628; found, [M+H]$^+$629.

Scheme 16

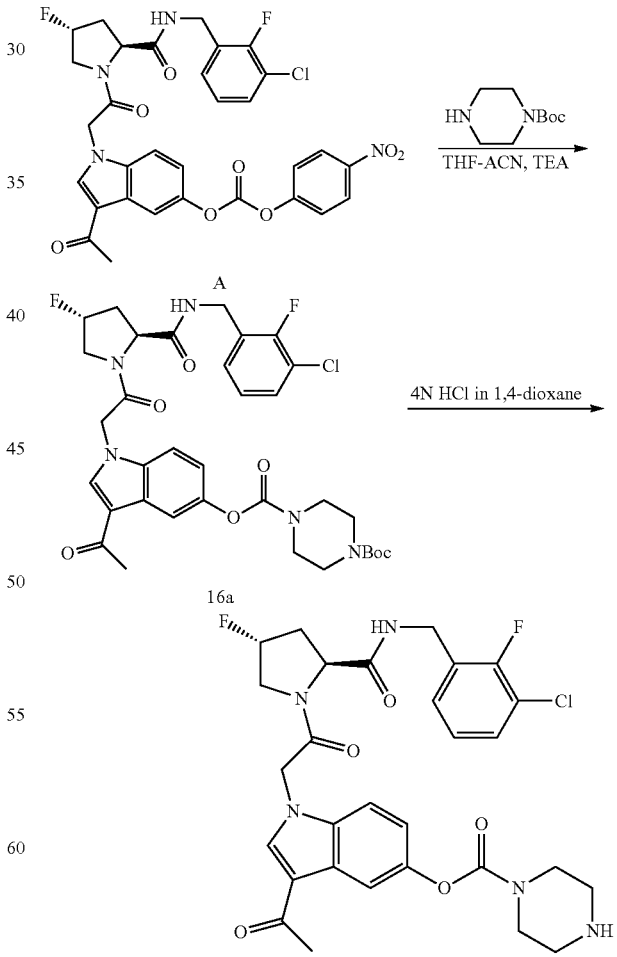

16a

16

Scheme 15

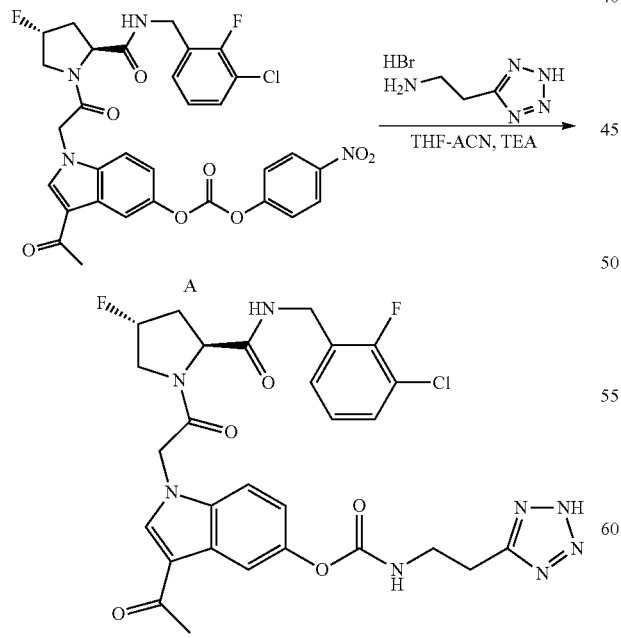

14

Compound 16a: 1-(3-Acetyl-1-(2-((2S,4R)-2-((3-chloro-2-fluorobenzyl)carbamoyl)-4-fluoropyrrolidin-1-yl)-2-oxoethyl)-1H-indol-5-yl) 4-tert-butyl piperazine-1,4-dicarboxylate.

A mixture of 3-acetyl-1-(2-((2S,4R)-2-((3-chloro-2-fluorobenzyl)carbamoyl)-4-fluoropyrrolidin-1-yl)-2-oxoethyl)-1H-indol-5-yl (4-nitrophenyl) carbonate (A, 20 mg, 0.03 mmol), THF (1.5 mL), ACN (1.5 mL), and tent-butyl piperazine-1-carboxylate (8.37 mg, 1.5 equiv) was treated with triethylamine (8.34 µL, 2 equiv) at 0° C. The reaction mixture was stirred for 24 h at RT, and then concentrated under reduced pressure. The remaining residue was purified by flash column chromatography over silica gel (eluted with DCM/MeOH) to give 16a.

Compound 16: 3-Acetyl-1-(2-((2S,4R)-2-((3-chloro-2-fluorobenzyl)carbamoyl)-4-fluoropyrrolidin-1-yl)-2-oxoethyl)-1H-indol-5-yl piperazine-1-carboxylate.

1-(3-Acetyl-1-(2-((2S,4R)-2-((3-chloro-2-fluorobenzyl)carbamoyl)-4-fluoropyrrolidin-1-yl)-2-oxoethyl)-1H-indol-5-yl) 4-tert-butyl piperazine-1,4-dicarboxylate (16a, 20 mg) from the previous reaction was dissolved in 4 N HCl in dioxane (2 mL) and the resulting reaction mixture was stirred at RT for 3 h. The solvent was then removed under reduced pressure to give 16. $^1$H NMR (400 MHz, DMSO-d$_6$, 300 K): (major rotamer) δ 2.02-2.18 (m, 1H), 2.43 (s, 3H), 2.46-2.52 (m, 1H), 2.19-2.26 (m, 4H), 3.68-3.99 (m, 5H), 4.10-4.19 (m, 1H), 4.23-4.29 (m, 1H), 4.35-4.50 (m, 2H), 5.21 (d, J=16 Hz, 1H), 5.40 (d, J=16 Hz, 1H), 5.45-5.58 (m, 1H), 6.97-7.01 (m, 2H), 7.23 (t, J=8 Hz, 1H), 7.40-7.47 (m, 2H), 7.915 (d, J=4 Hz, 1H), 8.30 (s, 1H), 9.01 (s, 2H), $^{19}$F NMR (376 MHz, DMSO-d$_6$, 300 K): (major rotamer) δ −176.08, −121.84. LC (method A): t$_R$=1.11 min. LC/MS (EI) m/z: calcd for $C_{29}H_{30}ClF_2N_5O_5$, 601; found, [M+H] 602.

EXAMPLE 8 non-Limiting Examples of Compounds of Formula I

Table 1 shows illustrative compounds of Formula I with characaterizing data. The assay of Example 9 was used to determine the IC$_{50}$'s of the compounds. Other standard factor D inhibition assays are also available. Three \*\*\*s are used to denote compounds with an IC$_{50}$ less than 1 micromolar; two \*\*s indicate compound with an IC$_{50}$ between 1 micromolar and 10 micromolar, and one \* denotes compounds with an IC$_{50}$ greater than 10 micromolar.

TABLE 1

| Cmp No. | Structure | Name | IC$_{50}$ | RT min (Method A or B) | MS (M + 1) |
|---|---|---|---|---|---|
| 1 | 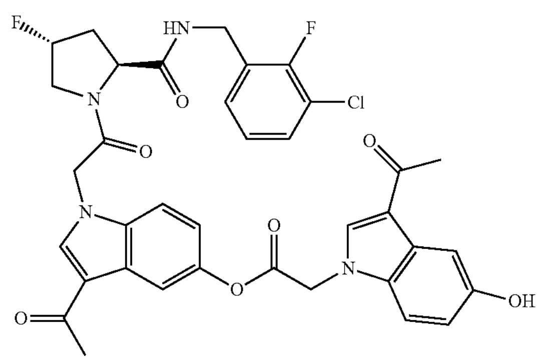 [SMILES: CC(=O)c1cn(CC(=O)Oc2ccc3c(c2)c(C(C)=O)cn3CC(=O)N2C[C@H](F)C[C@H]2C(=O)NCc2cccc(Cl)c2F)c2ccc(O)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-yl 2-(3-acetyl-5-hydroxy-1H-indol-1-yl)acetate | \*\*\* | 1.77 (A) | 705 |
| 2 | 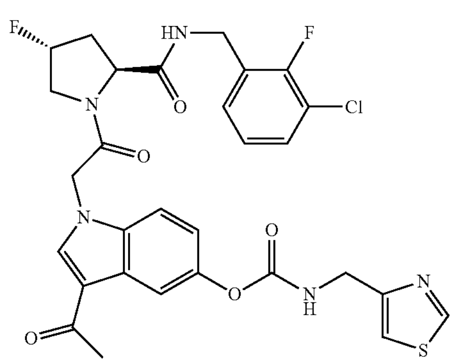 [SMILES: CC(=O)c1cn(CC(=O)N2C[C@H](F)C[C@H]2C(=O)NCc2cccc(Cl)c2F)c2ccc(OC(=O)NCc3cscn3)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-yl thiazol-4-ylmethylcarbamate | \*\*\* | 1.64 (A) | 630 |

TABLE 1-continued

| Cmp No. | Structure | Name | IC$_{50}$ | RT min (Method A or B) | MS (M + 1) |
|---|---|---|---|---|---|
| 3 | 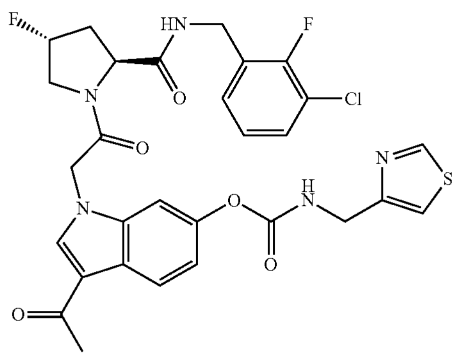 [SMILES: CC(=O)c1cn(CC(=O)N2C[C@H](F)C[C@H]2C(=O)NCc2cccc(Cl)c2F)c2cc(OC(=O)NCc3cscn3)ccc12] | 3-acetyl-1-(2-((2S,4R)-2-(3-chloro-2-fluorobenzylcarbamoyl)-4-fluoropyrrolidin-1-yl)-2-oxoethyl)-1H-indol-6-yl thiazol-4-ylmethylcarbamate | *** | 1.68 (A) | 630 |
| 4 | 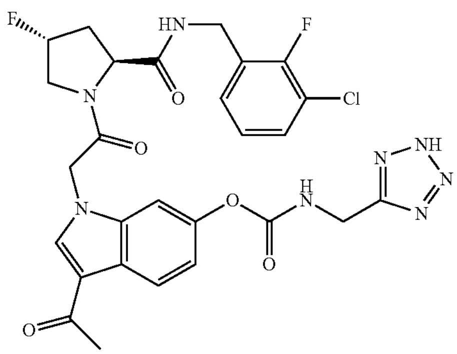 [SMILES: CC(=O)c1cn(CC(=O)N2C[C@H](F)C[C@H]2C(=O)NCc2cccc(Cl)c2F)c2cc(OC(=O)NCc3nn[nH]n3)ccc12] | 3-acetyl-1-(2-((2S,4R)-2-(3-chloro-2-fluorobenzylcarbamoyl)-4-fluoropyrrolidin-1-yl)-2-oxoethyl)-1H-indol-6-yl (2H-tetrazol-5-yl)methylcarbamate | *** | 1.42 (A) | 615 |
| 5 | 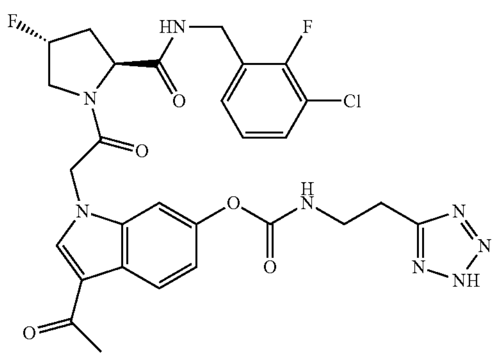 [SMILES: CC(=O)c1cn(CC(=O)N2C[C@H](F)C[C@H]2C(=O)NCc2cccc(Cl)c2F)c2cc(OC(=O)NCCc3nn[nH]n3)ccc12] | 3-acetyl-1-(2-((2S,4R)-2-(3-chloro-2-fluorobenzylcarbamoyl)-4-fluoropyrrolidin-1-yl)-2-oxoethyl)-1H-indol-6-yl 2-(2H-tetrazol-5-yl)ethylcarbamate | *** | 1.45 (A) | 629 |
| 6 | 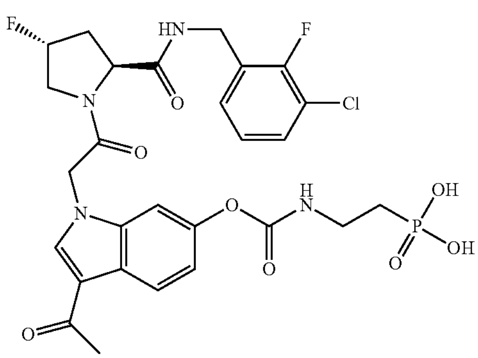 [SMILES: CC(=O)c1cn(CC(=O)N2C[C@H](F)C[C@H]2C(=O)NCc2cccc(Cl)c2F)c2cc(OC(=O)NCCP(=O)(O)O)ccc12] | 2-((3-acetyl-1-(2-((2S,4R)-2-(3-chloro-2-fluorobenzylcarbamoyl)-4-fluoropyrrolidin-1-yl)-2-oxoethyl)-1H-indol-6-yloxy)carbonylamino)ethylphosphonic acid | *** | 1.16 (A) | 641 |

TABLE 1-continued

| Cmp No. | Structure | Name | IC$_{50}$ | RT min (Method A or B) | MS (M + 1) |
|---|---|---|---|---|---|
| 7 | 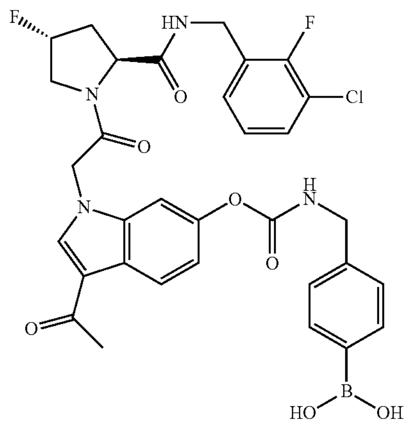 [SMILES: CC(=O)c1cn(CC(=O)N2C[C@H](F)C[C@H]2C(=O)NCc2cccc(Cl)c2F)c2cc(OC(=O)NCc3ccc(B(O)O)cc3)ccc12] | 4-(((3-acetyl-1-(2-((2S,4R)-2-(3-chloro-2-fluorobenzylcarbamoyl)-4-fluoropyrrolidin-1-yl)-2-oxoethyl)-1H-indol-6-yloxy)carbonylamino)methyl)phenylboronic acid | *** | 1.65 (A) | 667 |
| 8 | 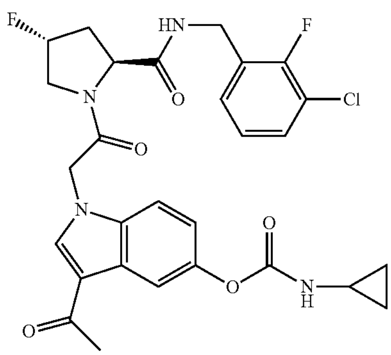 [SMILES: CC(=O)c1cn(CC(=O)N2C[C@H](F)C[C@H]2C(=O)NCc2cccc(Cl)c2F)c2ccc(OC(=O)NC3CC3)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-yl cyclopropylcarbamate | *** | 1.73 (A) | 573 |
| 9 | 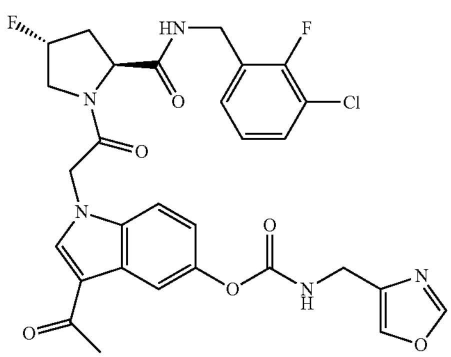 [SMILES: CC(=O)c1cn(CC(=O)N2C[C@H](F)C[C@H]2C(=O)NCc2cccc(Cl)c2F)c2ccc(OC(=O)NCc3cocn3)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-yl oxazol-4-ylmethylcarbamate | *** | 1.55 (A) | 614 |
| 10 | 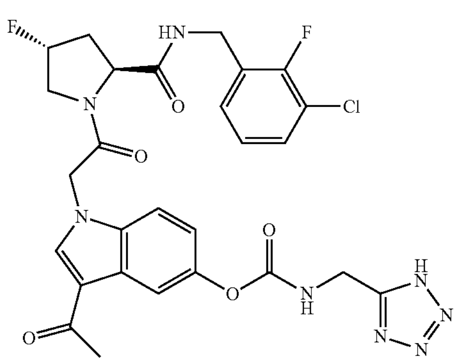 [SMILES: CC(=O)c1cn(CC(=O)N2C[C@H](F)C[C@H]2C(=O)NCc2cccc(Cl)c2F)c2ccc(OC(=O)NCc3nnn[nH]3)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-yl (1H-tetrazol-5-yl)methylcarbamate | *** | 1.37 (A) | 615 |

TABLE 1-continued

| Cmp No. | Structure | Name | IC$_{50}$ | RT min (Method A or B) | MS (M + 1) |
|---|---|---|---|---|---|
| 11 | 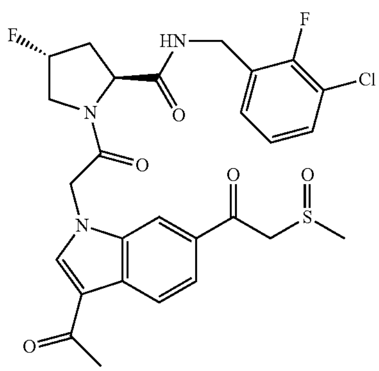 [SMILES: CC(=O)c1cn(CC(=O)N2C[C@H](F)C[C@H]2C(=O)NCc2cccc(Cl)c2F)c2cc(C(=O)CS(C)=O)ccc12] | (2S,4R)-1-(2-(3-acetyl-6-(2-(methylsulfinyl)acetyl)-1H-indol-1-yl)acetyl)-N-(3-chloro-2-fluorobenzyl)-4-fluoropyrrolidine-2-carboxamide | *** | 1.35 (A) | 578 |
| 12 | 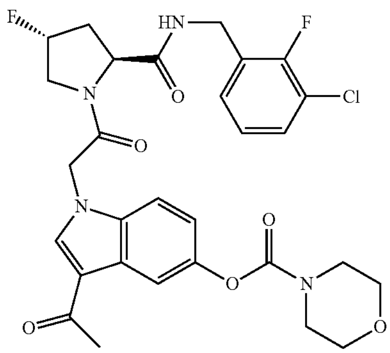 [SMILES: CC(=O)c1cn(CC(=O)N2C[C@H](F)C[C@H]2C(=O)NCc2cccc(Cl)c2F)c2ccc(OC(=O)N3CCOCC3)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-yl morpholine-4-carboxylate | *** | 1.39 (A) | 603 |
| 13 | 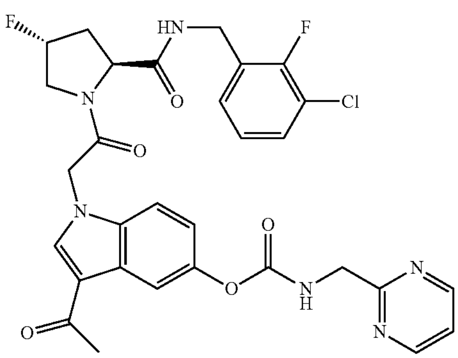 [SMILES: CC(=O)c1cn(CC(=O)N2C[C@H](F)C[C@H]2C(=O)NCc2cccc(Cl)c2F)c2ccc(OC(=O)NCc3ncccn3)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-yl pyrimidin-2-ylmethylcarbamate | *** | 1.10 (A) | 625 |
| 14 | 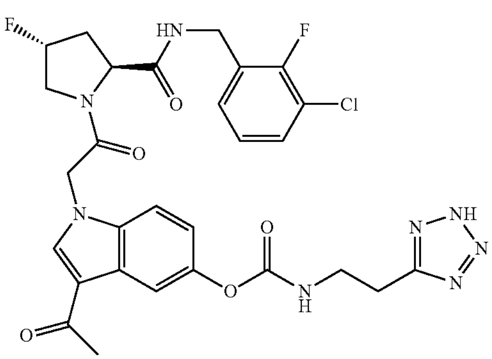 [SMILES: CC(=O)c1cn(CC(=O)N2C[C@H](F)C[C@H]2C(=O)NCc2cccc(Cl)c2F)c2ccc(OC(=O)NCCc3nn[nH]n3)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-yl 2-(2H-tetrazol-5-yl)ethylcarbamate | *** | 1.14 (A) | 629 |

TABLE 1-continued

| Cmp No. | Structure | Name | IC$_{50}$ | RT min (Method A or B) | MS (M + 1) |
|---|---|---|---|---|---|
| 15 | 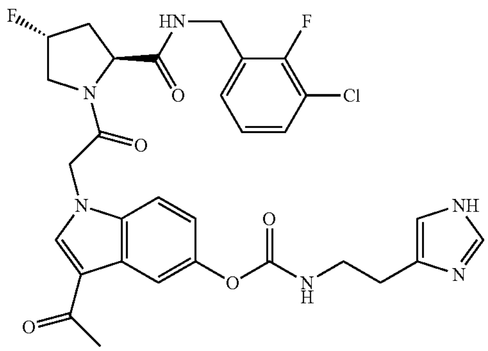 [SMILES: CC(=O)c1cn(CC(=O)N2C[C@H](F)C[C@H]2C(=O)NCc2cccc(Cl)c2F)c2ccc(OC(=O)NCCc3c[nH]cn3)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-yl 2-(1H-imidazol-4-yl)ethylcarbamate | *** | 0.95 (A) | 627 |
| 16 | 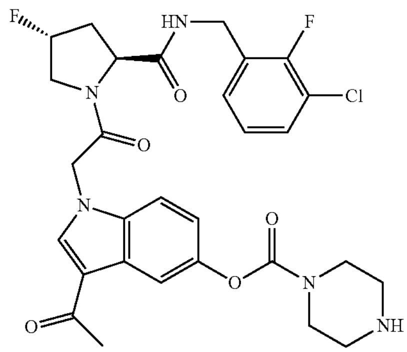 [SMILES: CC(=O)c1cn(CC(=O)N2C[C@H](F)C[C@H]2C(=O)NCc2cccc(Cl)c2F)c2ccc(OC(=O)N3CCNCC3)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-yl piperazine-1-carboxylate | *** | 1.11 (A) | 602 |

EXAMPLE 9

Human Factor D Assay

Human factor D (purified from human serum, Complement Technology, Inc.) at 80 nM final concentration is incubated with test compound at various concentrations for 5 minutes at room temperature in 50 mM Tris, 1M NaCl, pH 7.5. A synthetic substrate Z-L-Lys-SBzl and DTNB (Ellman's reagent) are added to final concentrations of 100 µM each. The increase in color is recorded at OD$_{405}$ nm in a microplate in kinetic mode over 30 minutes with 30 second time points in a spectrofluorimeter. IC$_{50}$ values are calculated by non-linear regression from the percentage of inhibition of complement factor D activity as a function of test compound concentration.

EXAMPLE 10

Hemolysis Assay

The hemolysis assay was previously described by G. Ruiz-Gomez, et al., J. Med. Chem. (2009) 52: 6042-6052. In the assay red blood cells (RBC), rabbit erythrocyctes (purchased from Complement Technologies), are washed using GVB Buffer (0.1% gelatin, 5 mM Veronal, 145 mM NaCl, 0.025% NaN$_3$, pH 7.3) plus 10 mM final Mg-EGTA. Cells are used at a concentration of 1×10$^8$ cells/mL. Prior to the hemolysis assay, the optimum concentration of Normal Human Serum (NHS) needed to achieve 100% lysis of rabbit erythrocytes is determined by titration. NHS (Complement Technologies) is incubated with inhibitor for 15 min at 37° C., rabbit erythrocytes in buffer were added and incubated for an additional 30 min at 37° C. Positive control (100% lysis) consists of serum and RBC and negative control (0% lysis) of Mg-EGTA buffer and RBC only. Samples are centrifuged at 2000 g for 5 min, and supernatants collected. Optical density of the supernatant is monitored at 405 nm using a UV/visible spectrophotometer. Percentage lysis in each sample is calculated relative to positive control (100% lysis).

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

What is claimed is:
1. A compound of Formula I

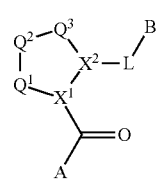

or a pharmaceutically acceptable salt thereof, wherein:
Q$^1$ is C(R$^1$R$^{1'}$);
Q$^2$ is C(R$^2$R$^{2'}$);
Q$^3$ is C(R$^3$R$^{3'}$);
X$^1$ is N and X$^2$ is CH;

$R^1$, $R^{1'}$, $R^2$, $R^{2'}$, $R^3$, and $R^{3'}$ are independently chosen from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkyl$NR^9R^{10}$, —C(O)$OR^9$, —OC(O)$R^9$, —$NR^9$C(O)$R^{10}$, —C(O)$NR^9R^{10}$, —OC(O)$NR^9R^{10}$, —$NR^9$C(O)$OR^{10}$, $C_1$-$C_2$haloalkyl, and $C_1$-$C_2$haloalkoxy, $R^9$ and $R^{10}$ are independently chosen at each occurrence from hydrogen, $C_1$-$C_6$alkyl, (C3-C7cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl);

or $R^1$ and $R^2$ form a 3- to 6-membered carbocyclic or aryl ring;

or $R^2$ and $R^3$ form a 3- to 6-membered carbocyclic ring;

or $R^1$ and $R^{1'}$, or $R^2$ and $R^{2'}$, or $R^3$ and $R^{3'}$ form a 3- to 6-membered carbocyclic spiro ring;

or $R^1$ and $R^{1'}$, or $R^2$ and $R^{2'}$, or $R^3$ and $R^{3'}$ form a 3- to 6-membered heterocyclic spiro ring;

each of which ring is unsubstituted or substituted with 1 or more substituents independently chosen from halogen, hydroxyl, cyano, —COOH, $C_1$-$C_4$alkyl, $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di—$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy;

or $R^1$ and $R^{1'}$, $R^2$ and $R^{2'}$, or $R^3$ and $R^{3'}$ form a carbonyl group;

or $R^1$ and $R^2$ or $R^2$ and $R^3$ form a carbon-carbon double bond;

A is

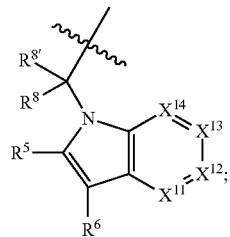

$R^5$ and $R^6$ are independently selected from —CHO, —C(O)$NH_2$, —C(O)NH($CH_3$), $C_2$-$C_6$alkanoyl, hydrogen, hydroxyl, halogen, cyano, nitro, —COOH, —$SO_2NH_2$, vinyl, $C_1$-$C_6$alkyl, $C_2$-$C_6$alkenyl, $C_1$-$C_6$alkoxy, —$C_0$-$C_4$alkyl($C_3$-$C_7$cycloalkyl), —C(O)$C_0$-$C_4$alkyl($C_3$-$C_7$cycloalkyl), —P(O)($OR^9)_2$, —OC(O)$R^9$, —C(O)$OR^9$, —C(O)N($CH_2CH_2R^9$)($R^{10}$), —$NR^9$C(O)$R^{10}$, phenyl, and 5- to 6-membered heteroaryl;

$R^8$ and $R^{8'}$ are independently chosen from hydrogen, halogen, hydroxyl, $C_1$-$C_6$alkyl, —$C_0$-$C_4$alkyl($C_3$-$C_7$cycloalkyl), $C_1$-$C_6$alkoxy, and ($C_1$-$C_4$alkylamino)$C_0$-$C_2$alkyl; or $R^8$ and $R^{8'}$ are taken together to form an oxo group; or $R^8$ and $R^{8'}$ can be taken together with the carbon that they are bonded to form a 3-membered carbocyclic ring;

$X^{11}$ is N or $CR^{11}$;
$X^{12}$ is $CR^{12}$;
$X^{13}$ is $CR^{13}$;
$X^{14}$ is N or $CR^{14}$;
one of $R^{12}$ and $R^{13}$ is chosen from $R^{31}$ and the other of $R^{12}$ and $R^{13}$ is chosen from $R^{32}$;

$R^{31}$ is chosen from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)$OR^9$, $C_1$-$C_6$thioalkyl, —$C_0$-$C_4$alkyl$NR^9R^{10}$, —C(O)$NR^9R^{10}$, —$SO_2R^9$, —$SO_2NR^9R^{10}$, —OC(O)$R^9$, and —C($NR^9$)$NR^9R^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —$CONH_2$, $C_1$-$C_2$haloalkyl, and $C_1$-$C_2$haloalkoxy, and each of which $R^{31}$ is also optionally substituted with one substituent chosen from phenyl and 4- to 7-membered heterocycle containing 1, 2, or 3 heteroatoms independently chosen from N, O, and S; which phenyl or 4- to 7-membered heterocycle is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

$R^{32}$ is selected from —OC(O)$NR^{21}R^{22}$, —OC(O)$NR^{24}R^{25}$, and —OC(O)$NR^9(CH_2)_{1-4}P(O)(OR^{21})(OR^{22})$, $R^{11}$, and $R^{14}$ are independently chosen at each occurrence from hydrogen, halogen, hydroxyl, nitro, cyano, —O(PO)($OR^9)_2$, —(PO)($OR^9)_2$, $C_1$-$C_6$alkyl, $C_2$-$C_6$alkenyl, $C_2$-$C_6$alkynyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy;

$R^{21}$ and $R^{22}$ are independently chosen at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkyl OC(O)O$C_1$-$C_6$alkyl, —$C_1$-$C_4$alkylOC(O)$C_1$-$C_6$alkyl, —$C_1$-$C_4$alkylC(O)O$C_1$-$C_6$alkyl, (4- to 7-membered heterocycloalkyl)$C_0$-$C_4$alkyl having 1, 2, or 3 heteroatoms independently chosen from N, O, and S, and (5- or 6- membered unsaturated or aromatic heterocycle)$C_0$-$C_4$alkyl having 1, 2, or 3 heteroatoms independently chosen from N, O, and S;

$R^{23}$ is independently chosen at each occurrence from $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, and (5- or 6- membered unsaturated or aromatic heterocycle)$C_0$-$C_4$alkyl having 1, 2, or 3 heteroatoms independently chosen from N, O, and S;

$R^{24}$ and $R^{25}$ are taken together with the nitrogen to which they are attached to form a 4- to 7-membered monocyclic heterocycloalkyl group, or a 6- to 10- membered bicyclic heterocyclic group having fused, spiro, or bridged ring;

L is

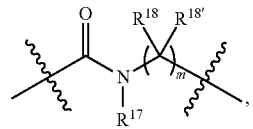

where R$^{17}$ is hydrogen, C$_1$-C$_6$alkyl, or —C$_0$-C$_4$alkyl(C$_3$-C$_7$cycloalkyl), and R$^{18}$ and R$^{18'}$ are independently chosen from hydrogen, halogen, hydroxymethyl, and methyl; and m is 0, 1, 2, or 3;

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; C$_2$-C$_6$alkenyl; C$_2$-C$_6$alkynyl; —(C$_0$-C$_4$alkyl)(aryl); —(C$_0$-C$_4$alkyl)(heteroaryl); or —(C$_0$-C$_4$alkyl)(biphenyl) each of which B is unsubstituted or substituted with one or more substituents independently chosen from R$^{33}$ and R$^{34}$, and 0 or 1 substituents chosen from R$^{35}$ and R$^{36}$;

R$^{33}$ is independently chosen from halogen, hydroxyl, —COOH, cyano, C$_1$-C$_6$alkyl, C$_2$-C$_6$alkanoyl, C$_1$-C$_6$alkoxy, —C$_0$-C$_4$alkylNR$^9$R$^{10}$, —SO$_2$R$^9$, C$_1$-C$_2$haloalkyl, and C$_1$-C$_2$haloalkoxy;

R$^{34}$ is independently chosen from nitro, C$_2$-C$_6$alkenyl, C$_2$-C$_6$alkynyl, C$_1$-C$_6$thioalkyl, —JC$_3$-C$_3$cycloalkyl, —B(OH)$_2$, —JC(O)NR$^9$R$^{23}$, —JOSO$_2$OR$^{21}$, —C(O)(CH$_2$)$_{1-4}$S(O)R$^{21}$, —O(CH$_2$)$_{1-4}$S(O)NR$^{21}$R$^{22}$, —JOP(O)(OR$^{21}$)(OR$^{22}$), —JP(O)(OR$^{21}$)(OR$^{22}$), —JOP(O)(OR$^{21}$)R$^{22}$, —JP(O)(OR$^{21}$)R$^{22}$, —JOP(O)R$^{21}$R$^{22}$, —JP(O)R$^{21}$R$^{22}$, —JSP(O)(OR$^{21}$)(OR$^{22}$), —JSP(O)(OR$^{21}$)(R$^{22}$), —JSP(O)(R$^{21}$)(R$^{22}$), —JNR$^9$P(O)(NHR$^{21}$)(NHR$^{22}$), —JNR$^9$P(O)(OR$^{21}$)(NHR$^{22}$), —JNR$^9$P(O)(OR$^{21}$)(OR$^{22}$), —JC(S)R$^{21}$, —JNR$^{21}$SO$_2$R$^{22}$, —JNR$^9$S(O)NR$^{10}$R$^{22}$, —JNR$^9$SO$_2$NR$^{10}$R$^{22}$, —JSO$_2$NR$^9$COR$^{22}$, —JSO$_2$NR$^9$CONR$^{21}$R$^{22}$, —JNR$^{21}$SO$_2$R$^{22}$, —JC(O)NR$^{21}$SO$_2$R$^{22}$, —JC(NH$_2$)NR$^{22}$, —JC(NH$_2$)NR$^9$S(O)$_2$R$^{22}$, —JOC(O)NR$^{21}$R$^{22}$, —JNR$^{21}$C(O)OR$^{22}$, —JNR$^{21}$OC(O)R$^{22}$, —(CH$_2$)$_{1-4}$C(O)NR$^{21}$R$^{22}$, —JC(O)R$^{24}$R$^{25}$, —JNR$^9$C(O)R$^{21}$, —JC(O)R$^{21}$, —JNR$^9$C(O)NR$^{10}$R$^{22}$, —CCR$^{21}$, —(CH$_2$)$_{1-4}$OC(O)R$^{21}$, and —JC(O)OR$^{23}$; each of which R$^{34}$ may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, C$_1$-C$_6$alkyl, —C$_0$-C$_4$alkyl(C$_3$-C$_7$cycloalkyl), C$_1$-C$_6$alkoxy, —C$_0$-C$_2$alkyl(mono- and di—C$_1$-C$_4$alkylamino), C$_1$-C$_6$alkylester, C$_1$-C$_4$alkylamino, C$_1$-C$_4$hydroxylalkyl, C$_1$-C$_2$haloalkyl, and C$_1$-C$_2$haloalkoxy;

R$^{35}$ is independently chosen from naphthyl, naphthyloxy, indanyl, (4- to 7-membered heterocycloalkyl)C$_0$-C$_4$alkyl containing 1 or 2 heteroatoms chosen from N, O, and S, and bicyclic heterocycle containing 1, 2, or 3 heteroatoms independently chosen from N, O, and S, and containing 4- to 7- ring atoms in each ring; each of which R$^{35}$ is unsubstituted or substituted with one or more substituents independently chosen from halogen, hydroxyl, nitro, cyano, C$_1$-C$_6$alkyl, C$_2$-C$_6$alkenyl, C$_2$-C$_6$alkanoyl, C$_1$-C$_6$alkoxy, (mono- and di-C$_1$-C$_6$alkylamino)C$_0$-C$_4$alkyl, C$_1$-C$_6$alkylester, —C$_0$-C$_4$alkyl(C$_3$-C$_7$cycloalkyl), —SO$_2$R$^9$, C$_1$-C$_2$haloalkyl, and C$_1$-C$_2$haloalkoxy;

R$^{36}$ is independently chosen from tetrazolyl, (phenyl)C$_0$-C$_2$alkyl, (phenyl)C$_1$-C$_2$alkoxy, phenoxy, and 5- or 6-membered heteroaryl containing 1, 2, or 3 heteroatoms independently chosen from N, O, B, and S, each of which R$^{36}$ is unsubstituted or substituted with one or more substituents independently chosen from halogen, hydroxyl, nitro, cyano, C$_1$-C$_6$alkyl, C$_2$-C$_6$alkenyl, C$_2$—C$_0$alkanoyl, C$_1$-C$_6$alkoxy, (mono- and di-C$_1$-C$_6$alkylamino)C$_0$-C$_4$alkyl, C$_1$-C$_6$alkylester, —C$_0$-

C$_4$alkyl(C$_3$-C$_7$cycloalkyl), —SO$_2$R$^9$, —OSi(CH$_3$)$_2$C(CH$_3$)$_3$, —Si(CH$_3$)$_2$C(CH$_3$)$_3$, C$_1$-C$_2$haloalkyl, and C$_1$-C$_2$haloalkoxy; and J is independently selected at each occurrence from a covalent bond, C$_1$-C$_4$alkylene, —OC$_1$-C$_4$alkylene, C$_2$-C$_4$alkenylene, and C$_2$-C$_4$alkynylene.

2. The compound of claim 1, wherein the

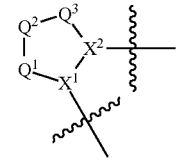

ring is selected from:

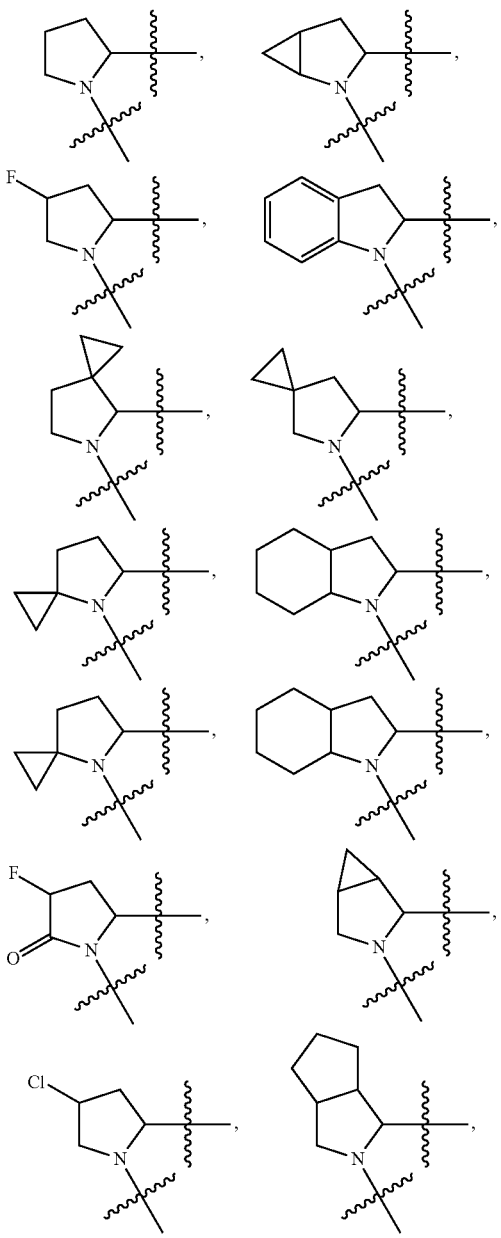

-continued

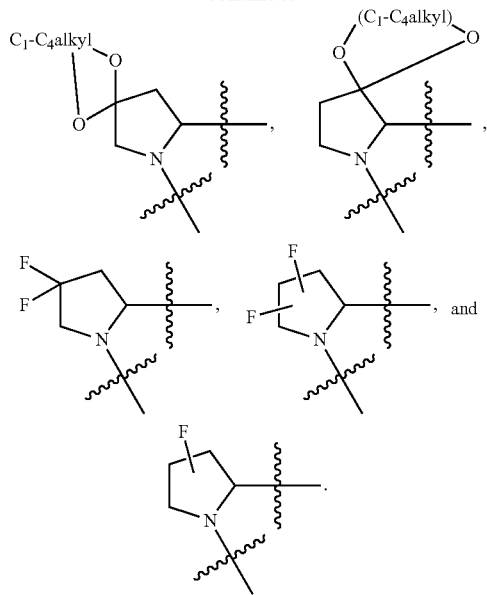

3. The compound of claim 1, wherein $R^1$ and $R^{1'}$ or $R^3$ and $R^{3'}$ can together form a 3- to 6-membered carbocyclic spiro ring or a 3- to 6-membered heterocyclic spiro ring containing 1 or 2 heteroatoms independently chosen from N, O, or S.

4. The compound of claim 1, wherein $R^2$ and $R^{2'}$ can together to form a 3- to 6-membered carbocyclic spiro ring; or $R^2$ and $R^{2'}$ are taken together to form a 3- to 6-membered heterocyclic spiro ring.

5. The compound of claim 1, wherein B is selected from:

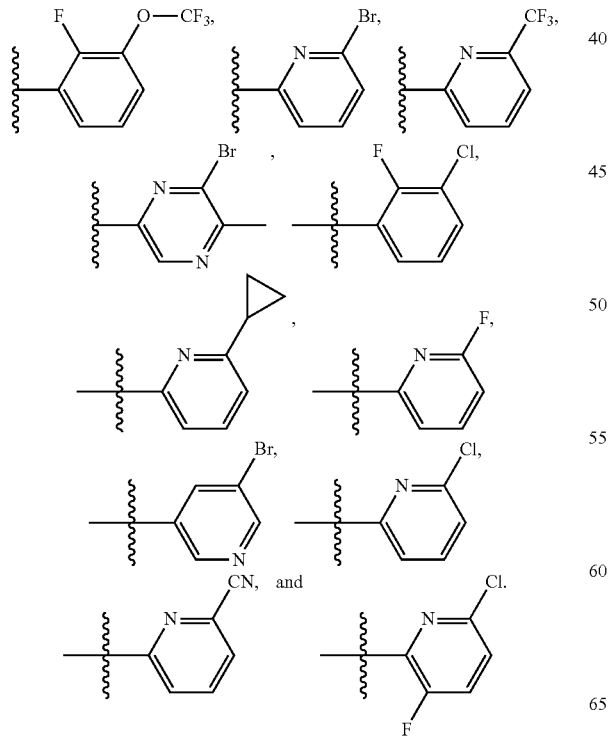

6. The compound of claim 1, wherein $R^{32}$ selected from:

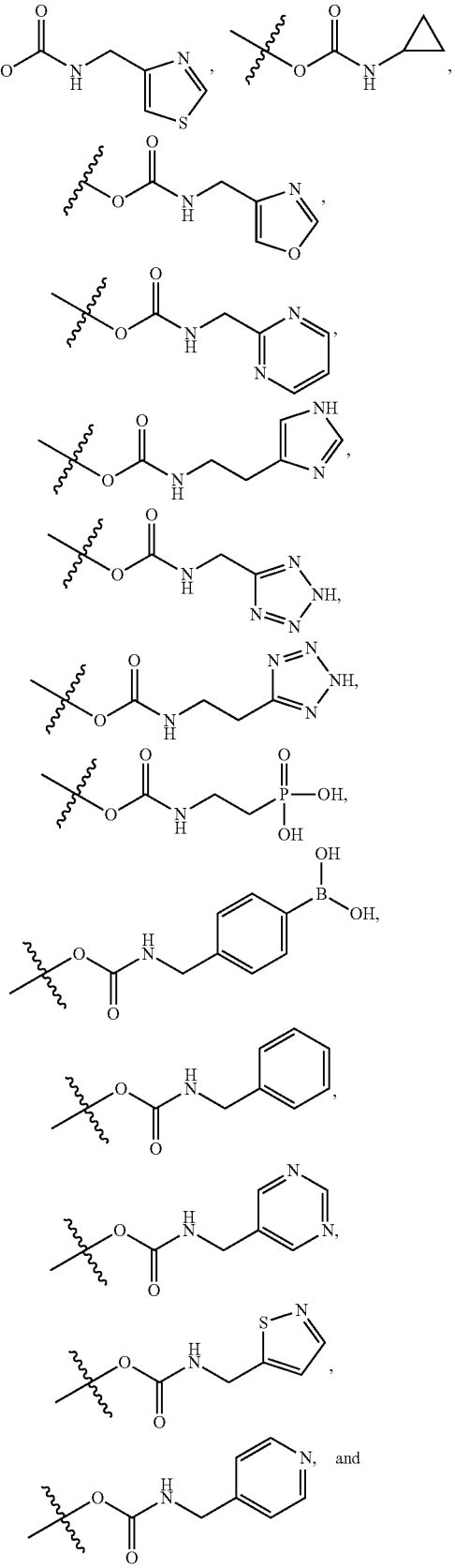

-continued
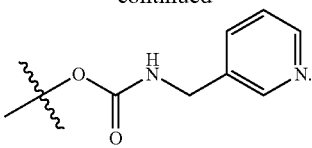
7. The compound of claim 1, wherein R³² is selected from:
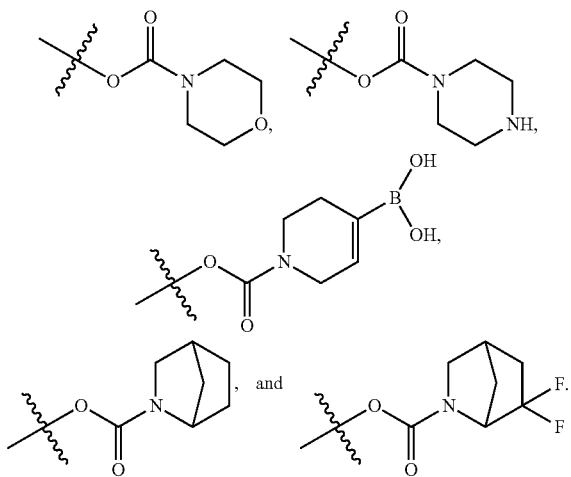
8. The compound of claim 1, wherein B is selected from:
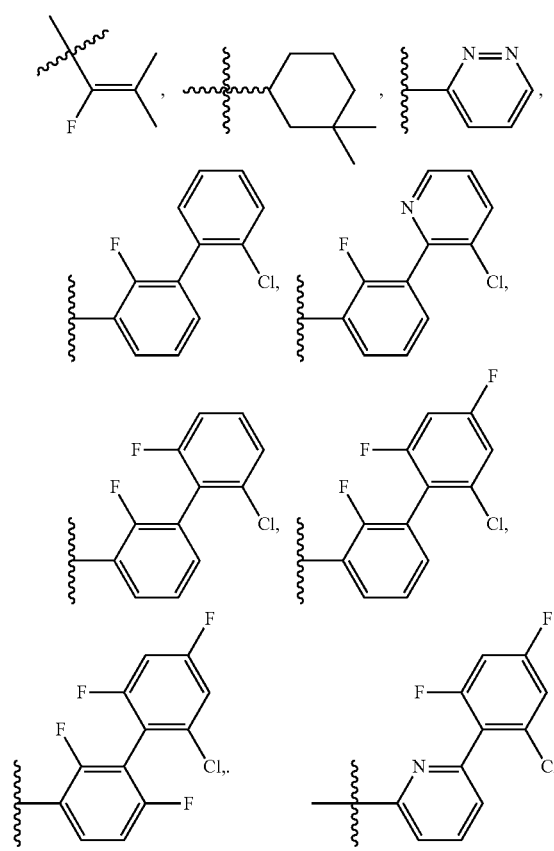
-continued
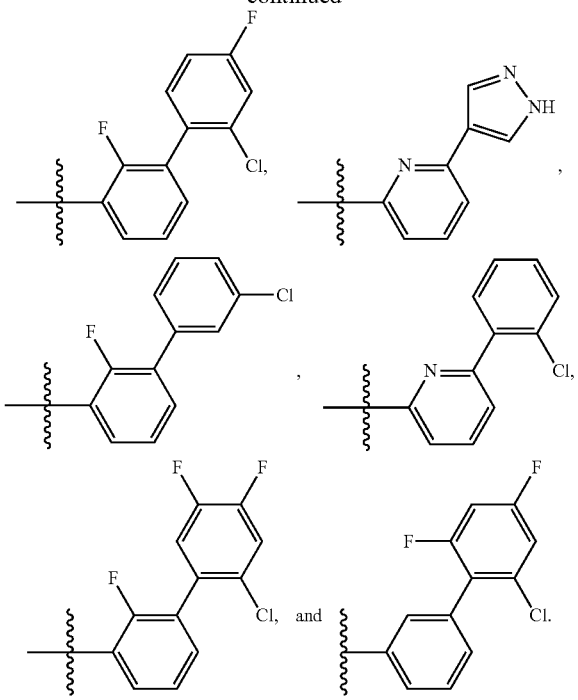
9. The compound of claim 1, wherein B is selected from:
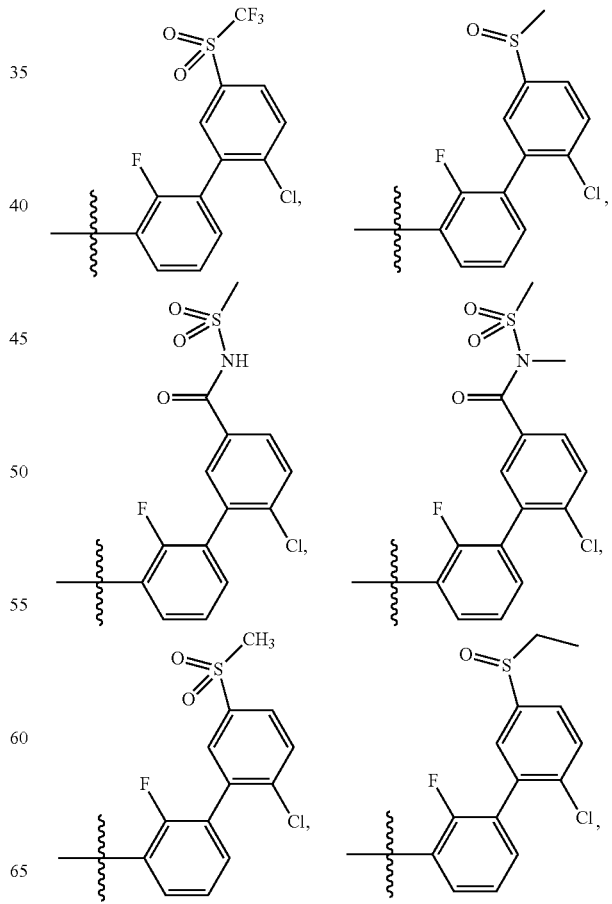

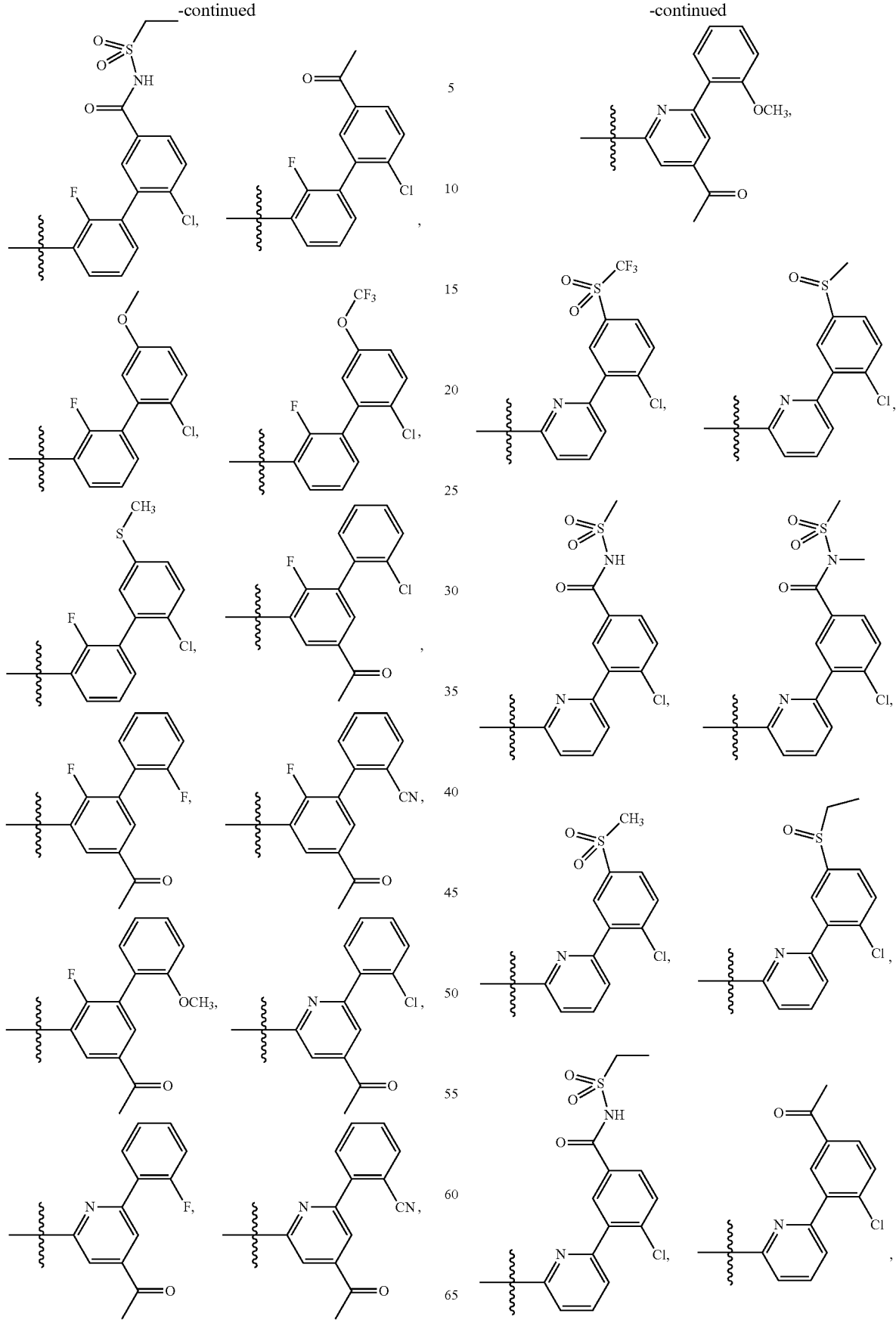

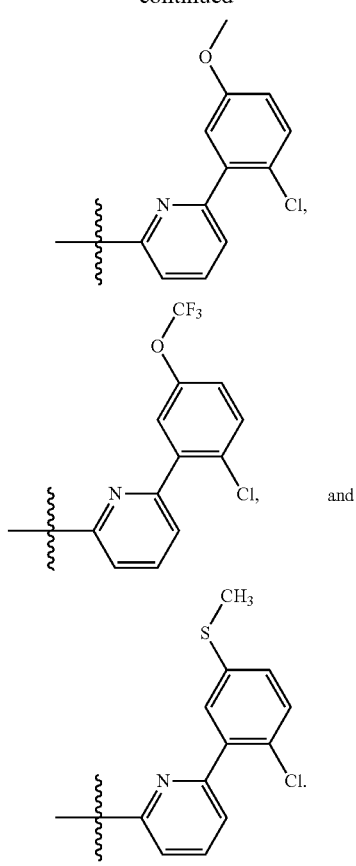
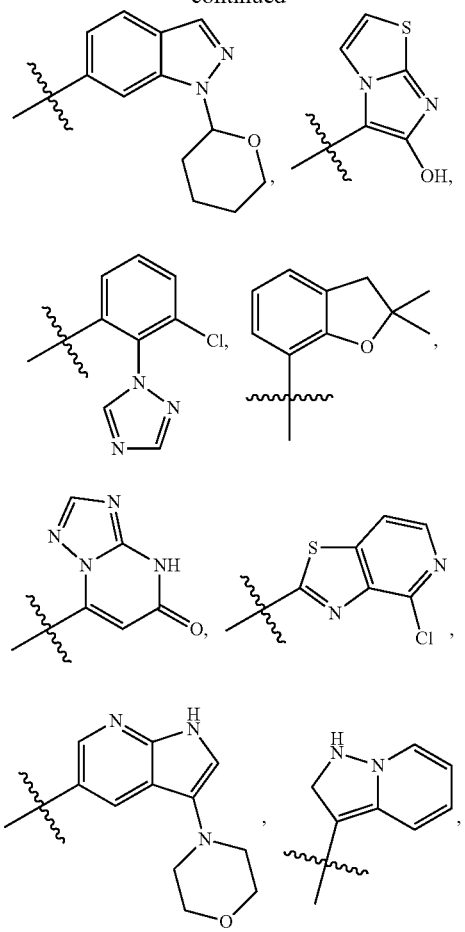
10. The compound of claim 1, wherein B is selected from:
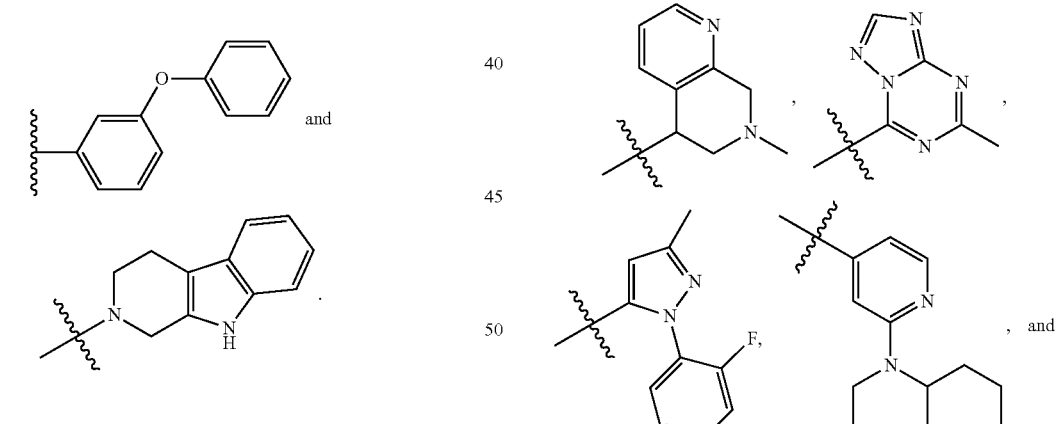
11. The compound of claim 1, wherein B is selected from:
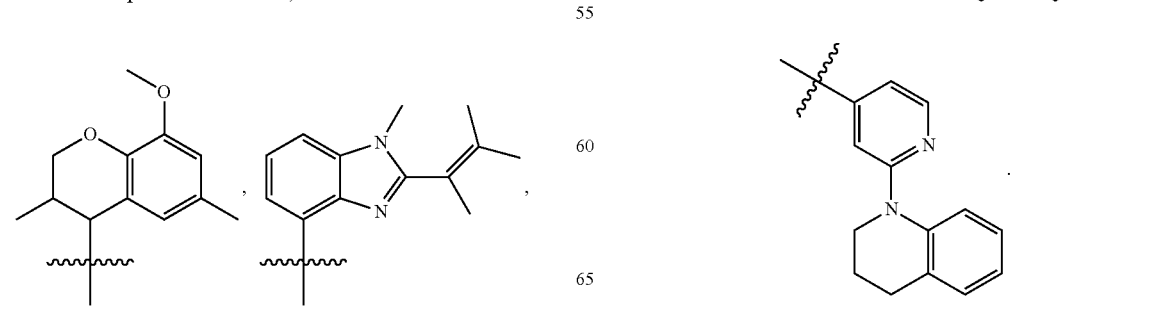

112. The compound of claim 1, wherein B is selected from:
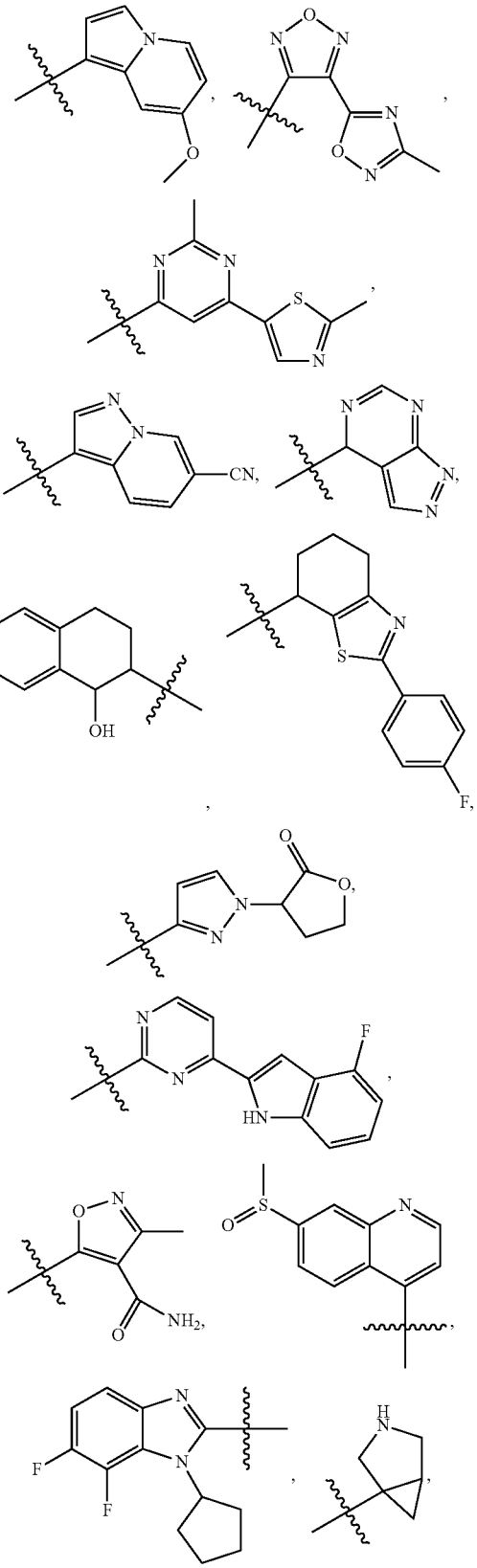
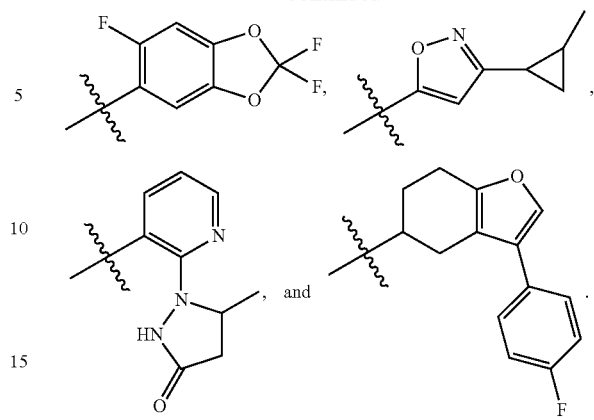
13. The compound of claim 1 of Formula IB
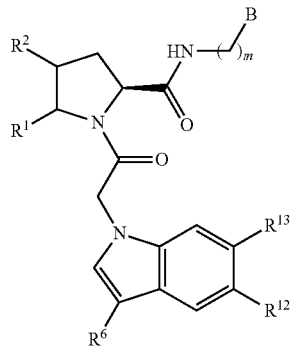
or a pharmaceutically acceptable salt thereof.
14. The compound of claim 1, wherein A is
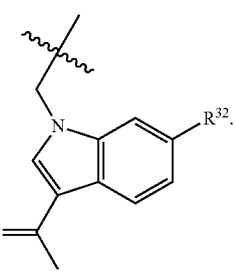
15. The compound of claim 1, wherein A is
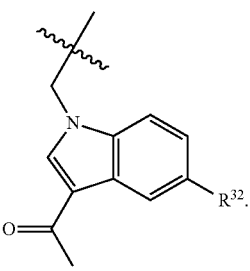

16. The compound of claim 1, wherein A is

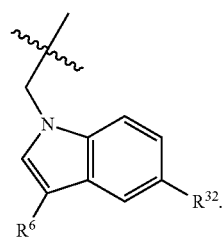

17. The compound of claim 1, wherein

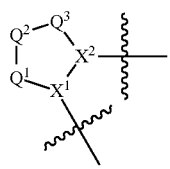

is

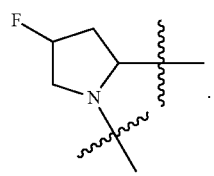

18. The compound of claim 1, wherein $R^{32}$ is —OC(O)NR$^{21}$R$^{22}$.

19. The compound of claim 5, wherein A is

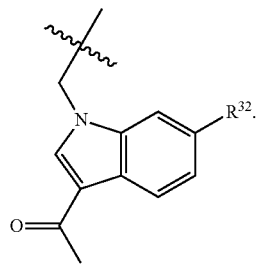

20. The compound of claim 5, wherein A is

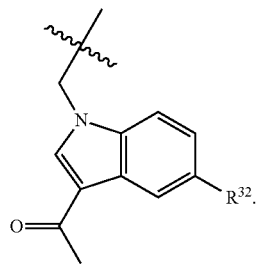

21. The compound of claim 20, wherein

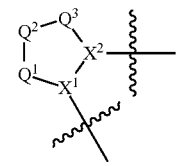

is

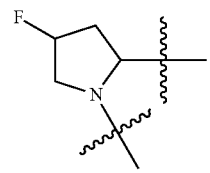

22. The compound of claim 21, wherein $R^{32}$ is —OC(O)NR$^{21}$R$^{22}$.

23. The compound of claim 21, wherein $R^{32}$ selected from:

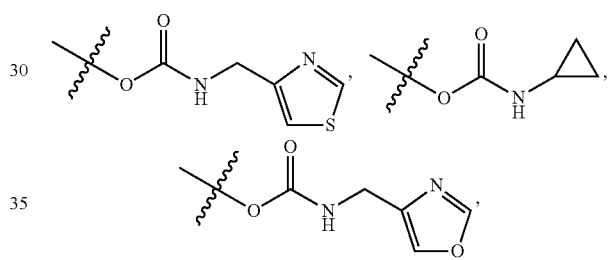

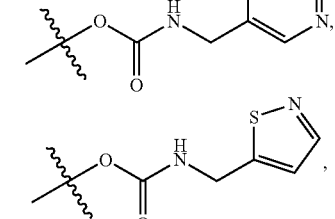

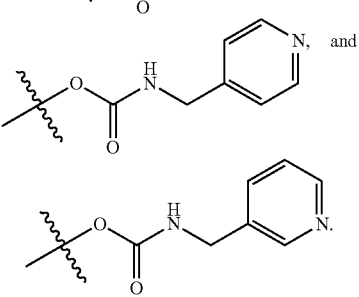

24. The compound of claim 21, wherein $R^{32}$ selected from:

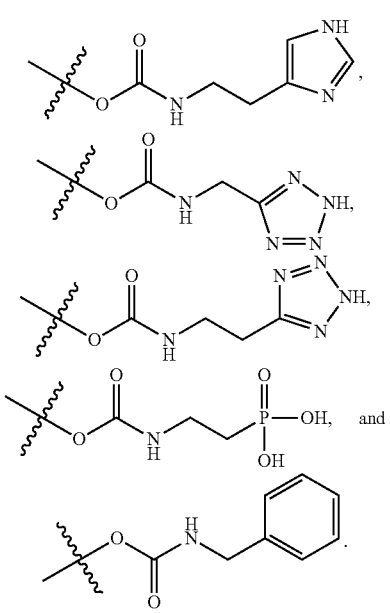

25. The compound of claim 1 of structure:

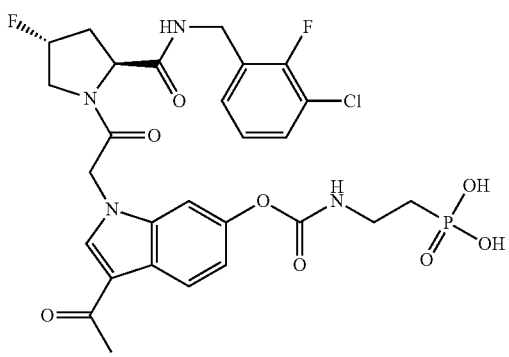 [SMILES: CC(=O)c1cn(CC(=O)N2C[C@H](F)C[C@H]2C(=O)NCc2cccc(Cl)c2F)c2cc(OC(=O)NCCP(=O)(O)O)ccc12]

or a pharmaceutically acceptable salt thereof.

26. The compound of claim 1 of structure:

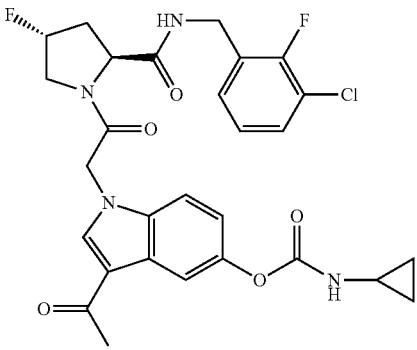 [SMILES: CC(=O)c1cn(CC(=O)N2C[C@H](F)C[C@H]2C(=O)NCc2cccc(Cl)c2F)c2ccc(OC(=O)NC3CC3)cc12]

or a pharmaceutically acceptable salt thereof.

27. The compound of claim 1 of structure:

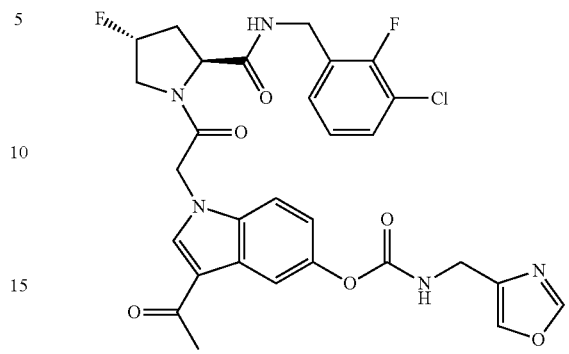

or a pharmaceutically acceptable salt thereof.

28. The compound of claim 1 of structure:

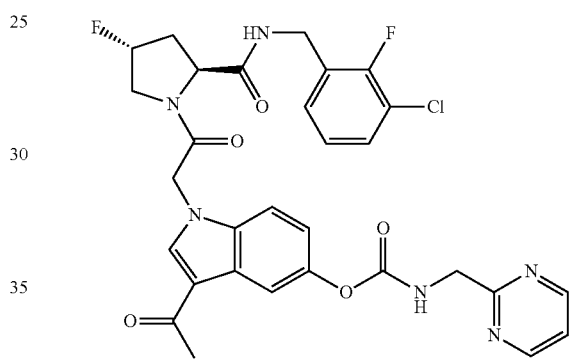

or a pharmaceutically acceptable salt thereof.

29. The compound of claim 1 of structure:

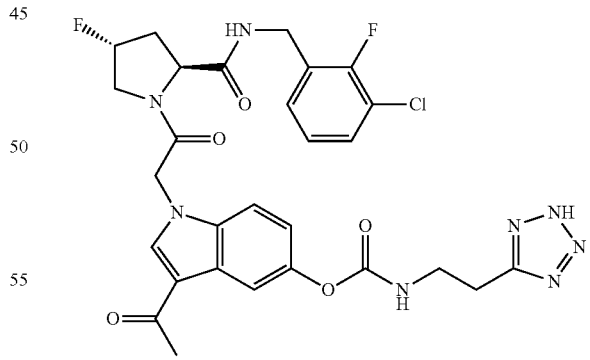

or a pharmaceutically acceptable salt thereof.

* * * * *